(12) United States Patent
Fontayne et al.

(10) Patent No.: US 9,512,230 B2
(45) Date of Patent: Dec. 6, 2016

(54) TRANSCRIPTION UNITS AND THE USE THEREOF IN EXPRESSION VECTORS

(71) Applicants: Alexandre Fontayne, La Madeleine (FR); Francois Coutard, Ales (FR)

(72) Inventors: Alexandre Fontayne, La Madeleine (FR); Francois Coutard, Ales (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 28 days.

(21) Appl. No.: 14/375,503

(22) PCT Filed: Feb. 8, 2013

(86) PCT No.: PCT/FR2013/050267
§ 371 (c)(1),
(2) Date: Jul. 30, 2014

(87) PCT Pub. No.: WO2013/117871
PCT Pub. Date: Aug. 15, 2013

(65) Prior Publication Data
US 2015/0072368 A1    Mar. 12, 2015

(30) Foreign Application Priority Data

Feb. 8, 2012    (FR) .................................... 12 51185

(51) Int. Cl.
*C07K 16/28*    (2006.01)
*C07K 16/34*    (2006.01)
*C12N 15/85*    (2006.01)

(52) U.S. Cl.
CPC ........... *C07K 16/2887* (2013.01); *C07K 16/34* (2013.01); *C12N 15/85* (2013.01); *C12N 2830/007* (2013.01); *C12N 2830/15* (2013.01); *C12N 2830/42* (2013.01); *C12N 2830/60* (2013.01); *C12N 2830/85* (2013.01)

(58) Field of Classification Search
None
See application file for complete search history.

(56) References Cited

U.S. PATENT DOCUMENTS

| 5,024,939 | A * | 6/1991 | Gorman ..................... 435/69.1 |
| 2002/0155430 | A1* | 10/2002 | Marsco et al. ................. 435/5 |
| 2003/0125286 | A1* | 7/2003 | Hauser ................. C07K 14/47 514/44 A |
| 2003/0224477 | A1 | 12/2003 | Heartlein et al. |
| 2004/0132679 | A1 | 7/2004 | Chan et al. |
| 2007/0161110 | A1* | 7/2007 | Iida et al. .................... 435/456 |
| 2008/0250514 | A1* | 10/2008 | Tsunoda et al. ................ 800/13 |
| 2009/0083866 | A1* | 3/2009 | Gu et al. ......................... 800/3 |
| 2009/0170727 | A1* | 7/2009 | Reed ............................... 506/26 |
| 2009/0271884 | A1* | 10/2009 | Poueymirou et al. .......... 800/21 |
| 2012/0309050 | A1* | 12/2012 | Kumon et al. ............... 435/69.1 |

FOREIGN PATENT DOCUMENTS

| WO | 2008/044869 | 4/2008 |
| WO | 2011/062298 | 5/2011 |

OTHER PUBLICATIONS

International Search Report dated Oct. 11, 2013, corresponding to PCT/FR2013/050267.
French Search Report dated Jun. 4, 2012, corresponding to the Foreign Priority Application No. 1251185.
Ramezani, et al.; "Lentiviral Vectors for Enhanced Gene Expression in Human Hematopoietic Cells"; vol. 2, No. 5; Nov. 1, 2000; pp. 458-469.
Liu, et al.; Genomic Organization and Characterization of Promoter Function of Human CDK9 Gene; vol. 252, No. 1-2; Jul. 11, 2000; pp. 51-59.

* cited by examiner

*Primary Examiner* — Addison D Ault
(74) *Attorney, Agent, or Firm* — Young & Thompson

(57) ABSTRACT

Novel transcription units that may be used in expression vectors. The transcription unit allow antibodies to be produced whose gain in productivity is not linked to a particular antigenic target antibody and therefore by extrapolation to a given recombinant protein, nor linked to the culture medium.

8 Claims, 15 Drawing Sheets

SEQUENCE LISTING

```
<160> NUMBER OF SEQ ID NOS: 75

<210> SEQ ID NO 1
<211> LENGTH: 306
<212> TYPE: DNA
<213> ORGANISM: Cytomegalovirus

<400> SEQUENCE: 1
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatgg                                                                306

<210> SEQ ID NO 2
<211> LENGTH: 352
<212> TYPE: DNA
<213> ORGANISM: Homo sapiens

<400> SEQUENCE: 2
catgcagcgg gacgcgccac cccgagcccc agctccggcg ccccggctcc ccgcgccccc      60
gatcggggcc gccgctagta gtggcggcgg cggaggcggg ggcagcggcg gcggcggcgg     120
aggcgcctct gcagctccgg ctcccctgg cctctcggga actacaagtc ccaggggcc      180
```

```
tggcggtggg cggcgggcgg aagaggcggg gtcggcgccg cgaggccgga agtggccgtg    240
gaggcggaag tggcgcggcc gcggaggggc ctggagtgcg gcggcggcgg gacccggagc    300
aggagcggcg gcagcagcga ctgggggcgg cggcggcgcg ttggaggcgg cc            352
```

<210> SEQ ID NO 3
<211> LENGTH: 283
<212> TYPE: DNA
<213> ORGANISM: Gallus gallus

<400> SEQUENCE: 3

```
catggtcgag gtgagcccca cgttctgctt cactctcccc atctcccccc cctcccacc     60 cccaattttg tatttattta ttttttaatt attttgtgca gcgatggggg cgggggggg    120 gggggggcgc gcgccaggcg gggcggggcg gggcgagggg cggggcgggg cgaggcggag   180
aggtgcggcg gcagccaatc agagcggcgc gctccgaaag tttcctttta tggcgaggcg   240
gcggcggcgg cggccctata aaagcgaag cgcgcggcgg gcg                      283
```

<210> SEQ ID NO 4
<211> LENGTH: 267
<212> TYPE: DNA
<213> ORGANISM: Homo sapiens

<400> SEQUENCE: 4

```
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt   120
aagtttaaag ctcaggtcga gaccgggcct tgtccggcg ctcccttgga gcctacctag    180
actcagccgg ctctccacgc tttgcctgac cctgcttgct caactctacg tctttgtttc   240
gttttctgtt ctgcgccgtt acagatc                                       267
```

<210> SEQ ID NO 5
<211> LENGTH: 653
<212> TYPE: DNA
<213> ORGANISM: Homo sapiens

<400> SEQUENCE: 5

```
cagagtaatg acatggttcc ttccatcctc caaaggtgac caataatagt ttgtaagtat    60
cattatgaac taatgaattt tcaacatatt tgatatattt caatccattg ccatcattgt   120
tcttatcgat atttgagttg gctcactttg ccagtaagag tctattcaaa ttggcttctg   180
agtccatttg acacaacacc tttgatcttt gacagtttcc ttggttttag gtgctagatg   240
atttctcagg ctcaccttag acatttcctg ccacagactt agaatcagcc atttctctaa   300
ggaccctgat tccatttcat gagaaatgat agagaccaca atcaaaacaa gtcatgaatt   360
tatactgata ttttcaattc aaattaaaga tgaggttttt gctaaatttt tttgagttta   420
tatttgtatg tcttatgctg aaaaatcttg tttcctaatt agtaacataa ttattcattt   480
gatgggtaaa tattttaggg ccgattcttt ggttttatag ccaagatacc ctgttgataa   540
agtcttgtgg gagcaattat aagactggct tattttgaag ctttttaaaa aagacatcct   600
tacctgtttt aactgtagat tatattaact taaataggta cagcccacgc ttg          653
```

<210> SEQ ID NO 6
<211> LENGTH: 314
<212> TYPE: DNA
<213> ORGANISM: Homo sapiens

```
<400> SEQUENCE: 6
gctggtgggt agggatgagg gaggagggg cattgtgatg tacagggctg ctctgtgaga    60
tcaagggtct cttaagggtg ggagctgggg cagggactac gagagcagcc agatgggctg   120
aaagtggaac tcaaggggtt tctggcacct acctacctgc ttcccgctgg ggggtgggga   180
gttggcccag agtcttaaga ttggggcagg gtggagaggt gggctcttcc tgcttcccac   240
tcatcttata gctttctttc cccagatccg aattcgagat ccaaaccaag gaggaaagga   300
tatcacagag gaga                                                     314

<210> SEQ ID NO 7
<211> LENGTH: 933
<212> TYPE: DNA
<213> ORGANISM: Artificial Sequence
<220> FEATURE:
<223> OTHER INFORMATION: U1U2

<400> SEQUENCE: 7
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt   120
aagtttaaag ctcaggtcga gaccgggcct tgtccggcg ctcccttgga gcctacctag   180
actcagccgg ctctccacgc tttgcctgac cctgcttgct caactctacg tctttgtttc   240
gttttctgtt ctgcgccgtt acagatcact agtgtttaaa cagagtaatg catggttcc   300 ttccatcctc caaaggtgac caataatagt ttgtaagtat cattatgaac taatgaattt   360
tcaacatatt tgatatattt caatccattg ccatcattgt tcttatcgat atttgagttg   420
gctcactttg ccagtaagag tctattcaaa ttggcttctg agtccatttg acacaacacc   480
tttgatcttt gacagtttcc ttggttttag gtgctgatg atttctcagg ctcaccttag    540
acatttcctg ccacagactt agaatcagcc atttctctaa ggaccctgat tccatttcat   600
gagaaatgat agagaccaca atcaaaacaa gtcatgaatt tatactgata ttttcaattc   660
aaattaaaga tgaggttttt gctaaatttt tttgagttta tatttgtatg tcttatgctg   720
aaaaatcttg tttcctaatt agtaacataa ttattcattt gatgggtaaa tattttaggg   780
ccgattcttt ggttttatag ccaagatacc ctgttgataa agtcttgtgg gagcaattat   840
aagactggct tattttgaag cttttttaaaa aagacatcct tacctgtttt aactgtagat   900
tatattaact aaataggta cagcccacgc ttg                                 933

<210> SEQ ID NO 8
<211> LENGTH: 591
<212> TYPE: DNA
<213> ORGANISM: Artificial Sequence
<220> FEATURE:
<223> OTHER INFORMATION: U1U3

<400> SEQUENCE: 8
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt   120
aagtttaaag ctcaggtcga gaccgggcct tgtccggcg ctcccttgga gcctacctag   180
actcagccgg ctctccacgc tttgcctgac cctgcttgct caactctacg tctttgtttc   240
gttttctgtt ctgcgccgtt acagatcact agttaacgct ggtgggtagg gatgagggag   300
ggaggggcat tgtgatgtac agggctgctc tgtgagatca agggtctctt aagggtggga   360
gctggggcag ggactacgag agcagccaga tgggctgaaa gtggaactca agggtttct   420
```
ggcacctacc tacctgcttc ccgctggggg gtggggagtt ggcccagagt cttaagattg    480
gggcagggtg gagaggtggg ctcttcctgc ttcccactca tcttatagct ttctttcccc    540
agatccgaat tcgagatcca aaccaaggag gaaaggatat cacagaggag a             591

<210> SEQ ID NO 9
<211> LENGTH: 977
<212> TYPE: DNA
<213> ORGANISM: Artificial Sequence
<220> FEATURE:
<223> OTHER INFORMATION: U2U3

<400> SEQUENCE: 9
cagagtaatg acatggttcc ttccatcctc caaaggtgac caataatagt ttgtaagtat     60
cattatgaac taatgaattt tcaacatatt tgatatattt caatccattg ccatcattgt    120
tcttatcgat atttgagttg gctcactttg ccagtaagag tctattcaaa ttggcttctg    180
agtccatttg acacaacacc tttgatcttt gacagtttcc ttggttttag gtgctagatg    240
atttctcagg ctcaccttag acatttcctg ccacagactt agaatcagcc atttctctaa    300
ggaccctgat tccatttcat gagaaatgat agagaccaca atcaaaacaa gtcatgaatt    360
tatactgata ttttcaattc aaattaaaga tgaggttttt gctaaatttt tttgagttta    420
tatttgtatg tcttatgctg aaaaatcttg tttcctaatt agtaacataa ttattcattt    480
gatgggtaaa tattttaggg ccgattcttt ggttttatag ccaagatacc ctgttgataa    540
agtcttgtgg gagcaattat aagactggct tattttgaag ctttttaaaa aagacatcct    600
tacctgtttt aactgtagat tatattaact taaataggta cagcccacgc ttgactagtt    660
aacgctggtg ggtagggatg agggaggag gggcattgtg atgtacaggg ctgctctgtg    720
agatcaaggg tctcttaagg gtgggagctg gggcagggac tacgagagca gccagatggg    780
ctgaaagtgg aactcaaggg gtttctggca cctacctacc tgcttcccgc tgggggtgg    840 ggagttggcc cagagtctta agattgggc agggtggaga ggtgggctct tcctgcttcc    900
cactcatctt atagctttct ttccccagat ccgaattcga gatccaaacc aaggaggaaa    960
ggatatcaca gaggaga                                                   977

<210> SEQ ID NO 10
<211> LENGTH: 1257
<212> TYPE: DNA
<213> ORGANISM: Artificial Sequence
<220> FEATURE:
<223> OTHER INFORMATION: U1U2U3

<400> SEQUENCE: 10
ggctcgcatc tctccttcac gcgcccgccg ccctacctga ggccgccatc cacgccggtt     60
gagtcgcgtt ctgccgcctc ccgcctgtgg tgcctcctga actgcgtccg ccgtctaggt    120
aagtttaaag ctcaggtcga gaccgggcct tgtccggcg ctcccttgga gcctacctag    180
actcagccgg ctctccacgc tttgcctgac cctgcttgct caactctacg tctttgtttc    240
gttttctgtt ctgcgccgtt acagatcact agtgtttaaa cagagtaatg acatggttcc    300
ttccatcctc caaaggtgac caataatagt ttgtaagtat cattatgaac taatgaattt    360
tcaacatatt tgatatattt caatccattg ccatcattgt tcttatcgat atttgagttg    420
gctcactttg ccagtaagag tctattcaaa ttggcttctg agtccatttg acacaacacc    480
tttgatcttt gacagtttcc ttggttttag gtgctagatg atttctcagg ctcaccttag    540

```
acatttcctg ccacagactt agaatcagcc atttctctaa ggaccctgat tccatttcat    600
gagaaatgat agagaccaca atcaaaacaa gtcatgaatt tatactgata ttttcaattc    660
aaattaaaga tgaggttttt gctaaatttt tttgagttta tatttgtatg tcttatgctg    720
aaaaatcttg tttcctaatt agtaacataa ttattcattt gatgggtaaa tattttaggg    780
ccgattcttt ggttttatag ccaagatacc ctgttgataa agtcttgtgg gagcaattat    840
aagactggct tattttgaag ctttttaaaa aagacatcct tacctgtttt aactgtagat    900
tatattaact taaataggta cagcccacgc ttgactagtt aacgctggtg ggtagggatg    960
agggagggag gggcattgtg atgtacaggg ctgctctgtg agatcaaggg tctcttaagg   1020
gtgggagctg gggcagggac tacgagagca gccagatggg ctgaaagtgg aactcaaggg   1080
gtttctggca cctacctacc tgcttcccgc tgggggggtgg ggagttggcc cagagtctta   1140
agattggggc agggtggaga ggtgggctct tcctgcttcc cactcatctt atagctttct   1200
ttccccagat ccgaattcga gatccaaacc aaggaggaaa ggatatcaca gaggaga      1257
```

<210> SEQ ID NO 11
<211> LENGTH: 939
<212> TYPE: DNA
<213> ORGANISM: Homo sapiens

<400> SEQUENCE: 11

```
gtaagtgccg tgtgtggttc ccgcgggcct ggcctcttta cgggttatgg cccttgcgtg     60
ccttgaatta cttccacctg gctgcagtac gtgattcttg atcccgagct tcgggttgga    120
agtgggtggg agagttcgag gccttgcgct taaggagccc cttcgcctcg tgcttgagtt    180
gaggcctggc ctgggcgctg gggccgccgc gtgcgaatct ggtggcacct tcgcgcctgt    240
ctcgctgctt tcgataagtc tctagccatt taaaattttt gatgacctgc tgcgacgctt    300
tttttctggc aagatagtct tgtaaatgcg ggccaagatc tgcacactgg tatttcggtt    360
tttgggggccg cggcggcga cggggcccgt gcgtcccagc gcacatgttc ggcgaggcgg    420
ggcctgcgag cgcggccacc gagaatcgga cgggggtagt ctcaagctgg ccggcctgct    480
ctggtgcctg gcctcgcgcc gccgtgtatc gcccgccct gggcggcaag gctggccgg     540
tcggcaccag ttgcgtgagc ggaaagatgg ccgcttcccg gccctgctgc agggagctca    600
aaatggagga gcggcgctc gggagagcgg gcgggtgagt cacccacaca aaggaaaagg    660
gcctttccgt cctcagccgt cgcttcatgt gactccacgg agtaccgggc gccgtccagg    720
cacctcgatt agttctcgag cttttggagt acgtcgtctt taggttgggg ggaggggttt    780
tatgcgatgg agtttcccca cactgagtgg gtggagactg aagttaggcc agcttggcac    840
ttgatgtaat tctccttgga atttgcccct tttgagtttg gatcttggtt cattctcaag    900
cctcagacag tggttcaaag ttttttttctt ccatttcag                          939
```

<210> SEQ ID NO 12
<211> LENGTH: 351
<212> TYPE: DNA
<213> ORGANISM: Mus musculus

<400> SEQUENCE: 12

```
gtaggggatc gggactctgg cgggagggcg gcttggtgcg tttgcgggga tgggcggccg     60
cggcaggccc tccagcgtg gtgagccgt tctgtgagac agccgggtac gagtcgtgac     120
gctgaagggg gcaagcgggt ggtgggcagg aatgcggtcc gccctgcagc aaccggaggg    180
ggagggagaa gggagcggaa aagtctccac cggacgcggc catggctcgg ggggggggg     240
```

```
gcagcggagg agcgcttccg gccgacgtct cgtcgctgat tggcttcttt tcctcccgcc    300
gtgtgtgaaa acacaattgt actaaccttc ttctctttcc tctcctgaca g              351
```

<210> SEQ ID NO 13
<211> LENGTH: 1217
<212> TYPE: DNA
<213> ORGANISM: Homo sapiens

<400> SEQUENCE: 13

```
gtaggggagc ggaactctgg tgggagggga ggtgcggtgc actgggggga tgggtggcta     60
ggggggccgt ctggtggctt gcggggttg cctttcccgt gggaagtcgg aacataatg     120 tttgttacgt tgggagggaa aggggtggct ggatgcaggc gggagggagg cccgccctgc   180
ggcaaccgga gggggaggga aagggagcg gaaaatgctc gaaaccggac ggagccattg   240
ctctcgcaga gggaggagcg cttccggcta gcctcttgtc gccgattggc cgtttctcct   300
cccgccgtgt gtgaaaacac aaatggcgta ttctggttgg agtaaagctc ctgtcagtta   360
caccgtcggg agtacgcagc cgcttagcga ctctcgcgtt gcccctggg tggggcgggt   420 aggtaggtgg ggtgtagaga tgctgggtgt gcggcgcgg ccggcctcct gcggcgggag   480
gggagggtca gtgaaattgg ctctggcgcg ggcgtcctcc cacctcccc ttccttcggg    540 ggagtcggtt tacccgccgc ctgcttgtct tcgacacctg attggctgtc gaagctgtgg   600
gaccgggccc ttgctactgg ctcgagtctc acatgagcga aaccactgcg cggggcgcgg   660
gggtggcggg gaggcgggcg ttggtacggt cctccccgag gccgagcgcc gcagtgtctg   720
gccccgcgcc cctgcgcaac gtggcaggaa gcgcgcgctg gaggcggggg cgggctgccg   780
gccgagactt ctggatggcg gcggccgcg ctccgccccg gttcccacc gcctgaaggg    840 cgagacaagc ccgacctgct acaggcactc gtggggtgg gggaggagcg ggggtcggtc   900
cggctggttt gtgggtggga ggcgcttgtt ctccaaaaac cggcgcgagc tgcaatcctg   960
agggagctgc ggtggaggag gtggagagaa ggccgcaccc ttctgggcag ggggagggga  1020
gtgccgcaat accttttatgg gagttctttg ctgcctcccg tcttgtaagg accgccctgg  1080
gcctggaaga agccctccct cctttcctcc tcgcgtgatc tcgtcatcgc ctccatgtcg  1140
agtcgcttct cgattatggg cgggattctt ttgcctagac aattgtacta accttcttct  1200
ctttcctctc ctgacag                                                  1217
```

<210> SEQ ID NO 14
<211> LENGTH: 951
<212> TYPE: DNA
<213> ORGANISM: Artificial Sequence
<220> FEATURE:
<223> OTHER INFORMATION: CMV-CDK9-U1

<400> SEQUENCE: 14

```
gcgttacata acttacggta aatggcccgc ctggctgacc gcccaacgac ccccgcccat     60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg gtcgcgacga tgcagcggga cgcgccaccc cgagcccag ctccggcgcc    360 ccggctcccc gcgcccccga tcggggccgc cgctagtagt ggcggcggcg gaggcggggg   420
```

| | |
|---|---|
| cagcggcggc ggcggcggag gcgcctctgc agctccggct cccctggcc tctcgggaac | 480 |
| tacaagtccc aggggcctg gcggtgggcg cggcggaa gaggcggt cggcgccgcg | 540 |
| aggccggaag tggccgtgga ggcggaagtg gcgcggccgc ggagggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat c | 951 |

<210> SEQ ID NO 15
<211> LENGTH: 1336
<212> TYPE: DNA
<213> ORGANISM: Artificial Sequence
<220> FEATURE:
<223> OTHER INFORMATION: CMV-CDK9-U2

<400> SEQUENCE: 15

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcgggg | 420 |
| cagcggcggc ggcggcggag gcgcctctgc agctccggct cccctggcc tctcgggaac | 480 |
| tacaagtccc aggggcctg gcggtgggcg cggcggaa gaggcggt cggcgccgcg | 540 |
| aggccggaag tggccgtgga ggcggaagtg gcgcggccgc ggagggcct ggagtgcggc | 600 |
| ggcggcggga cccggagcag gagcggcggc agcagcgact gggggcggcg gcggcgcgtt | 660 |
| ggaggcggcc ggatccgttt aaacagagta atgacatggt tccttccatc ctccaaggt | 720 |
| gaccaataat agtttgtaag tatcattatg aactaatgaa ttttcaacat atttgatata | 780 |
| tttcaatcca ttgccatcat tgttcttatc gatatttgag ttggctcact tgccagtaa | 840 |
| gagtctattc aaattggctt ctgagtccat ttgacacaac acctttgatc tttgacagtt | 900 |
| tccttggttt taggtgctag atgatttctc aggctcacct tagacatttc ctgccacaga | 960 |
| cttagaatca gccatttctc taaggaccct gattccattt catgagaaat gatagagacc | 1020 |
| acaatcaaaa caagtcatga atttatactg atattttcaa ttcaaattaa agatgaggtt | 1080 |
| tttgctaaat tttttgagt ttatatttgt atgtcttatg ctgaaaaatc ttgtttccta | 1140 |
| attagtaaca taattattca tttgatgggt aaatatttta gggccgattc tttggttta | 1200 |
| tagccaagat accctgttga taaagtcttg tgggagcaat tataagactg gcttattttg | 1260 |
| aagcttttta aaaagacat ccttacctgt tttaactgta gattatatta acttaaatag | 1320 |
| gtacagccca cgcttg | 1336 |

<210> SEQ ID NO 16
<211> LENGTH: 997
<212> TYPE: DNA
<213> ORGANISM: Artificial Sequence

<220> FEATURE:
<223> OTHER INFORMATION: CMV-CDK9-U3

<400> SEQUENCE: 16

| | | | | |
|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | ggtcgcgaca | tgcagcggga | cgcgccaccc | cgagcccag | ctccggcgcc | 360 |
| ccggctcccc | gcgccccga | tcgggccgc | cgctagtagt | ggcggcggcg | gaggcggggg | 420 |
| cagcggcggc | ggcggcggag | gcgcctctgc | agctccggct | cccctggcc | tctcgggaac | 480 |
| tacaagtccc | aggggcctg | gcggtgggcg | gcgggcggaa | gaggcggggt | cggcgccgcg | 540 |
| aggccggaag | tggccgtgga | ggcggaagtg | gcgcggccgc | ggagggggcct | ggagtgcggc | 600 |
| ggcggcggga | cccggagcag | gagcggcggc | agcagcgact | ggggggcggcg | gcggcgcgtt | 660 |
| ggaggcggcc | ggatccgttt | aacgctggtg | ggtaggatg | agggagggag | gggcattgtg | 720 |
| atgtacaggg | ctgctctgtg | agatcaaggg | tctcttaagg | gtgggagctg | gggcagggac | 780 |
| tacgagagca | gccagatggg | ctgaaagtgg | aactcaaggg | gtttctggca | cctacctacc | 840 |
| tgcttcccgc | tggggggtgg | ggagttggcc | cagagtctta | agattggggc | agggtggaga | 900 |
| ggtgggctct | tcctgcttcc | cactcatctt | atagctttct | ttccccagat | ccgaattcga | 960 |
| gatccaaacc | aaggaggaaa | ggatatcaca | gaggaga | | | 997 |

<210> SEQ ID NO 17
<211> LENGTH: 1617
<212> TYPE: DNA
<213> ORGANISM: Artificial Sequence
<220> FEATURE:
<223> OTHER INFORMATION: CMV-CDK9-U1U2

<400> SEQUENCE: 17

| | | | | |
|---|---|---|---|---|
| gcgttacata | acttacggta | aatggcccgc | ctggctgacc | gcccaacgac | ccccgcccat | 60 |
| tgacgtcaat | aatgacgtat | gttcccatag | taacgccaat | agggactttc | cattgacgtc | 120 |
| aatgggtgga | gtatttacgg | taaactgccc | acttggcagt | acatcaagtg | tatcatatgc | 180 |
| caagtacgcc | ccctattgac | gtcaatgacg | gtaaatggcc | cgcctggcat | tatgcccagt | 240 |
| acatgacctt | atgggacttt | cctacttggc | agtacatcta | cgtattagtc | atcgctatta | 300 |
| ccatggcccg | ggtcgcgaca | tgcagcggga | cgcgccaccc | cgagcccag | ctccggcgcc | 360 |
| ccggctcccc | gcgccccga | tcgggccgc | cgctagtagt | ggcggcggcg | gaggcggggg | 420 |
| cagcggcggc | ggcggcggag | gcgcctctgc | agctccggct | cccctggcc | tctcgggaac | 480 |
| tacaagtccc | aggggcctg | gcggtgggcg | gcgggcggaa | gaggcggggt | cggcgccgcg | 540 |
| aggccggaag | tggccgtgga | ggcggaagtg | gcgcggccgc | ggagggggcct | ggagtgcggc | 600 |
| ggcggcggga | cccggagcag | gagcggcggc | agcagcgact | ggggggcggcg | gcggcgcgtt | 660 |
| ggaggcggcc | ggatccgttt | aaacggctcg | catctctcct | tcacgcgccc | gccgccctac | 720 |
| ctgaggccgc | catccacgcc | ggttgagtcg | cgttctgccg | cctcccgcct | gtggtgcctc | 780 |
| ctgaactgcg | tccgccgtct | aggtaagttt | aaagctcagg | tcgagaccgg | gcctttgtcc | 840 |
| ggcgctccct | tggagcctac | ctagactcag | ccggctctcc | acgctttgcc | tgaccctgct | 900 |

```
tgctcaactc tacgtctttg tttcgttttc tgttctgcgc cgttacagat cactagtgtt    960
taaacagagt aatgacatgg ttccttccat cctccaaagg tgaccaataa tagttgtaa    1020 gtatcattat gaactaatga attttcaaca tatttgatat atttcaatcc attgccatca   1080
ttgttcttat cgatatttga gttggctcac tttgccagta agagtctatt caaattggct    1140
tctgagtcca tttgacacaa cacctttgat ctttgacagt ttccttggtt ttaggtgcta    1200 gatgattct caggctcacc ttagacattt cctgccacag acttagaatc agccattct    1260 ctaaggaccc tgattccatt tcatgagaaa tgatagagac cacaatcaaa acaagtcatg   1320
aatttatact gatattttca attcaaatta aagatgaggt ttttgctaaa ttttttgag    1380 tttatatttg tatgtcttat gctgaaaaat cttgttcct aattagtaac ataattattc    1440
atttgatggg taaatatttt agggccgatt cttgtgttt atagccaaga taccctgttg   1500
ataaagtctt gtgggagcaa ttataagact ggcttatttt gaagcttttt aaaaaagaca    1560
tccttacctg ttttaactgt agattatatt aacttaaata ggtacagccc acgcttg     1617

<210> SEQ ID NO 18
<211> LENGTH: 1275
<212> TYPE: DNA
<213> ORGANISM: Artificial Sequence
<220> FEATURE:
<223> OTHER INFORMATION: CMV-CDK9-U1U3

<400> SEQUENCE: 18
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc     360 ccggctcccc gcgccccga tcggggccgc cgctagtagt ggcggcggcg gaggcggggg    420
cagcggcggc ggcggcggag gcgcctctgc agctccggct cccctggcc tctcgggaac    480 tacaagtccc agggggcctg cgtggggcg gcgggcggaa gaggcgggt cggcgccgcg     540 aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg ccttttgtcc    840
ggcgctccct tggagcctac ctagactcag ccggctctcc acgctttgcc tgaccctgct    900
tgctcaactc tacgtctttg tttcgttttc tgttctgcgc cgttacagat cactagttaa    960
cgctggtggg tagggatgag ggaggagggg gcattgtgat gtacagggct gctctgtgag   1020
atcaagggtc tcttaagggt gggagctggg gcagggacta cgagagcagc cagatgggct    1080
gaaagtggaa ctcaagggt ttctggcacc tacctacctg cttcccgctg ggggtgggg    1140 agttggccca gagtcttaag attggggcag ggtggagagg tgggctcttc ctgcttccca    1200
ctcatcttat agctttcttt ccccagatcc gaattcgaga tccaaaccaa ggaggaaagg    1260
atatcacaga ggaga                                                    1275
```

<210> SEQ ID NO 19
<211> LENGTH: 1660
<212> TYPE: DNA
<213> ORGANISM: Artificial Sequence
<220> FEATURE:
<223> OTHER INFORMATION: CMV-CDK9-U2U3

<400> SEQUENCE: 19

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360
ccggctcccc gcgccccga tcggggccgc cgctagtagt ggcggcggcg gaggcggggg      420
cagcggcggc ggcggcggag gcgcctctgc agctccggct cccccctggcc tctcgggaac    480
tacaagtccc aggggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacagagta atgacatggt tccttccatc ctccaaaggt    720
gaccaataat agtttgtaag tatcattatg aactaatgaa ttttcaacat atttgatata    780
tttcaatcca ttgccatcat tgttcttatc gatatttgag ttggctcact ttgccagtaa    840
gagtctattc aaattggctt ctgagtccat ttgacacaac acctttgatc tttgacagtt    900
tccttggttt taggtgctag atgatttctc aggctcacct tagacatttc ctgccacaga    960
cttagaatca gccatttctc taaggaccct gattccattt catgagaaat gatagagacc   1020
acaatcaaaa caagtcatga atttatactg atatttcaa ttcaaattaa agatgaggtt    1080
tttgctaaat ttttttgagt ttatatttgt atgtcttatg ctgaaaaatc ttgtttccta    1140
attagtaaca taattattca tttgatgggt aaatatttta gggccgattc tttggtttta    1200
tagccaagat accctgttga taaagtcttg tgggagcaat tataagactg cttatttttg    1260
aagctttta aaaagacat ccttacctgt tttaactgta gattatatta acttaaatag      1320
gtacagccca cgcttgacta gttaacgctg gtgggtaggg atgagggagg gaggggcatt    1380
gtgatgtaca gggctgctct gtgagatcaa gggtctctta agggtgggag ctggggcagg    1440
gactacgaga gcagccagat gggctgaaag tggaactcaa ggggtttctg gcacctacct    1500
acctgcttcc cgctggggg tgggagttg gcccagagtc ttaagattgg ggcagggtgg      1560
agaggtgggc tcttcctgct tcccactcat cttatagctt tctttcccca gatccgaatt    1620
cgagatccaa accaaggagg aaaggatatc acagaggaga                          1660
```

<210> SEQ ID NO 20
<211> LENGTH: 1941
<212> TYPE: DNA
<213> ORGANISM: Artificial Sequence
<220> FEATURE:
<223> OTHER INFORMATION: CMV-CDK9-U1U2U3

<400> SEQUENCE: 20

```
gcgttacata acttacggta aatggcccgc ctggctgacc gcccaacgac ccccgcccat      60
tgacgtcaat aatgacgtat gttcccatag taacgccaat agggactttc cattgacgtc     120
```

```
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc      360 ccggctcccc gcgcccccga tcggggccgc cgctagtagt ggcggcggcg gaggcggggg    420
cagcggcggc ggcggcggag gcgcctctgc agctccggct cccctgccc tctcgggaac     480 tacaagtccc aggggcctg gcgtgggcg gcgggcggaa gaggcggggt cggcgccgcg      540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt     660 ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagtttgtaa   1020
gtatcattat gaactaatga attttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200 gatgattttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa ttttttttgag   1380 tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttatttt gaagctttt aaaaaagaca    1560 tccttacctg ttttaactgt agattatatt aacttaaata ggtacagccc acgcttgact   1620
agttaacgct ggtgggtagg gatgagggag ggaggggcat tgtgatgtac agggctgctc   1680
tgtgagatca agggtctctt aagggtggga gctgggcag ggactacgag agcagcaga    1740 tgggctgaaa gtggaactca aggggtttct ggcacctacc tacctgcttc ccgctggggg   1800
gtggggagtt ggcccagagt cttaagattg gggcagggtg gagaggtggg ctcttcctgc   1860
ttcccactca tcttatagct ttctttcccc agatccgaat tcgagatcca aaccaaggag   1920
gaaaggatat cacagaggag a                                             1941
```

<210> SEQ ID NO 21
<211> LENGTH: 881
<212> TYPE: DNA
<213> ORGANISM: Artificial Sequence
<220> FEATURE:
<223> OTHER INFORMATION: CMV-bActine-U1

<400> SEQUENCE: 21

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
```

```
acatgacctt atgggacttt cctacttggc agtacatcta cgtattagtc atcgctatta      300
ccatggcccg ggtcgcgaca tggtcgaggt gagcccacg ttctgcttca ctctccccat       360
ctcccccccc tccccacccc caattttgta tttatttatt ttttaattat tttgtgcagc      420 gatggggcg ggggggggg ggggcgcgc gccaggcggg gcgggcggg gcaggggcg           480 gggcggggcg aggcggagag gtgcggcggc agccaatcag agcggcgcgc tccgaaagtt      540 tcctttatg gcgaggcggc ggcggcggcg ccctataaa aagcgaagcg cgcggcgggc        600
ggatccgttt aaacggctcg catctctcct tcacgcgccc gccgcctac ctgaggccgc       660 catccacgcc ggttgagtcg cgttctgccg cctcccgcct gtggtgcctc ctgaactgcg      720
tccgccgtct aggtaagttt aaagctcagg tcgagaccgg gcctttgtcc ggcgctccct     780
tggagcctac ctagactcag ccggctctcc acgctttgcc tgaccctgct tgctcaactc     840
tacgtctttg tttcgttttc tgttctgcgc cgttacagat c                        881
```

<210> SEQ ID NO 22
<211> LENGTH: 1266
<212> TYPE: DNA
<213> ORGANISM: Artificial Sequence
<220> FEATURE:
<223> OTHER INFORMATION: CMV-bActine-U2

<400> SEQUENCE: 22

```
gcgttacata acttacggta aatggcccgc ctggctgacc gcccaacgac ccccgcccat      60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tggtcgaggt gagcccacg ttctgcttca ctctccccat    360
ctcccccccc tccccacccc caattttgta tttatttatt ttttaattat tttgtgcagc   420 gatggggcg ggggggggg ggggcgcgc gccaggcggg gcgggcggg gcaggggcg        480 gggcggggcg aggcggagag gtgcggcggc agccaatcag agcggcgcgc tccgaaagtt   540 tcctttatg gcgaggcggc ggcggcggcg ccctataaa aagcgaagcg cgcggcgggc     600
ggatccgttt aaacagagta atgacatggt tccttccatc ctccaaaggt gaccaataat   660
agtttgtaag tatcattatg aactaatgaa ttttcaacat atttgatata tttcaatcca   720
ttgccatcat tgttcttatc gatatttgag ttggctcact ttgccagtaa gagtctattc   780
aaattggctt ctgagtccat ttgacacaac acctttgatc tttgacagtt ccttggttt    840 taggtgctag atgatttctc aggctcacct tagacatttc ctgccacaga cttagaatca   900
gccatttctc taaggaccct gattccattt catgagaaat gatagagacc acaatcaaaa   960
caagtcatga atttatactg atattttcaa ttcaaattaa agatgaggtt tttgctaaat  1020
ttttttgagt ttatatttgt atgtcttatg ctgaaaaatc ttgtttccta attagtaaca  1080
taattattca tttgatgggt aaatatttta gggccgattc tttggtttta tagccaagat  1140
accctgttga taaagtcttg tgggagcaat tataagactg gcttattttg aagcttttta  1200
aaaaagacat ccttacctgt tttaactgta gattatatta acttaaatag gtacagccca  1260
cgcttg                                                            1266
```

<210> SEQ ID NO 23

```
<211> LENGTH: 927
<212> TYPE: DNA
<213> ORGANISM: Artificial Sequence
<220> FEATURE:
<223> OTHER INFORMATION: CMV-bActine-U3

<400> SEQUENCE: 23
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg gtcgcgaca tggtcgaggt gagcccacg ttctgcttca ctctccccat    360
ctcccccccc tccccacccc caattttgta tttatttatt ttttaattat tttgtgcagc   420
gatggggcg ggggggggg ggggcgcgc gccaggcggg gcgggcggg gcgaggggcg       480
gggcggggcg aggcggagag gtgcggcggc agccaatcag agcggcgcgc tccgaaagtt   540
tcctttatg gcgaggcggc ggcggcggcg gccctataaa aagcgaagcg cgcggcgggc   600
ggatccgttt aacgctggtg gtagggatg agggaggag gggcattgtg atgtacaggg    660
ctgctctgtg agatcaaggg tctcttaagg gtgggagctg gggcagggac tacgagagca   720
gccagatggg ctgaaagtgg aactcaaggg gtttctggca cctacctacc tgcttccgc    780
tgggggtgg ggagttggcc cagagtctta agattggggc agggtggaga ggtgggctct   840
tcctgcttcc cactcatctt atagctttct ttccccagat ccgaattcga gatccaaacc   900
aaggaggaaa ggatatcaca gaggaga                                      927

<210> SEQ ID NO 24
<211> LENGTH: 1547
<212> TYPE: DNA
<213> ORGANISM: Artificial Sequence
<220> FEATURE:
<223> OTHER INFORMATION: CMV-bActine-U1U2

<400> SEQUENCE: 24
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg gtcgcgaca tggtcgaggt gagcccacg ttctgcttca ctctccccat    360
ctcccccccc tccccacccc caattttgta tttatttatt ttttaattat tttgtgcagc   420
gatggggcg ggggggggg ggggcgcgc gccaggcggg gcgggcggg gcgaggggcg       480
gggcggggcg aggcggagag gtgcggcggc agccaatcag agcggcgcgc tccgaaagtt   540
tcctttatg gcgaggcggc ggcggcggcg gccctataaa aagcgaagcg cgcggcgggc   600
ggatccgttt aacgctcg catctctcct tcacgcgccc gccgccctac ctgaggccgc    660
catccacgcc ggttgagtcg cgttctgccg cctcccgcct gtggtgcctc ctgaactgcg   720
tccgccgtct aggtaagttt aaagctcagg tcgagaccgg ccttttgtcc ggcgctccct   780
tggagcctac ctagactcag ccggctctcc acgctttgcc tgaccctgct tgctcaactc   840
tacgtctttg tttcgttttc tgttctgcgc cgttacagat cactagtgtt taaacagagt   900
```

| aatgacatgg ttccttccat cctccaaagg tgaccaataa tagtttgtaa gtatcattat | 960 |
| gaactaatga attttcaaca tatttgatat atttcaatcc attgccatca ttgttcttat | 1020 |
| cgatatttga gttggctcac tttgccagta agagtctatt caaattggct tctgagtcca | 1080 |
| tttgacacaa cacctttgat ctttgacagt ttccttggtt ttaggtgcta gatgatttct | 1140 |
| caggctcacc ttagacattt cctgccacag acttagaatc agccatttct ctaaggaccc | 1200 |
| tgattccatt tcatgagaaa tgatagagac cacaatcaaa acaagtcatg aatttatact | 1260 |
| gatattttca attcaaatta aagatgaggt ttttgctaaa ttttttttgag tttatatttg | 1320 |
| tatgtcttat gctgaaaaat cttgtttcct aattagtaac ataattattc atttgatggg | 1380 |
| taaatatttt agggccgatt ctttggtttt atagccaaga taccctgttg ataaagtctt | 1440 |
| gtgggagcaa ttataagact ggcttatttt gaagcttttt aaaaaagaca tccttacctg | 1500 |
| ttttaactgt agattatatt aacttaaata ggtacagccc acgcttg | 1547 |

<210> SEQ ID NO 25
<211> LENGTH: 1205
<212> TYPE: DNA
<213> ORGANISM: Artificial Sequence
<220> FEATURE:
<223> OTHER INFORMATION: CMV-bActine-U1U3

<400> SEQUENCE: 25

| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tggtcgaggt gagccccacg ttctgcttca ctctccccat | 360 |
| ctccccccc tccccacccc caattttgta tttatttatt ttttaattat tttgtgcagc | 420 |
| gatggggcg gggggggggg ggggcgcgc gccaggcggg gcgggcggg gcgaggggcg | 480 |
| gggcggggcg aggcggagag gtgcggcggc agccaatcag agcggcgcgc tccgaaagtt | 540 |
| tcctttatg gcgaggcggc ggcggcggcg gccctataaa aagcgaagcg cgcggcgggc | 600 |
| ggatccgttt aaacgctcg catctctcct tcacgcgccc gccgcccta ctgaggccgc | 660 |
| catccacgcc ggttgagtcg cgttctgccg cctcccgcct gtggtgcctc ctgaactgcg | 720 |
| tccgccgtct aggtaagttt aaagctcagg tcgagaccgg ccttttgtcc ggcgctccct | 780 |
| tggagcctac ctagactcag ccggctctcc acgctttgcc tgaccctgct tgctcaactc | 840 |
| tacgtctttg tttcgttttc tgttctgcgc cgttacagat cactagttaa cgctggtggg | 900 |
| tagggatgag ggagggaggg gcattgtgat gtacagggct gctctgtgag atcaagggtc | 960 |
| tcttaagggt gggagctggg gcagggacta cgagagcagc cagatgggct gaaagtggaa | 1020 |
| ctcaaggggt ttctggcacc tacctacctg cttcccgctg gggggtgggg agttggccca | 1080 |
| gagtcttaag attggggcag ggtggagagg tgggctcttc ctgcttccca ctcatcttat | 1140 |
| agctttcttt ccccagatcc gaattcgaga tccaaaccaa ggaggaaagg atatcacaga | 1200 |
| ggaga | 1205 |

<210> SEQ ID NO 26
<211> LENGTH: 1590
<212> TYPE: DNA

<213> ORGANISM: Artificial Sequence
<220> FEATURE:
<223> OTHER INFORMATION: CMV-bActine-U2U3

<400> SEQUENCE: 26

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tggtcgaggt gagccccacg ttctgcttca ctctccccat     360
ctccccccc ccccaccccc caattttgta tttatttatt ttttaattat tttgtgcagc      420
gatggggcg ggggggggg ggggcgcgc gccaggcggg gcgggcggg gcgaggggcg         480
gggcggggcg aggcggagag gtgcggcggc agccaatcag agcggcgcgc tccgaaagtt     540
tccttttatg gcgaggcggc ggcggcggcg gccctataaa aagcgaagcg cgcggcgggc     600
ggatccgttt aaacagagta atgacatggt tccttccatc ctccaaaggt gaccaataat     660
agtttgtaag tatcattatg aactaatgaa ttttcaacat atttgatata ttcaatcca     720
ttgccatcat tgttcttatc gatatttgag ttggctcact tgccagtaa gagtctattc     780
aaattggctt ctgagtccat ttgacacaac acctttgatc tttgacagtt tccttggttt    840
taggtgctag atgatttctc aggctcacct tagacatttc ctgccacaga cttagaatca   900
gccatttctc taaggaccct gattccattt catgagaaat gatagagacc acaatcaaaa   960
caagtcatga atttatactg atatttttcaa ttcaaattaa agatgaggtt tttgctaaat  1020
ttttttgagt ttatatttgt atgtcttatg ctgaaaaatc ttgtttccta attagtaaca   1080
taattattca tttgatgggt aaatatttta gggccgattc ttttggtttta tagccaagat   1140
accctgttga taaagtcttg tgggagcaat tataagactg gcttatttg aagctttta    1200
aaaaagacat ccttacctgt tttaactgta gattatatta acttaaatag gtacagccca  1260
cgcttgacta gttaacgctg gtgggtaggg atgagggagg gagggcatt gtgatgtaca   1320
gggctgctct gtgagatcaa gggtctctta agggtgggag ctggggcagg gactacgaga   1380
gcagccagat gggctgaaag tggaactcaa ggggtttctg gcacctacct acctgcttcc  1440
cgctgggggg tggggagttg gcccagagtc ttaagattgg ggcagggtgg agaggtgggc   1500
tcttcctgct tcccactcat cttatagctt tctttcccca gatccgaatt cgagatccaa  1560
accaaggagg aaaggatatc acagaggaga                                    1590
```

<210> SEQ ID NO 27
<211> LENGTH: 1871
<212> TYPE: DNA
<213> ORGANISM: Artificial Sequence
<220> FEATURE:
<223> OTHER INFORMATION: CMV-bActine-U1U2U3

<400> SEQUENCE: 27

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
```

```
ccatggcccg ggtcgcgaca tggtcgaggt gagccccacg ttctgcttca ctctccccat      360 ctccccccc  tccccacccc caatttttgta tttatttatt ttttaattat tttgtgcagc     420 gatggggcg  gggggggggg ggggcgcgc  gccaggcggg gcgggcggg  gcgaggggcg      480 gggcggggc  aggcggagag gtgccggcgg agccaatcag agcggcgcgc tccgaaagtt      540 tcctttttatg gcgaggcggc ggcggcggcg gccctataaa aagcgaagcg cgcggcgggc    600
ggatccgttt aaacggctcg catctctcct tcacgcgccc gccgcccctac ctgaggccgc    660 catccacgcc ggttgagtcg cgttctgccg cctcccgcct gtggtgcctc ctgaactgcg     720
tccgccgtct aggtaagttt aaagctcagg tcgagaccgg gccttttgtcc ggcgctccct   780 tggagcctac ctagactcag ccggctctcc acgctttgcc tgaccctgct tgctcaactc     840
tacgtctttg tttcgttttc tgttctgcgc cgttacagat cactagtgtt taaacagagt     900
aatgacatgg ttccttccat cctccaaagg tgaccaataa tagtttgtaa gtatcattat    960
gaactaatga attttcaaca tatttgatat atttcaatcc attgccatca ttgttcttat    1020
cgatatttga gttggctcac tttgccagta agagtctatt caaattggct tctgagtcca    1080
tttgacacaa cacctttgat ctttgacagt ttccttggtt ttaggtgcta gatgatttct    1140
caggctcacc ttagacattt cctgccacag acttagaatc agccatttct ctaaggaccc    1200
tgattccatt tcatgagaaa tgatagagac cacaatcaaa acaagtcatg aatttatact    1260 gatatttttca attcaaatta aagatgaggt ttttgctaaa ttttttttgag tttatatttg  1320 tatgtcttat gctgaaaaat cttgttttcct aattagtaac ataattattc atttgatggg    1380 taaatattttt agggccgatt ctttggtttt atagccaaga taccctgttg ataaagtctt   1440
gtgggagcaa ttataagact ggcttatttt gaagctttt aaaaaagaca tccttacctg     1500
ttttaactgt agattatatt aacttaaata ggtacagccc acgcttgact agttaacgct    1560
ggtgggtagg gatgagggag ggaggggcat tgtgatgtac agggctgctc tgtgagatca    1620
agggtctctt aagggtggga gctggggcag ggactacgag agcagccaga tgggctgaaa   1680
gtggaactca aggggtttct ggcacctacc tacctgcttc ccgctggggg gtggggagtt    1740
ggcccagagt cttaagattg gggcagggtg gagaggtggg ctcttcctgc ttcccactca   1800
tcttatagct ttctttcccc agatccgaat tcgagatcca aaccaaggag gaaaggatat    1860
cacagaggag a                                                          1871
```

<210> SEQ ID NO 28
<211> LENGTH: 1643
<212> TYPE: DNA
<213> ORGANISM: Artificial Sequence
<220> FEATURE:
<223> OTHER INFORMATION: CMV-CDK9-EF1

<400> SEQUENCE: 28

```
gcgttacata acttacggta aatggcccgc ctggctgacc gcccaacgac ccccgcccat       60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt    240
acatgacctt atgggacttt cctacttggc agtacatcta cgtattagtc atcgctatta     300
ccatggcccg gtcgcgaca tgcagcggga cgcgccaccc cgagcccag ctccggcgcc       360 ccggctcccc gcgccccga tcgggccgc cgctagtagt ggcggcggcg gaggcggggg       420
```

| | |
|---|---:|
| cagcggcggc ggcggcggag gcgcctctgc agctccggct ccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccacta gtcgggtttg ccgccagaac acaggtaagt gccgtgtgtg | 720 |
| gttcccgcgg gcctggcctc tttacgggtt atggcccttg cgtgccttga attacttcca | 780 |
| cctggctgca gtacgtgatt cttgatcccg agcttcgggt tggaagtggg tgggagagtt | 840 |
| cgaggccttg cgcttaagga gccccttcgc ctcgtgcttg agttgaggcc tggcctgggc | 900 |
| gctggggccg ccgcgtgcga atctggtggc accttcgcgc ctgtctcgct gctttcgata | 960 |
| agtctctagc catttaaaat ttttgatgac ctgctgcgac gcttttttc tggcaagata | 1020 |
| gtcttgtaaa tgcgggccaa gatctgcaca ctggtatttc ggttttggg gccgcgggcg | 1080 |
| gcgacgggc ccgtgcgtcc cagcgcacat gttcggcgag gcggggcctg cgagcgcggc | 1140 |
| caccgagaat cggacggggg tagtctcaag ctggccggcc tgctctggtg cctggcctcg | 1200 |
| cgccgccgtg tatcgccccg ccctgggcgg caaggctggc ccggtcggca ccagttgcgt | 1260 |
| gagcggaaag atggccgctt cccggccctg ctgcaggagg ctcaaaatgg aggacgcggc | 1320 |
| gctcgggaga gcgggcgggt gagtcaccca cacaaaggaa aagggccttt ccgtcctcag | 1380 |
| ccgtcgcttc atgtgactcc acggagtacc gggcgccgtc caggcacctc gattagttct | 1440 |
| cgagcttttg gagtacgtcg tctttaggtt gggggagggg gttttatgcg atggagtttc | 1500 |
| cccacactga gtgggtggag actgaagtta ggccagcttg gcacttgatg taattctcct | 1560 |
| tggaatttgc ccttttttgag tttggatctt ggttcattct caagcctcag acagtggttc | 1620 |
| aaagtttttt tcttccattt cag | 1643 |

<210> SEQ ID NO 29
<211> LENGTH: 1051
<212> TYPE: DNA
<213> ORGANISM: Artificial Sequence
<220> FEATURE:
<223> OTHER INFORMATION: CMV-CDK9-mROSA

<400> SEQUENCE: 29

| | |
|---|---:|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccacta gttcagagag cctcggctag tagggggatc gggactctgg | 720 |
| cgggagggcg gcttggtgcg tttgcgggga tgggcggccg cggcaggccc tccgagcgtg | 780 |
| gtggagccgt tctgtgagac agccgggtac gagtcgtgac gctggaaggg gcaagcgggt | 840 |

```
ggtgggcagg aatgcggtcc gccctgcagc aaccggaggg ggaggagaa gggagcggaa      900 aagtctccac cggacgcggc catggctcgg ggggggggg gcagcggagg agcgcttccg      960
gccgacgtct cgtcgctgat tggcttcttt cctcccgcc gtgtgtgaaa acacaattgt     1020
actaaccttc ttctctttcc tctcctgaca g                                    1051
```

<210> SEQ ID NO 30
<211> LENGTH: 1918
<212> TYPE: DNA
<213> ORGANISM: Artificial Sequence
<220> FEATURE:
<223> OTHER INFORMATION: CMV-CDK9-hROSA

<400> SEQUENCE: 30

```
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg gtcgcgaca tgcagcggga cgcgccaccc cgagcccag ctccggcgcc       360 ccggctcccc gcgccccga tcggggccgc cgctagtagt ggcggcggcg gaggcggggg       420
cagcggcggc ggcggcggag gcgcctctgc agctccggct cccctggcc tctcgggaac      480 tacaagtccc aggggcctg gcggtgggcg gcgggcggaa gaggcggggt cggcgccgcg      540
aggccggaag tggccgtgga ggcggaagtg gcgcggccgc ggaggggcct ggagtgcggc      600
ggcggcggga cccggagcag gagcggcggc agcagcgact ggggcggcg gcggcgcgtt      660 ggaggcggcc ggatccacta gtctcagaga gcctcggcta ggtaggggag cggaactctg      720
gtgggagggg aggtgcggtg cactggggg atgggtggct agggggccg tctggtggct       780 tgcggggtt gccttcccg tgggaagtcg ggaacataat gtttgttacg ttgggaggga      840
aaggggtggc tggatgcagg cgggaggag gcccgccctg cggcaaccgg aggggaggg      900 agaagggagc ggaaaatgct cgaaaccgga cggagccatt gctctcgcag agggaggagc      960
gcttccggct agcctcttgt cgccgattgg ccgtttctcc tcccgccgtg tgtgaaaaca     1020
caaatggcgt attctggttg gagtaaagct cctgtcagtt acaccgtcgg gagtacgcag     1080
ccgcttagcg actctcgcgt tgcccctgg gtggggcggg taggtaggtg gggtgtagag     1140
atgctgggtg tgcgggcgcg gccggcctcc tgcggcggga gggagggtc agtgaaattg      1200 gctctggcgc gggcgtcctc ccaccctccc cttccttcgg gggagtcggt ttacccgccg     1260
cctgcttgtc ttcgacacct gattggctgt cgaagctgtg gaccgggcc cttgctactg     1320 gctcgagtct cacatgagcg aaaccactgc gcggggcgcg ggggtggcgg ggaggcgggc      1380
gttggtacgg tcctccccga ggccgagcgc cgcagtgtct ggccccgcgc ccctgcgcaa     1440
cgtggcagga agcgcgcgct ggaggcgggg gcgggctgcc ggccgagact tctggatggc     1500
ggcggccgcg gctccgcccc gggttccac cgcctgaagg gcgagacaag cccgacctgc      1560
tacaggcact cgtgggggtg ggggaggagc ggggtcggt ccggctggtt tgtgggtggg     1620
aggcgcttgt tctccaaaaa ccggcgcgag ctgcaatcct gagggagctg cggtggagga     1680
ggtggagaga aggccgcacc cttctgggca ggggagggg agtgccgcaa tacctttatg     1740
ggagttcttt gctgcctccc gtcttgtaag gaccgccctg ggcctggaag aagcccctccc     1800
```

| tcctttcctc ctcgcgtgat ctcgtcatcg cctccatgtc gagtcgcttc tcgattatgg | 1860 |
| gcgggattct tttgcctaga caattgtact aaccttcttc tctttcctct cctgacag | 1918 |

<210> SEQ ID NO 31
<211> LENGTH: 1573
<212> TYPE: DNA
<213> ORGANISM: Artificial Sequence
<220> FEATURE:
<223> OTHER INFORMATION: CMV-bActine-EF1

<400> SEQUENCE: 31

| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tggtcgaggt gagccccacg ttctgcttca ctctccccat | 360 |
| ctccccccc tccccacccc caattttgta tttatttatt ttttaattat tttgtgcagc | 420 |
| gatggggcg gggggggggg gggggcgcgc gccaggcggg gcggggcggg gcgaggggcg | 480 |
| gggcggggcg aggcggagag gtgcggcggc agccaatcag agcggcgcgc tccgaaagtt | 540 |
| tccttttatg gcgaggcggc ggcggcggcg ccctataaa aagcgaagcg cgcggcgggc | 600 |
| ggatccacta gtcgggtttg ccgccagaac acaggtaagt gccgtgtgtg gttcccgcgg | 660 |
| gcctggcctc tttacgggtt atggcccttg cgtgccttga attacttcca cctggctgca | 720 |
| gtacgtgatt cttgatcccg agcttcgggt tggaagtggg tgggagagtt cgaggccttg | 780 |
| cgcttaagga gccccttcgc ctcgtgcttg agttgaggcc tggcctgggc gctggggccg | 840 |
| ccgcgtgcga atctggtggc accttcgcgc ctgtctcgct gctttcgata agtctctagc | 900 |
| catttaaaat ttttgatgac ctgctgcgac gcttttttt tggcaagata gtcttgtaaa | 960 |
| tgcgggccaa gatctgcaca ctggtatttc ggttttgggg gccgcgggcg gcgacggggc | 1020 |
| ccgtgcgtcc cagcgcacat gttcggcgag gcggggcctg cgagcgcggc caccgagaat | 1080 |
| cggacggggg tagtctcaag ctggccggcc tgctctggtg cctggcctcg cgccgccgtg | 1140 |
| tatcgccccg ccctgggcgg caaggctggc ccggtcggca ccagttgcgt gagcggaaag | 1200 |
| atggccgctt cccggccctg ctgcagggag ctcaaaatgg aggacgcggc gctcgggaga | 1260 |
| gcgggcgggt gagtcaccca cacaaaggaa aagggccttt ccgtcctcag ccgtcgcttc | 1320 |
| atgtgactcc acggagtacc gggcgccgtc caggcacctc gattagttct cgagcttttg | 1380 |
| gagtacgtcg tctttaggtt ggggggaggg gttttatgcg atggagtttc cccacactga | 1440 |
| gtgggtggag actgaagtta ggccagcttg gcacttgatg taattctcct tggaatttgc | 1500 |
| ccttttgag tttggatctt ggttcattct caagcctcag acagtggttc aaagttttt | 1560 |
| tcttccattt cag | 1573 |

<210> SEQ ID NO 32
<211> LENGTH: 981
<212> TYPE: DNA
<213> ORGANISM: Artificial Sequence
<220> FEATURE:
<223> OTHER INFORMATION: CMV-bActine-mROSA

<400> SEQUENCE: 32

| gcgttacata acttacggta aatggcccgc ctggctgacc gcccaacgac ccccgcccat | 60 |

```
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tggtcgaggt gagccccacg ttctgcttca ctctccccat      360 ctccccccc tccccacccc caattttgta tttatttatt ttttaattat tttgtgcagc       420 gatggggcg ggggggggg ggggcgcgc gccaggcggg gcgggcggg gcgaggggcg         480 gggcggggcg aggcggagag gtgcggcggc agccaatcag agcggcgcgc tccgaaagtt      540
tccttttatg gcgaggcggc ggcggcggcg gccctataaa aagcgaagcg cgcggcgggc      600
ggatccacta gttcagagag cctcggctag gtaggggatc gggactctgg cgggaggggcg     660 gcttggtgcg tttgcgggga tgggcggccg cggcaggccc tccgagcgtg gtggagccgt     720
tctgtgagac agccgggtac gagtcgtgac gctggaaggg gcaagcgggt ggtgggcagg     780
aatgcggtcc gccctgcagc aaccggaggg ggagggagaa gggagcggaa aagtctccac     840
cggacgcggc catggctcgg ggggggggg gcagcggagg agcgcttccg gccgacgtct      900
cgtcgctgat tggcttcttt tcctcccgcc gtgtgtgaaa acacaattgt actaaccttc      960
ttctctttcc tctcctgaca g                                               981

<210> SEQ ID NO 33
<211> LENGTH: 1848
<212> TYPE: DNA
<213> ORGANISM: Artificial Sequence
<220> FEATURE:
<223> OTHER INFORMATION: CMV-bActine-hROSA

<400> SEQUENCE: 33
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tggtcgaggt gagccccacg ttctgcttca ctctccccat      360 ctccccccc tccccacccc caattttgta tttatttatt ttttaattat tttgtgcagc       420 gatggggcg ggggggggg ggggcgcgc gccaggcggg gcgggcggg gcgaggggcg         480 gggcggggcg aggcggagag gtgcggcggc agccaatcag agcggcgcgc tccgaaagtt      540
tccttttatg gcgaggcggc ggcggcggcg gccctataaa aagcgaagcg cgcggcgggc      600
ggatccacta gtctcagaga gcctcggcta ggtaggggag cggaactctg gtgggagggg     660
aggtgcggtg cactgggggg atgggtggct aggggggccg tctggtggct tgcggggggtt    720 gcctttcccg tgggaagtcg ggaacataat gtttgttacg ttgggaggga aaggggtggc    780
tggatgcagg cgggagggag gcccgccctg cggcaaccgg agggggaggg agaagggagc     840
ggaaaatgct cgaaaccgga cggagccatt gctctcgcag agggaggagc gcttccggct     900
agcctcttgt cgccgattgg ccgtttctcc tcccgccgtg tgtgaaaaca caaatggcgt     960
attctggttg gagtaaagct cctgtcagtt acaccgtcgg gagtacgcag ccgcttagcg    1020
actctcgcgt tgcccctgg gtggggcggg taggtaggtg gggtgtagag atgctgggtg     1080
```

```
tgcgggcgcg gccggcctcc tgcggcggga ggggagggtc agtgaaattg gctctggcgc    1140
gggcgtcctc ccaccctccc cttccttcgg gggagtcggt ttacccgccg cctgcttgtc    1200
ttcgacacct gattggctgt cgaagctgtg ggaccgggcc cttgctactg gctcgagtct    1260
cacatgagcg aaaccactgc gcggggcgcg ggggtggcgg ggaggcgggc gttggtacgg    1320
tcctccccga ggccgagcgc cgcagtgtct ggccccgcgc ccctgcgcaa cgtggcagga    1380
agcgcgcgct ggaggcgggg gcgggctgcc ggccgagact tctggatggc ggcggccgcg    1440
gctccgcccc gggttcccac cgcctgaagg gcgagacaag cccgacctgc tacaggcact    1500
cgtgggggtg ggggaggagc ggggtcggt ccggctggtt tgtgggtggg aggcgcttgt    1560
tctccaaaaa ccggcgcgag ctgcaatcct gagggagctg cggtggagga ggtggagaga    1620
aggccgcacc cttctgggca gggggagggg agtgccgcaa tacctttatg ggagttcttt    1680
gctgcctccc gtcttgtaag gaccgccctg ggcctggaag aagccctccc tcctttcctc    1740
ctcgcgtgat ctcgtcatcg cctccatgtc gagtcgcttc tcgattatgg gcgggattct    1800
tttgcctaga caattgtact aaccttcttc tctttcctct cctgacag                 1848

<210> SEQ ID NO 34
<211> LENGTH: 1918
<212> TYPE: DNA
<213> ORGANISM: Artificial Sequence
<220> FEATURE:
<223> OTHER INFORMATION: CMV-CDK9-U1-EF1

<400> SEQUENCE: 34
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag gcgcctctgc agctccggct ccccctggcc tctcgggaac     480
tacaagtccc aggggcctg gcggtggcg gcgggcggaa gaggcggggt cggcgccgcg      540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg cctttgtcc    840 ggcgctccct tggagcctac ctagactcag ccggctctcc acgctttgcc tgaccctgct    900
tgctcaactc tacgtctttg tttcgttttc tgttctgcgc cgttacagat cactagtcgg    960
gtttgccgcc agaacacagg taagtgccgt gtgtggttcc cgcgggcctg gcctctttac    1020
gggttatggc ccttgcgtgc cttgaattac ttccacctgg ctgcagtacg tgattcttga    1080
tcccgagctt cggggttggaa gtgggtggga gagttcgagg ccttgcgctt aaggagcccc    1140
ttcgcctcgt gcttgagttg aggcctggcc tgggcgctgg ggccgccgcg tgcgaatctg    1200
gtggcacctt cgcgcctgtc tcgctgcttt cgataagtct ctagccattt aaaatttttg    1260
atgacctgct gcgacgcttt ttttctggca agatagtctt gtaaatgcgg gccaagatct    1320
```

```
gcacactggt atttcggttt ttggggccgc gggcggcgac ggggcccgtg cgtcccagcg    1380
cacatgttcg gcgaggcggg gcctgcgagc gcggccaccg agaatcggac gggggtagtc    1440
tcaagctggc cggcctgctc tggtgcctgg cctcgcgccg ccgtgtatcg ccccgccctg    1500
ggcggcaagg ctggcccggt cggcaccagt tgcgtgagcg gaaagatggc cgcttcccgg    1560
ccctgctgca gggagctcaa aatggaggac gcggcgctcg ggagagcggg cgggtgagtc    1620
acccacacaa aggaaaaggg cctttccgtc ctcagccgtc gcttcatgtg actccacgga    1680
gtaccgggcg ccgtccaggc acctcgatta gttctcgagc ttttggagta cgtcgtcttt    1740
aggttggggg gagggttttt atgcgatgga gtttccccac actgagtggg tggagactga    1800
agttaggcca gcttggcact tgatgtaatt ctccttggaa tttgcccttt ttgagtttgg    1860
atcttggttc attctcaagc ctcagacagt ggttcaaagt ttttttcttc catttcag     1918

<210> SEQ ID NO 35
<211> LENGTH: 1326
<212> TYPE: DNA
<213> ORGANISM: Artificial Sequence
<220> FEATURE:
<223> OTHER INFORMATION: CMV-CDK9-U1-mROSA

<400> SEQUENCE: 35
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc     360 ccggctcccc gcgccccga tcggggccgc cgctagtagt ggcggcggcg gaggcggggg     420
cagcggcggc ggcggcggag gcgcctctgc agctccggct ccccctggcc tctcgggaac     480
tacaagtccc agggggcctg gcggtgggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacggctcg catctctcct tcacgcgccc gccgccctac     720
ctgaggccgc catccacgcc ggttgagtcg cgttctgccg cctcccgcct gtggtgcctc     780
ctgaactgcg tccgccgtct aggtaagttt aaagctcagg tcgagaccgg cctttgtcc     840 ggcgctccct tggagcctac ctagactcag ccggctctcc acgctttgcc tgaccctgct     900
tgctcaactc tacgtctttg tttcgttttc tgttctgcgc cgttacagat cactagttca     960
gagagcctcg gctaggtagg ggatcgggac tctggcggga gggcggcttg gtgcgtttgc    1020
ggggatgggc ggccgcggca ggccctccga gcgtggtgga gccgttctgt gagacagccg    1080
ggtacgagtc gtgacgctgg aagggcaag cgggtggtgg gcaggaatgc ggtccgccct    1140
gcagcaaccg gaggggagg gagaagggag cggaaaagtc tccaccggac gcggccatgg    1200
ctcggggggg gggggcagc ggaggagcgc ttccggccga cgtctcgtcg ctgattggct    1260
tcttttcctc ccgccgtgtg tgaaaacaca attgtactaa ccttcttctc tttcctctcc    1320
tgacag                                                                1326

<210> SEQ ID NO 36
```

<211> LENGTH: 2193
<212> TYPE: DNA
<213> ORGANISM: Artificial Sequence
<220> FEATURE:
<223> OTHER INFORMATION: CMV-CDK9-U1-hROSA

<400> SEQUENCE: 36

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360
ccggctcccc gcgcccccga tcgggccgc cgctagtagt ggcggcggcg gaggcggggg      420
cagcggcggc ggcggcggag cgcctctgc agctccggct cccctggcc tctcgggaac       480
tacaagtccc agggggcctg gcggtgggcg gcggcggaa gaggcgggt cggcgccgcg       540
aggccggaag tggccgtgga ggcggaagtg gcgcggccgc ggaggggcct ggagtgcggc     600
ggcggcggga cccggagcag gagcggcggc agcagcgact ggggcggcg gcggcgcgtt      660
ggaggcggcc ggatccgttt aaacggctcg catctctcct tcacgcgccc gccgcctac     720
ctgaggccgc catccacgcc ggttgagtcg cgttctgccg cctcccgcct gtggtgcctc     780
ctgaactgcg tccgccgtct aggtaagttt aaagctcagg tcgagaccgg gcctttgtcc     840
ggcgctccct tggagcctac ctagactcag ccggctctcc acgctttgcc tgaccctgct     900
tgctcaactc tacgtctttg tttcgttttc tgttctgcgc cgttacagat cactagtctc     960
agagagcctc ggctaggtag gggagcggaa ctctggtggg aggggaggtg cggtgcactg    1020
gggggatggg tggctagggg ggccgtctgg tggcttgcgg gggttgcctt tcccgtggga    1080
agtcgggaac ataatgtttg ttacgttggg agggaagg gtggctggat gcaggcggga     1140
gggaggcccg ccctgcggca accggagggg gagggagaag ggagcggaaa atgctcgaaa    1200
ccggacggag ccattgctct cgcagaggga ggagcgcttc cggctagcct cttgtcgccg    1260
attggccgtt tctcctcccg ccgtgtgtga aaacacaaat ggcgtattct ggttggagta    1320
aagctcctgt cagttacacc gtcgggagta cgcagccgct tagcgactct cgcgttgccc    1380
cctgggtggg gcgggtaggt aggtgggtg tagagatgct gggtgtgcgg gcgcggccgg     1440
cctcctgcgg cggagggga gggtcagtga aattggctct ggcgcgggcg tcctcccacc     1500
ctcccttcc ttcggggag tcggtttacc cgccgcctgc ttgtcttcga cacctgattg      1560
gctgtcgaag ctgtgggacc gggcccttgc tactggctcg agtctcacat gagcgaaacc    1620
actgcgcggg gcgcggggt ggcggggagg cgggcgttgg tacggtcctc cccgaggccg     1680
agcgccgcag tgtctggccc cgcgcccctg cgcaacgtgg caggaagcgc gcgctggagg    1740
cggggcggg ctgccggccg agacttctgg atggcggcgg ccgcggctcc gccccgggtt     1800
cccaccgcct gaagggcgag acaagcccga cctgctacag gcactcgtgg gggtgggga    1860
ggagcggggg tcgtccggc tggtttgtgg gtggaggcg cttgttctcc aaaaaccggc     1920
gcgagctgca atcctgaggg agctgcggtg gaggaggtgg agagaaggcc gcacccttct    1980
gggcaggggg agggagtgc cgcaataacct ttatgggagt tctttgctgc ctcccgtctt    2040
gtaaggaccg ccctgggcct ggaagaagcc ctccctcctt tcctcctcgc gtgatctcgt    2100
catcgcctcc atgtcgagtc gcttctcgat tatgggcggg attcttttgc ctagacaatt    2160
```

```
gtactaacct tcttctcttt cctctcctga cag                                     2193
```

<210> SEQ ID NO 37
<211> LENGTH: 2309
<212> TYPE: DNA
<213> ORGANISM: Artificial Sequence
<220> FEATURE:
<223> OTHER INFORMATION: CMV-CDK9-U2-EF1

<400> SEQUENCE: 37

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc      360
ccggctcccc gcgccccga tcggggccgc cgctagtagt ggcggcggcg gaggcggggg    420
cagcggcggc ggcggcggag gcgcctctgc agctccggct cccccctggcc tctcgggaac    480
tacaagtccc aggggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccacta gtgtttaaac agagtaatga catggttcct tccatcctcc    720
aaaggtgacc aataatagtt tgtaagtatc attatgaact aatgaatttt caacatattt    780
gatatatttc aatccattgc catcattgtt cttatcgata tttgagttgg ctcactttgc    840
cagtaagagt ctattcaaat tggcttctga gtccatttga cacaacacct ttgatctttg    900
acagtttcct tggttttagg tgctagatga tttctcaggc tcaccttaga catttcctgc    960
cacagactta gaatcagcca tttctctaag gaccctgatt ccatttcatg agaaatgata   1020
gagaccacaa tcaaaacaag tcatgaattt atactgatat tttcaattca aattaaagat   1080
gaggttttg ctaaattttt ttgagtttat atttgtatgt cttatgctga aaaatcttgt    1140
ttcctaatta gtaacataat tattcatttg atgggtaaat attttagggc cgattctttg   1200
gttttatagc caagataccc tgttgataaa gtcttgtggg agcaattata agactggctt   1260
attttgaagc ttttttaaaaa agacatcctt acctgtttta actgtagatt atattaactt    1320
aaataggtac agcccacgct tgactagtcg ggtttgccgc cagaacacag gtaagtgccg    1380
tgtgtggttc ccgcgggcct ggcctcttta cgggttatgg cccttgcgtg ccttgaatta    1440
cttccacctg gctgcagtac gtgattcttg atcccgagct tcgggttgga agtgggtggg    1500
agagttcgag gccttgcgct taaggagccc cttcgcctcg tgcttgagtt gaggcctggc    1560
ctgggcgctg gggccgccgc gtgcgaatct ggtggcacct tcgcgcctgt ctcgctgctt    1620
tcgataagtc tctagccatt taaaattttt gatgacctgc tgcgacgctt tttttctggc    1680
aagatagtct tgtaaatgcg ggccaagatc tgcacactgg tatttcggtt tttggggccg    1740
cgggcggcga cggggcccgt gcgtcccagc gcacatgttc ggcgaggcgg ggcctgcgag    1800
cgcggccacc gagaatcgga cgggggtagt ctcaagctgg ccggcctgct ctggtgcctg    1860
gcctcgcgcc gccgtgtatc gccccgccct gggcggcaag gctggcccgg tcggcaccag    1920
ttgcgtgagc ggaaagatgg ccgcttcccg gccctgctgc agggagctca aaatggagga    1980
```

```
cgcggcgctc gggagagcgg gcgggtgagt cacccacaca aaggaaaagg gcctttccgt    2040
cctcagccgt cgcttcatgt gactccacgg agtaccgggc gccgtccagg cacctcgatt    2100
agttctcgag cttttggagt acgtcgtctt taggttgggg ggaggggttt tatgcgatgg    2160
agtttcccca cactgagtgg gtggagacta agttaggcc agcttggcac ttgatgtaat    2220
tctccttgga atttgccctt tttgagtttg gatcttggtt cattctcaag cctcagacag    2280
tggttcaaag ttttttttctt ccatttcag                                    2309
```

<210> SEQ ID NO 38
<211> LENGTH: 1717
<212> TYPE: DNA
<213> ORGANISM: Artificial Sequence
<220> FEATURE:
<223> OTHER INFORMATION: CMV-CDK9-U2-mROSA

<400> SEQUENCE: 38

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360 ccggctcccc gcgccccga tcggggccgc cgctagtagt ggcggcggcg gaggcggggg       420
cagcggcggc ggcggcggag gcgcctctgc agctccggct cccccctggcc tctcgggaac     480 tacaagtccc aggggcctg gcggtgggcg gcgggcggaa gaggcggggt cggcgccgcg      540
aggccggaag tggccgtgga ggcggaagtg gcgcggccgc ggaggggcct ggagtgcggc     600
ggcggcggga cccggagcag gagcggcggc agcagcgact gggggcggcg cggcgcgtt     660 ggaggcggcc ggatccacta gtgtttaaac agagtaatga catggttcct tccatcctcc    720
aaaggtgacc aataatagtt tgtaagtatc attatgaact aatgaatttt caacatattt    780
gatatatttc aatccattgc catcattgtt cttatcgata tttgagttgg ctcactttgc    840
cagtaagagt ctattcaaat tggcttctga gtccatttga cacaacacct ttgatctttg    900
acagtttcct tggttttagg tgctagatga tttctcaggc tcaccttaga catttcctgc    960
cacagactta gaatcagcca tttctctaag gaccctgatt ccatttcatg agaaatgata   1020
gagaccacaa tcaaaacaag tcatgaattt atactgatat tttcaattca aattaaagat   1080 gaggttttg ctaaatttttt ttgagtttat atttgtatgt cttatgctga aaaatcttgt    1140
ttcctaatta gtaacataat tattcatttg atgggtaaat attttagggc cgattctttg    1200
gttttatagc caagatacccc tgttgataaa gtcttgtggg agcaattata agactggctt    1260
attttgaagc ttttttaaaaa agacatcctt acctgtttta actgtagatt atattaactt    1320
aaataggtac agcccacgct tgactagttc agagagcctc ggctaggtag gggatcggga    1380
ctctggcggg agggcggctt ggtgcgtttg cggggatggg cggccgcggc aggccctccg    1440
agcgtggtgg agccgttctg tgagacagcc gggtacgagt cgtgacgctg gaaggggcaa    1500
gcgggtggtg ggcaggaatg cggtccgccc tgcagcaacc ggaggggggag ggagaaggga    1560 gcggaaaagt ctccaccgga cgcggccatg gctcgggggg gggggggcag cggaggagcg    1620
cttccggccg acgtctcgtc gctgattggc ttctttttcct cccgccgtgt gtgaaaacac    1680
aattgtacta accttcttct ctttcctctc ctgacag                              1717
```

<210> SEQ ID NO 39
<211> LENGTH: 2584
<212> TYPE: DNA
<213> ORGANISM: Artificial Sequence
<220> FEATURE:
<223> OTHER INFORMATION: CMV-CDK9-U2-hROSA

<400> SEQUENCE: 39

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360
ccggctcccc gcgccccga tcggggccgc cgctagtagt ggcggcggcg gaggcggggg      420
cagcggcggc ggcggcggag gcgcctctgc agctccggct ccccctggcc tctcgggaac    480
tacaagtccc aggggccctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact ggggcggcg gcggcgcgtt    660
ggaggcggcc ggatccacta gtgtttaaac agagtaatga catggttcct tccatcctcc    720
aaaggtgacc aataatagtt tgtaagtatc attatgaact aatgaatttt caacatattt    780
gatatatttc aatccattgc catcattgtt cttatcgata tttgagttgg ctcactttgc    840
cagtaagagt ctattcaaat tggcttctga gtccatttga cacaacacct ttgatctttg    900
acagtttcct tggttttagg tgctagatga tttctcaggc tcaccttaga catttcctgc    960
cacagactta gaatcagcca tttctctaag gaccctgatt ccatttcatg agaaatgata   1020
gagaccacaa tcaaaacaag tcatgaattt atactgatat tttcaattca aattaaagat   1080
gaggtttttg ctaaattttt ttgagtttat atttgtatgt cttatgctga aaaatcttgt   1140
ttcctaatta gtaacataat tattcatttg atgggtaaat attttagggc cgattctttg   1200
gttttatagc caagatacc tgttgataaa gtcttgtggg agcaattata agactggctt    1260
attttgaagc ttttttaaaaa agacatcctt acctgtttta actgtagatt atattaactt    1320
aaataggtac agcccacgct tgactagtct cagagagcct cggctaggta ggggagcgga    1380
actctggtgg gaggggaggt gcggtgcact ggggggatgg gtggctaggg gggccgtctg    1440
gtggcttgcg ggggttgcct ttcccgtggg aagtcgggaa cataatgttt gttacgttgg    1500
gagggaaagg ggtggctgga tgcagcggg agggaggccc gccctgcggc aaccggaggg    1560
ggagggagaa gggagcggaa aatgctcgaa accggacgga gccattgctc tcgcagaggg    1620
aggagcgctt ccggctagcc tcttgtcgcc gattggccgt ttctcctccc gccgtgtgtg    1680
aaaacacaaa tggcgtattc tggttggagt aaagctcctg tcagttacac cgtcgggagt    1740
acgcagccgc ttagcgactc tcgcgttgcc ccctgggtgg ggcgggtagg taggtggggt    1800
gtagagatgc tgggtgtgcg ggcgcggccg gcctcctgcg gcgggagggg agggtcagtg    1860
aaattggctc tggcgcgggc gtcctcccac cctcccctcc cttcggggga gtcggtttac    1920
ccgccgcctg cttgtcttcg acacctgatt ggctgtcgaa gctgtgggac cgggcccttg    1980
ctactggctc gagtctcaca tgagcgaaac cactgcgcgg ggcgcggggg tggcggggag   2040
```

```
gcgggcgttg gtacggtcct ccccgaggcc gagcgccgca gtgtctggcc ccgcgcccct      2100
gcgcaacgtg gcaggaagcg cgcgctggag gcggggcggg gctgccggcc gagacttctg      2160
gatggcggcg gccgcggctc cgccccgggt tcccaccgcc tgaagggcga gacaagcccg      2220
acctgctaca ggcactcgtg gggtgggg aggagcgggg gtcggtccgg ctggtttgtg        2280
ggtgggaggc gcttgttctc caaaaaccgg cgcgagctgc aatcctgagg gagctgcggt      2340
ggaggaggtg gagagaaggc cgcacccttc tgggcagggg gagggagtg ccgcaatacc       2400 tttatgggag ttctttgctg cctcccgtct tgtaaggacc gccctgggcc tggaagaagc      2460
cctccctcct ttcctcctcg cgtgatctcg tcatcgcctc catgtcgagt cgcttctcga      2520
ttatgggcgg gattctttt cctagacaat tgtactaacc ttcttctctt tcctctcctg       2580
acag                                                                   2584
```

<210> SEQ ID NO 40
<211> LENGTH: 1964
<212> TYPE: DNA
<213> ORGANISM: Artificial Sequence
<220> FEATURE:
<223> OTHER INFORMATION: CMV-CDK9-U3-EF1

<400> SEQUENCE: 40

```
gcgttacata acttacggta aatggcccgc ctggctgacc gcccaacgac ccccgcccat        60
tgacgtcaat aatgacgtat gttcccatag taacgccaat agggactttc cattgacgtc       120
aatgggtgga gtatttacgg taaactgccc acttggcagt acatcaagtg tatcatatgc       180
caagtacgcc ccctattgac gtcaatgacg gtaaatggcc cgcctggcat tatgcccagt       240
acatgacctt atgggacttt cctacttggc agtacatcta cgtattagtc atcgctatta       300
ccatggcccg gtcgcgcaca tgcagcggga cgcgccaccc cgagcccag ctccggcgcc        360 ccggctcccc gcgcccccga tcggggccgc cgctagtagt ggcggcggcg gaggcgggg       420 cagcggcggc ggcggcggag gcgcctctgc agctccggct cccctggcc tctcgggaac       480 tacaagtccc aggggcctg gcggtgggcg gcgggcggaa gaggcgggt cggcgccgcg        540 aggccggaag tggccgtgga ggcggaagtg cgcggccgc ggaggggcct ggagtgcggc       600
ggcggcggga cccggagcag gagcggcggc agcagcgact gggggcggcg cggcgcgtt      660 ggaggcggcc ggatccgttt aacgctggtg ggtaggatg agggagggag gggcattgtg      720
atgtacaggg ctgctctgtg agatcaaggg tctcttaagg gtgggagctg gggcagggac     780
tacgagagca gccagatggg ctgaaagtgg aactcaaggg gttctggca cctacctacc      840 tgcttcccgc tggggggtgg ggagttggcc cagagtctta agattgggc agggtggaga      900 ggtgggctct tcctgcttcc cactcatctt atagctttct ttccccagat ccgaattcga     960
gatccaaacc aaggaggaaa ggatatcaca gaggagagct agtcgggttt gccgccagaa   1020
cacaggtaag tgccgtgtgt ggttcccgcg ggcctggcct cttttacggt tatgccctt    1080 gcgtgccttg aattacttcc acctggctgc agtacgtgat tcttgatccc gagcttcggg    1140
ttggaagtgg gtgggagagt tcgaggcctt gcgcttaagg agccccttcg cctcgtgctt   1200
gagttgaggc ctggcctggg cgctgggcc ccgcgtgcg aatctggtgg caccttcgcg     1260
cctgtctcgc tgctttcgat aagtctctag ccatttaaaa ttttttgatga cctgctgcga    1320 cgctttttt ctggcaagat agtcttgtaa atgcgggcca agatctgcac actggtattt    1380 cggttttgg ggccgcgggc ggcgacgggg ccccgtgcgtc ccagcgcaca tgttcggcga    1440
ggcggggcct gcgagcgcgg ccaccgagaa tcggacgggg gtagtctcaa gctggccggc    1500
```

```
ctgctctggt gcctggcctc gcgccgccgt gtatcgcccc gccctgggcg gcaaggctgg    1560
cccggtcggc accagttgcg tgagcggaaa gatggccgct tcccgccct gctgcaggga    1620 gctcaaaatg gaggacgcgg cgctcggag agcgggcggg tgagtcaccc acacaaagga    1680
aaagggcctt tccgtcctca gccgtcgctt catgtgactc cacggagtac cgggcgccgt    1740
ccaggcacct cgattagttc tcgagctttt ggagtacgtc gtctttaggt tgggggggagg   1800 ggttttatgc gatggagttt ccccacactg agtgggtgga gactgaagtt aggccagctt    1860
ggcacttgat gtaattctcc ttggaatttg cccttttga gtttggatct tggttcattc    1920
tcaagcctca gacagtggtt caaagttttt ttcttccatt tcag                     1964
```

<210> SEQ ID NO 41
<211> LENGTH: 1372
<212> TYPE: DNA
<213> ORGANISM: Artificial Sequence
<220> FEATURE:
<223> OTHER INFORMATION: DMV-CDK9-U3-mROSA

<400> SEQUENCE: 41

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc     360 ccggctcccc gcgccccga tcggggccgc cgctagtagt ggcggcgcg gaggcggggg    420 cagcggcggc ggcggcggag gcgcctctgc agctccggct ccccctggcc tctcgggaac    480
tacaagtccc aggggcctg gcggtggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aacgctggtg ggtagggatg agggagggag gggcattgtg    720
atgtacaggg ctgctctgtg agatcaaggg tctcttaagg gtgggagctg ggcagggac    780 tacgagagca gccagatggg ctgaaagtgg aactcaaggg gtttctggca cctacctacc    840
tgcttcccgc tgggggtgg ggagttggcc cagagtctta agattggggc agggtggaga    900
ggtgggctct tcctgcttcc cactcatctt atagctttct ttccccagat ccgaattcga    960
gatccaaacc aaggaggaaa ggatatcaca gaggagagct agttcagaga gcctcggcta   1020
ggtaggggat cgggactctg gcgggagggc ggcttggtgc gtttgcgggg atgggcggcc   1080
gcggcaggcc ctccgagcgt ggtggagccg ttctgtgaga cagccgggta cgagtcgtga   1140
cgctggaagg ggcaagcggg tggtgggcag gaatgcggtc cgccctgcag caaccggagg   1200
gggagggaga agggagcgga aaagtctcca ccggacgcgg ccatggctcg ggggggggg    1260 ggcagcggag gagcgcttcc ggccgacgtc tcgtcgctga ttggcttctt ttcctcccgc    1320
cgtgtgtgaa aacacaattg tactaacctt cttctctttc ctctcctgac ag            1372
```

<210> SEQ ID NO 42
<211> LENGTH: 2239
<212> TYPE: DNA
<213> ORGANISM: Artificial Sequence
<220> FEATURE:

<223> OTHER INFORMATION: CMV-CDK9-U3-hROSA

<400> SEQUENCE: 42

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360
ccggctcccc gcgcccccga tcggggccgc cgctagtagt ggcggcggcg gaggcggggg     420
cagcggcggc ggcggcggag gcgcctctgc agctccggct cccctggcc tctcgggaac      480
tacaagtccc agggggcctg gcggtgggcg gcgggcggaa gaggcgggt cggcgccgcg      540
aggccggaag tggccgtgga ggcggaagtg gcgcggccgc ggaggggcct ggagtgcggc     600
ggcggcggga cccggagcag gagcggcggc agcagcgact ggggcggcg gcggcgcgtt     660
ggaggcggcc ggatccgttt aacgctggtg gtagggatg agggagggag gggcattgtg     720
atgtacaggg ctgctctgtg agatcaaggg tctcttaagg gtgggagctg ggcagggac     780
tacgagagca gccagatggg ctgaaagtgg aactcaaggg gtttctggca cctacctacc     840
tgcttcccgc tgggggtgg ggagttggcc cagagtctta agattgggc agggtggaga      900
ggtgggctct tcctgcttcc cactcatctt atagctttct tccccagat ccgaattcga     960
gatccaaacc aaggaggaaa ggatatcaca gaggagagct agtctcagag agcctcggct    1020
aggtagggga gcggaactct ggtgggaggg gaggtgcggt gcactggggg gatgggtggc    1080
taggggggcc gtctggtggc ttgcgggggt tgcctttccc gtgggaagtc gggaacataa    1140
tgtttgttac gttgggaggg aaaggggtgg ctggatgcag gcgggaggga ggcccgccct    1200
gcggcaaccg gaggggggagg gagaagggag cggaaaatgc tcgaaaccgg acggagccat    1260
tgctctcgca gagggaggag cgcttccggc tagcctcttg tcgccgattg gccgtttctc    1320
ctcccgccgt gtgtgaaaac acaaatggcg tattctggtt ggagtaaagc tcctgtcagt    1380
tacaccgtcg ggagtacgca gccgcttagc gactctcgcg ttgcccctg ggtggggcgg     1440
gtaggtaggt ggggtgtaga gatgctgggt gtgcgggcgc ggccggcctc ctgcggcggg    1500
agggagggt cagtgaaatt ggctctggcg cgggcgtcct cccacccctcc ccttccttcg    1560
ggggagtcgg tttaccccgcc gcctgcttgt cttcgacacc tgattggctg tcgaagctgt    1620
gggaccgggc ccttgctact ggctcgagtc tcacatgagc gaaaccactg cgcggggcgc    1680
ggggtggcg gggaggcggg cgttggtacg gtcctcccg aggccgagcg ccgcagtgtc      1740
tggccccgcg cccctgcgca acgtggcagg aagcgcgcgc tggaggcggg ggcgggctgc    1800
cggccgagac ttctgatgg cggcggccgc ggctccgccc cgggttccca ccgcctgaag     1860
ggcgagacaa gcccgacctg ctacaggcac tcgtgggggt gggggaggag cggggtcgg     1920
tccggctggt ttgtgggtgg gaggcgcttg ttctccaaaa accggcgcga gctgcaatcc    1980
tgagggagct gcgtggagg aggtggagag aaggccgcac ccttctgggc aggggaggg     2040
gagtgccgca ataccttat gggagttctt tgctgcctcc cgtcttgtaa ggaccgccct     2100
gggcctggaa gaagccctcc ctcctttcct cctcgcgtga tctcgtcatc gcctccatgt    2160
cgagtcgctt ctcgattatg ggcgggattc ttttgcctag acaattgtac taaccttctt    2220
ctctttcctc tcctgacag                                                 2239
```

<210> SEQ ID NO 43
<211> LENGTH: 2584
<212> TYPE: DNA
<213> ORGANISM: Artificial Sequence
<220> FEATURE:
<223> OTHER INFORMATION: CMV-CDK9-U1U2-EF1

<400> SEQUENCE: 43

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tgcagcggga cgcgccaccc cgagcccag ctccggcgcc      360
ccggctcccc gcgcccccga tcggggccgc cgctagtagt ggcggcggcg gaggcggggg     420
cagcggcggc ggcggcggag gcgcctctgc agctccggct ccccctggcc tctcgggaac     480
tacaagtccc aggggggcctg gcggtggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacggctcg catctctcct tcacgcgccc gccgccctac     720
ctgaggccgc catccacgcc ggttgagtcg cgttctgccg cctccgcct gtggtgcctc      780
ctgaactgcg tccgccgtct aggtaagttt aaagctcagg tcgagaccgg gcctttgtcc     840
ggcgctccct tggagcctac ctagactcag ccggctctcc acgctttgcc tgaccctgct     900
tgctcaactc tacgtctttg tttcgttttc tgttctgcgc cgttacagat cactagtgtt     960
taaacagagt aatgacatgg ttccttccat cctccaaagg tgaccaataa tagtttgtaa    1020
gtatcattat gaactaatga ttttcaaca tatttgatat atttcaatcc attgccatca    1080
ttgttcttat cgatatttga gttggctcac tttgccagta aagtctatt caaattggct    1140
tctgagtcca tttgacacaa cacctttgat cttttgacagt ttccttggtt ttaggtgcta    1200
gatgatttct caggctcacc ttagacattt cctgccacag acttagaatc agccatttct    1260
ctaaggaccc tgattccatt tcatgagaaa tgatagagac cacaatcaaa acaagtcatg    1320
aattttatact gatattttca attcaaatta aagatgaggt ttttgctaaa ttttttttgag    1380
tttatatttg tatgtcttat gctgaaaaat cttgttttcct aattagtaac ataattattc    1440
atttgatggg taaatatttt agggccgatt ctttggtttt atagccaaga taccctgttg    1500
ataaagtctt gtgggagcaa ttataagact ggccttatttt gaagcttttt aaaaaagaca    1560
tccttacctg tttaactgt agattatatt aacttaaata ggtacagccc acgcttgact    1620
agtcgggttt gccgccagaa cacaggtaag tgccgtgtgt ggttcccgcg ggcctggcct    1680
ctttacgggt tatggcccctt gcgtgccttg aattacttcc acctggctgc agtacgtgat    1740
tcttgatccc gagcttcggg ttggaagtgg gtgggagagt tcgaggcctt gcgcttaagg    1800
agccccttcg cctcgtgctt gagttgaggc ctggcctggg cgctggggcc gccgcgtgcg    1860
aatctggtgg caccttcgcg cctgtctcgc tgctttcgat aagtctctag ccatttaaaa    1920
ttttttgatga cctgctgcga cgcttttttt ctggcaagat agtcttgtaa atgcgggcca    1980
agatctgcac actggtattt cggttttttgg ggccgcgggc ggcgacgggg cccgtgcgtc    2040
```

| | |
|---|---|
| ccagcgcaca tgttcggcga ggcggggcct gcgagcgcgg ccaccgagaa tcggacgggg | 2100 |
| gtagtctcaa gctggccggc ctgctctggt gcctggcctc gcgccgccgt gtatcgcccc | 2160 |
| gccctgggcg gcaaggctgg cccggtcggc accagttgcg tgagcggaaa gatggccgct | 2220 |
| tcccggccct gctgcaggga gctcaaaatg gaggacgcgg cgctcgggag agcgggcggg | 2280 |
| tgagtcaccc acacaaagga aaagggcctt ccgtcctca gccgtcgctt catgtgactc | 2340 |
| cacggagtac cgggcgccgt ccaggcacct cgattagttc tcgagctttt ggagtacgtc | 2400 |
| gtctttaggt tggggggagg ggttttatgc gatggagttt ccccacactg agtgggtgga | 2460 |
| gactgaagtt aggccagctt ggcacttgat gtaattctcc ttggaatttg ccctttttga | 2520 |
| gtttggatct tggttcattc tcaagcctca gacagtggtt caaagttttt ttcttccatt | 2580 |
| tcag | 2584 |

<210> SEQ ID NO 44
<211> LENGTH: 1992
<212> TYPE: DNA
<213> ORGANISM: Artificial Sequence
<220> FEATURE:
<223> OTHER INFORMATION: CMV-CDK9-U1U2-mROSA

<400> SEQUENCE: 44

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct cccccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg cctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga attttcaaca tatttgatat atttcaatcc attgccatca | 1080 |
| ttgttcttat cgatatttga gttggctcac tttgccagta agagtctatt caaattggct | 1140 |
| tctgagtcca tttgacacaa cacctttgat ctttgacagt ttccttggtt ttaggtgcta | 1200 |
| gatgatttct caggctcacc ttagacattt cctgccacag acttagaatc agccatttct | 1260 |
| ctaaggaccc tgattccatt tcatgagaaa tgatagagac cacaatcaaa acaagtcatg | 1320 |
| aatttatact gatattttca attcaaatta aagatgaggt ttttgctaaa tttttttgag | 1380 |
| tttatatttg tatgtcttat gctgaaaaat cttgttcct aattagtaac ataattattc | 1440 |
| atttgatggg taaatatttt agggccgatt ctttggtttt atagccaaga taccctgttg | 1500 |

| | |
|---|---|
| ataaagtctt gtgggagcaa ttataagact ggcttatttt gaagcttttt aaaaaagaca | 1560 |
| tccttacctg ttttaactgt agattatatt aacttaaata ggtacagccc acgcttgact | 1620 |
| agttcagaga gcctcggcta ggtaggggat cgggactctg gcgggagggc ggcttggtgc | 1680 |
| gtttgcgggg atgggcggcc gcggcaggcc ctccgagcgt ggtggagccg ttctgtgaga | 1740 |
| cagccgggta cgagtcgtga cgctggaagg ggcaagcggg tggtgggcag gaatgcggtc | 1800 |
| cgccctgcag caaccggagg gggagggaga agggagcgga aaagtctcca ccggacgcgg | 1860 |
| ccatggctcg ggggggggggg ggcagcggag gagcgcttcc ggccgacgtc tcgtcgctga | 1920 |
| ttggcttctt ttcctcccgc cgtgtgtgaa aacacaattg tactaacctt cttctctttc | 1980 |
| ctctcctgac ag | 1992 |

<210> SEQ ID NO 45
<211> LENGTH: 2859
<212> TYPE: DNA
<213> ORGANISM: Artificial Sequence
<220> FEATURE:
<223> OTHER INFORMATION: CMV-CDK9-U1U2-hROSA

<400> SEQUENCE: 45

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcgggccgc cgctagtagt ggcggcggcg gaggcggggg | 420 |
| cagcggcggc ggcggcggag gcgcctctgc agctccggct cccctggcc tctcgggaac | 480 |
| tacaagtccc aggggggcctg gcggtgggcg gcgggcggaa gaggcggggt cggcgccgcg | 540 |
| aggccggaag tggccgtgga ggcggaagtg gcgcggccgc ggagggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga attttcaaca tatttgatat atttcaatcc attgccatca | 1080 |
| ttgttcttat cgatatttga gttggctcac tttgccagta agagtctatt caaattggct | 1140 |
| tctgagtcca tttgacacaa cacctttgat cttgacagt ttccttggtt ttaggtgcta | 1200 |
| gatgatttct caggctcacc ttagacattt cctgccacag acttagaatc agccatttct | 1260 |
| ctaaggaccc tgattccatt tcatgagaaa tgatagagac cacaatcaaa acaagtcatg | 1320 |
| aatttatact gatattttca attcaaatta aagatgaggt ttttgctaaa ttttttttgag | 1380 |
| tttatatttg tatgtcttat gctgaaaaat cttgttcct aattagtaac ataattattc | 1440 |
| atttgatggg taaatatttt agggccgatt ctttggtttt atagccaaga taccctgttg | 1500 |

```
ataaagtctt gtgggagcaa ttataagact ggcttatttt gaagcttttt aaaaaagaca    1560
tccttacctg ttttaactgt agattatatt aacttaaata ggtacagccc acgcttgact    1620
agtctcagag agcctcggct aggtagggga gcggaactct ggtgggaggg gaggtgcggt    1680
gcactggggg gatgggtggc tagggggggcc gtctggtggc ttgcggggt tgccttttccc   1740 gtgggaagtc gggaacataa tgtttgttac gttgggaggg aaaggggtgg ctggatgcag    1800
gcgggaggga ggcccgccct gcggcaaccg gaggggagg gagaagggag cggaaaatgc     1860
tcgaaaccgg acggagccat tgctctcgca gagggaggag cgcttccggc tagcctcttg    1920
tcgccgattg gccgtttctc ctcccgccgt gtgtgaaaac acaaatggcg tattctggtt    1980
ggagtaaagc tcctgtcagt tacaccgtcg ggagtacgca gccgcttagc gactctcgcg    2040 ttgcccctg ggtggggcgg gtaggtaggt ggggtgtaga gatgctgggt gtgcgggcgc     2100
ggccggcctc ctgcggcggg aggggagggt cagtgaaatt ggctctggcg cgggcgtcct    2160 cccacctcc ccttccttcg ggggagtcgg tttacccgcc gcctgcttgt cttcgacacc     2220
tgattggctg tcgaagctgt gggaccgggc ccttgctact ggctcgagtc tcacatgagc    2280
gaaaccactg cgcggggcgc gggggtggcg gggaggcggg cgttggtacg gtcctccccg    2340
aggccgagcg ccgcagtgtc tggccccgcg ccctgcgca acgtggcagg aagcgcgcg     2400 tggaggcggg ggcgggctgc cggccgagac ttctggatgg cggcggccgc ggctccgccc    2460
cgggttccca ccgcctgaag ggcgagacaa gcccgacctg ctacaggcac tcgtgggggt    2520
gggggaggag cggggggtcgg tccggctggt ttgtgggtgg gaggcgcttg ttctccaaaa   2580
accggcgcga gctgcaatcc tgaggagct gcggtggagg aggtggagag aaggccgcac     2640
ccttctgggc aggggagggg gagtgccgca atacctttat gggagttctt tgctgcctcc    2700
cgtcttgtaa ggaccgccct gggcctggaa gaagccctcc ctcctttcct cctcgcgtga    2760
tctcgtcatc gcctccatgt cgagtcgctt tcgattatg ggcgggattc ttttgcctag     2820
acaattgtac taaccttctt ctctttcctc tcctgacag                           2859
```

<210> SEQ ID NO 46
<211> LENGTH: 2242
<212> TYPE: DNA
<213> ORGANISM: Artificial Sequence
<220> FEATURE:
<223> OTHER INFORMATION: CMV-CDK9-U1U3-EF1

<400> SEQUENCE: 46

```
gcgttacata acttacggta atggcccgc ctggctgacc gcccaacgac ccccgcccat      60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc      360 ccggctcccc gcgccccga tcggggccgc cgctagtagt ggcggcggcg gaggcggggg     420
cagcggcggc ggcggcggag gcgcctctgc agctccggct ccccctggcc tctcgggaac    480
tacaagtccc aggggcctg gcggtgggcg gcgggcggaa gaggcggggt cggcgccgcg     540
aggccggaag tggccgtgga ggcggaagtg gcgcggccgc ggagggggcct ggagtgcggc   600 ggcggcggga cccggagcag gagcggcggc agcagcgact ggggggcggcg gcggcgcgtt   660 ggaggcggcc ggatccgttt aaacggctcg catctctcct tcacgcgccc gccgccctac    720
```

```
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagttaa    960
cgctggtggg tagggatgag ggagggaggg gcattgtgat gtacagggct gctctgtgag   1020
atcaagggtc tcttaagggt gggagctggg gcagggacta cgagagcagc cagatgggct   1080
gaaagtggaa ctcaagggt ttctggcacc tacctacctg cttcccgctg gggggtgggg   1140
agttggccca gagtcttaag attggggcag ggtggagagg tgggctcttc ctgcttccca   1200
ctcatcttat agctttcttt ccccagatcc gaattcgaga tccaaaccaa ggaggaaagg   1260
atatcacaga ggagagctag tcgggtttgc cgccagaaca caggtaagtg ccgtgtgtgg   1320
ttcccgcggg cctggcctct ttacgggtta tggcccttgc gtgccttgaa ttacttccac   1380
ctggctgcag tacgtgattc ttgatcccga gcttcgggtt ggaagtgggt gggagagttc   1440
gaggccttgc gcttaaggag ccccttcgcc tcgtgcttga gttgaggcct ggcctgggcg   1500
ctggggccgc cgcgtgcgaa tctggtggca ccttcgcgcc tgtctcgctg ctttcgataa   1560
gtctctagcc atttaaaatt tttgatgacc tgctgcgacg ctttttttct ggcaagatag   1620
tcttgtaaat gcgggccaag atctgcacac tggtatttcg gttttggg ccgcgggcgg   1680 cgacggggcc cgtgcgtccc agcgcacatg ttcggcgagg cggggcctgc gagcgcggcc   1740
accgagaatc ggacggggt agtctcaagc tggccggcct gctctggtgc ctggcctcgc   1800
gccgccgtgt atcgccccgc cctgggcggc aaggctggcc cggtcggcac cagttgcgtg   1860
agcggaaaga tggccgcttc ccggccctgc tgcaggagc tcaaaatgga ggacgcggcg   1920
ctcgggagag cgggcgggtg agtcacccac acaaaggaaa agggcctttc cgtcctcagc   1980
cgtcgcttca tgtgactcca cggagtaccg ggcgccgtcc aggcacctcg attagttctc   2040
gagcttttgg agtacgtcgt ctttaggttg ggggagggg ttttatgcga tggagtttcc   2100
ccacactgag tgggtggaga ctgaagttag gccagcttgg cacttgatgt aattctcctt   2160
ggaatttgcc cttttgagt ttggatcttg gttcattctc aagcctcaga cagtggttca   2220
aagttttttt cttccatttc ag                                             2242
```

<210> SEQ ID NO 47
<211> LENGTH: 1650
<212> TYPE: DNA
<213> ORGANISM: Artificial Sequence
<220> FEATURE:
<223> OTHER INFORMATION: CMV-CDK9-U1U3-mROSA

<400> SEQUENCE: 47

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc    360 ccggctcccc gcgcccccga tcggggccgc cgctagtagt ggcggcggcg gaggcggggg    420
cagcggcggc ggcggcggag gcgcctctgc agctccggct ccccctggcc tctcgggaac    480
```

| | |
|---|---|
| tacaagtccc aggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagttaa | 960 |
| cgctggtggg tagggatgag ggaggagggg gcattgtgat gtacagggct gctctgtgag | 1020 |
| atcaagggtc tcttaagggt gggagctggg gcagggacta cgagagcagc cagatgggct | 1080 |
| gaaagtggaa ctcaagggt ttctggcacc tacctacctg cttcccgctg gggggtgggg | 1140 |
| agttggccca gagtcttaag attggggcag ggtggagagg tgggctcttc ctgcttccca | 1200 |
| ctcatcttat agctttcttt ccccagatcc gaattcgaga tccaaaccaa ggaggaaagg | 1260 |
| atatcacaga ggagagctag ttcagagagc ctcggctagg tagggatcg ggactctggc | 1320 |
| gggagggcgg cttggtgcgt ttgcggggat gggcggccgc ggcaggccct ccgagcgtgg | 1380 |
| tggagccgtt ctgtgagaca gccgggtacg agtcgtgacg ctggaagggg caagcgggtg | 1440 |
| gtgggcagga atgcggtccg ccctgcagca accgagggg gagggagaag ggagcggaaa | 1500 |
| agtctccacc ggacgcggcc atggctcggg ggggggggg cagcggagga gcgcttccgg | 1560 |
| ccgacgtctc gtcgctgatt ggcttctttt cctcccgccg tgtgtgaaaa cacaattgta | 1620 |
| ctaaccttct tctctttcct ctcctgacag | 1650 |

<210> SEQ ID NO 48
<211> LENGTH: 2517
<212> TYPE: DNA
<213> ORGANISM: Artificial Sequence
<220> FEATURE:
<223> OTHER INFORMATION: CMV-CDK9-U1U3-hROSA

<400> SEQUENCE: 48

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc aggggcctg gcggtgggcg gcgggcggaa gaggcggggt cggcgccgcg | 540 |
| aggccggaag tggccgtgga ggcggaagtg gcgcggccgc ggaggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |

```
tgctcaactc tacgtctttg tttcgttttc tgttctgcgc cgttacagat cactagttaa    960
cgctggtggg tagggatgag ggagggaggg gcattgtgat gtacagggct gctctgtgag   1020
atcaagggtc tcttaagggt gggagctggg gcagggacta cgagagcagc cagatgggct   1080
gaaagtggaa ctcaagggt ttctggcacc tacctacctg cttcccgctg ggggtgggg   1140 agttggccca gagtcttaag attggggcag ggtggagagg tgggctcttc ctgcttccca   1200
ctcatcttat agctttcttt ccccagatcc gaattcgaga tccaaaccaa ggaggaaagg   1260
atatcacaga ggagagctag tctcagagag cctcggctag gtaggggagc ggaactctgg   1320
tgggagggga ggtgcggtgc actgggggga tgggtggcta gggggccgt ctggtggctt   1380 gcggggttg cctttcccgt gggaagtcgg gaacataatg tttgttacgt gggagggaa   1440 aggggtggct ggatgcaggc gggagggagg cccgccctgc ggcaaccgga ggggaggga   1500 gaagggagcg gaaaatgctc gaaaccggac ggagccattg ctctcgcaga gggaggagcg   1560
cttccggcta gcctcttgtc gccgattggc cgtttctcct cccgccgtgt gtgaaaacac   1620
aaatggcgta ttctggttgg agtaaagctc ctgtcagtta caccgtcggg agtacgcagc   1680
cgcttagcga ctctcgcgtt gcccctggg tggggcgggt aggtaggtgg ggtgtagaga   1740
tgctgggtgt gcgggcgcgg ccggcctcct gcggcgggag gggagggtca gtgaaattgg   1800
ctctggcgcg ggcgtcctcc caccctcccc ttccttcggg ggagtcggtt tacccgccgc   1860
ctgcttgtct tcgacacctg attggctgtc gaagctgtgg gaccgggccc ttgctactgg   1920
ctcgagtctc acatgagcga aaccactgcg cggggcgcgg gggtggcggg gaggcgggcg   1980
ttggtacggt cctccccgag gccgagcgcc gcagtgtctg gccccgcgcc cctgcgcaac   2040
gtggcaggaa gcgcgcgctg gaggcggggg cgggctgccg gccgagactt ctggatggcg   2100
gcggccgcgg ctccgccccg ggttcccacc gcctgaaggg cgagacaagc ccgacctgct   2160
acaggcactc gtggggtgg gggaggagcg gggtcggtc cggctggttt gtgggtggga   2220
ggcgcttgtt ctccaaaaac cggcgcgagc tgcaatcctg agggagctgc ggtggaggag   2280
gtggagagaa ggccgcaccc ttctgggcag ggggagggga gtgccgcaat acctttatgg   2340
gagttctttg ctgcctcccg tcttgtaagg accgccctgg gcctggaaga agccctccct   2400
cctttcctcc tcgcgtgatc tcgtcatcgc ctccatgtcg agtcgcttct cgattatggg   2460
cgggattctt ttgcctagac aattgtacta accttcttct ctttcctctc ctgacag    2517
```

<210> SEQ ID NO 49
<211> LENGTH: 2627
<212> TYPE: DNA
<213> ORGANISM: Artificial Sequence
<220> FEATURE:
<223> OTHER INFORMATION: CMV-CDK9-U2U3-EF1

<400> SEQUENCE: 49

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tgcagcggga cgcgccaccc cgagcccag ctccggcgcc    360 ccggctcccc gcgccccga tcggggccgc cgctagtagt ggcggcggcg gaggcggggg    420
```

```
cagcggcggc ggcggcggag gcgcctctgc agctccggct cccccctggcc tctcgggaac    480
tacaagtccc aggggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacagagta atgacatggt tccttccatc ctccaaaggt    720
gaccaataat agtttgtaag tatcattatg aactaatgaa ttttcaacat atttgatata    780
tttcaatcca ttgccatcat tgttcttatc gatatttgag ttggctcact ttgccagtaa    840
gagtctattc aaattggctt ctgagtccat ttgacacaac acctttgatc tttgacagtt    900
tccttggttt taggtgctag atgatttctc aggctcacct tagacatttc ctgccacaga    960
cttagaatca gccatttctc taaggaccct gattccattt catgagaaat gatagagacc   1020
acaatcaaaa caagtcatga atttatactg atatttcaa ttcaaattaa agatgaggtt    1080
tttgctaaat tttttgagt ttatatttgt atgtcttatg ctgaaaaatc ttgtttccta    1140
attagtaaca taattattca tttgatgggt aaatatttta gggccgattc tttggttta    1200
tagccaagat accctgttga taaagtcttg tgggagcaat tataagactg cttattttg    1260
aagcttttta aaaagacat ccttacctgt tttaactgta gattatatta acttaaatag    1320
gtacagccca cgcttgacta gttaacgctg gtgggtaggg atgagggagg gaggggcatt   1380
gtgatgtaca gggctgctct gtgagatcaa gggtctctta agggtgggag ctggggcagg   1440
gactacgaga gcagccagat gggctgaaag tggaactcaa ggggtttctg gcacctacct   1500
acctgcttcc cgctgggggg tggggagttg gcccagagtc ttaagattgg ggcagggtgg   1560
agaggtgggc tcttcctgct tcccactcat cttatagctt tctttcccca gatccgaatt   1620
cgagatccaa accaaggagg aaaggatatc acagaggaga gctagtcggg tttgccgcca   1680
gaacacaggt aagtgccgtg tgtggttccc gcgggcctgg cctctttacg ggttatggcc    1740
cttgcgtgcc ttgaattact tccacctggc tgcagtacgt gattcttgat cccgagcttc   1800
gggttggaag tgggtgggag agttcgaggc cttgcgctta aggagcccct tcgcctcgtg   1860
cttgagttga ggcctggcct gggcgctggg gccgccgcgt gcgaatctgg tggcaccttc   1920
gcgcctgtct cgctgctttc gataagtctc tagccattta aaattttga tgacctgctg   1980
cgacgctttt tttctggcaa gatagtcttg taaatgcggg ccaagatctg cacactggta   2040
tttcggtttt tggggccgcg ggcggcgacg gggcccgtgc gtcccagcgc acatgttcgg   2100
cgaggcgggg cctgcgagcg cggccaccga gaatcggacg ggggtagtct caagctggcc   2160
ggcctgctct ggtgcctggc ctcgcgccgc cgtgtatcgc cccgccctgg gcggcaaggc   2220
tggcccggtc ggcaccagtt gcgtgagcgg aaagatggcc gcttccggc cctgctgcag    2280
ggagctcaaa atggaggacg cggcgctcgg gagagcgggc gggtgagtca cccacacaaa   2340
ggaaaagggc ctttccgtcc tcagccgtcg cttcatgtga ctccacggag taccgggcgc   2400
cgtccaggca cctcgattag ttctcgagct tttggagtac gtcgtcttta ggttgggggg   2460
aggggtttta tgcgatggag tttccccaca ctgagtgggt ggagactgaa gttaggccag   2520
cttggcactt gatgtaattc tccttggaat ttgcccttt tgagtttgga tcttggttca    2580
ttctcaagcc tcagacagtg gttcaaagtt tttttcttcc atttcag                  2627
```

<210> SEQ ID NO 50
<211> LENGTH: 2035
<212> TYPE: DNA
<213> ORGANISM: Artificial Sequence
<220> FEATURE:
<223> OTHER INFORMATION: CMV-CDK9-U2U3-mROSA

<400> SEQUENCE: 50

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc      360
ccggctcccc gcgccccga tcggggccgc cgctagtagt ggcggcggcg gaggcggggg     420
cagcggcggc ggcggcggag cgcctctgc agctccggct cccctggcc tctcgggaac      480
tacaagtccc aggggcctg cggtgggcg gcgggcggaa gaggcggggt cggcgccgcg     540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacagagta atgacatggt tccttccatc ctccaaaggt     720
gaccaataat agtttgtaag tatcattatg aactaatgaa ttttcaacat atttgatata     780
tttcaatcca ttgccatcat tgttcttatc gatatttgag ttggctcact ttgccagtaa     840
gagtctattc aaattggctt ctgagtccat ttgacacaac accttttgatc tttgacagtt     900
tccttggttt taggtgctag atgatttctc aggctcacct tagacatttc ctgccacaga     960
cttagaatca gccatttctc taaggaccct gattccattt catgagaaat gatagagacc    1020
acaatcaaaa caagtcatga atttatactg atattttcaa ttcaaattaa agatgaggtt    1080
tttgctaaat ttttttgagt ttatatttgt atgtcttatg ctgaaaaatc ttgtttccta    1140
attagtaaca taattattca tttgatgggt aaatattta gggccgattc tttggtttta    1200
tagccaagat accctgttga taaagtcttg tgggagcaat tataagactg gcttattttg    1260
aagcttttta aaaagacat ccttacctgt tttaactgta gattatatta acttaaatag     1320
gtacagccca cgcttgacta gttaacgctg gtgggtaggg atgagggagg gaggggcatt    1380
gtgatgtaca gggctgctct gtgagatcaa gggtctctta agggtgggag ctggggcagg    1440
gactacgaga gcagccagat gggctgaaag tggaactcaa ggggtttctg gcacctacct    1500
acctgcttcc cgctggggg tgggagttg gcccagagtc ttaagattgg ggcagggtgg    1560
agaggtgggc tcttcctgct tcccactcat cttatagctt tctttcccca gatccgaatt    1620
cgagatccaa accaaggagg aaaggatatc acagaggaga gctagttcag agagcctcgg    1680
ctaggtaggg gatcgggact ctggcgggag ggcggcttgg tgcgtttgcg gggatgggcg    1740
gccgcggcag gccctccgag cgtggtggag ccgttctgtg agacagccgg gtacgagtcg    1800
tgacgctgga aggggcaagc gggtggtggg caggaatgcg gtccgccctg cagcaaccgg    1860
agggggaggg agaagggagc ggaaaagtct ccaccggacg cggccatggc tcgggggggg    1920
ggggcagcg gaggagcgct tccggccgac gtctcgtcgc tgattggctt ctttttcctcc    1980
cgccgtgtgt gaaaacacaa ttgtactaac cttcttctct ttcctctcct gacag         2035
```

<210> SEQ ID NO 51
<211> LENGTH: 2902
<212> TYPE: DNA
<213> ORGANISM: Artificial Sequence
<220> FEATURE:

<223> OTHER INFORMATION: CMV-CDK9-U2U3-hROSA

<400> SEQUENCE: 51

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tgcagcggga cgcgccaccc cgagcccag ctccggcgcc       360
ccggctcccc gcgcccccga tcggggccgc cgctagtagt ggcggcggcg gaggcggggg     420
cagcggcggc ggcggcggag gcgcctctgc agctccggct ccccctggcc tctcgggaac     480
tacaagtccc aggggcctg gcggtgggcg gcgggcggaa gaggcgggt cggcgccgcg       540
aggccggaag tggccgtgga ggcggaagtg gcgcggccgc ggaggggcct ggagtgcggc     600
ggcggcggga cccggagcag gagcggcggc agcagcgact gggggcggcg gcggcgcgtt     660
ggaggcggcc ggatccgttt aaacagagta atgacatggt tccttccatc ctccaaaggt     720
gaccaataat agtttgtaag tatcattatg aactaatgaa ttttcaacat atttgatata     780
tttcaatcca ttgccatcat tgttcttatc gatatttgag ttggctcact ttgccagtaa     840
gagtctattc aaattggctt ctgagtccat ttgacacaac cctttgatc tttgacagtt      900
tccttggttt taggtgctag atgatttctc aggctcacct tagacatttc ctgccacaga     960
cttagaatca gccatttctc taaggaccct gattccattt catgagaaat gatagagacc    1020
acaatcaaaa caagtcatga atttatactg atattttcaa ttcaaattaa agatgaggtt    1080
tttgctaaat ttttttgagt ttatatttgt atgtcttatg ctgaaaaatc ttgtttccta    1140
attagtaaca taattattca tttgatgggt aaatatttta gggccgattc tttggtttta    1200
tagccaagat accctgttga taaagtcttg tgggagcaat tataagactg gcttattttg    1260
aagcttttta aaaagacat ccttacctgt tttaactgta gattatatta acttaaatag     1320
gtacagccca cgcttgacta gttaacgctg gtgggtaggg atgagggagg gaggggcatt    1380
gtgatgtaca gggctgctct gtgagatcaa gggtctctta agggtgggag ctggggcagg    1440
gactacgaga gcagccagat gggctgaaag tggaactcaa ggggtttctg gcacctacct    1500
acctgcttcc cgctgggggg tggggagttg gcccagagtc ttaagattgg ggcagggtgg    1560
agaggtgggc tcttcctgct tcccactcat cttatagctt tctttcccca gatccgaatt    1620
cgagatccaa accaaggagg aaaggatatc acagaggaga gctagtctca gagagcctcg    1680
gctaggtagg ggagcggaac tctggtggga ggggaggtgc ggtgcactgg ggggatgggt    1740
ggctaggggg gccgtctggt ggcttgcggg ggttgccttt cccgtgggaa gtcgggaaca    1800
taatgtttgt tacgtgggga gggaaagggg tggctggatg caggcgggag ggaggcccgc    1860
cctgcggcaa ccggaggggg agggagaagg gagcggaaaa tgctcgaaac cggacggagc    1920
cattgctctc gcagagggag gagcgcttcc ggctagcctc ttgtcgccga ttggccgttt    1980
ctcctcccgc cgtgtgtgaa acacaaatg gcgtattctg gttggagtaa agctcctgtc     2040
agttacaccg tcgggagtac gcagccgctt agcgactctc gcgttgcccc ctgggtgggg    2100
cgggtaggta ggtggggtgt agagatgctg ggtgtgcggg cgcggccggc ctcctgcggc    2160
gggaggggag ggtcagtgaa attggctctg gcgcgggcgt cctcccaccc tccccttcct    2220
tcgggggagt cggtttaccc gccgcctgct tgtcttcgac acctgattgg ctgtcgaagc    2280
```

| | |
|---|---|
| tgtgggaccg ggcccttgct actggctcga gtctcacatg agcgaaacca ctgcgcgggg | 2340 |
| cgcggggtg gcggggaggc gggcgttggt acggtcctcc ccgaggccga gcgccgcagt | 2400 |
| gtctggcccc gcgcccctgc gcaacgtggc aggaagcgcg cgctggaggc ggggcgggc | 2460 |
| tgccggccga gacttctgga tggcggcggc cgcggctccg ccccgggttc ccaccgcctg | 2520 |
| aagggcgaga caagcccgac ctgctacagg cactcgtggg ggtgggggag gagcggggt | 2580 |
| cggtccggct ggtttgtggg tgggaggcgc ttgttctcca aaaaccggcg cgagctgcaa | 2640 |
| tcctgaggga gctgcggtgg aggaggtgga gagaaggccg cacccttctg gcaggggga | 2700 |
| ggggagtgcc gcaataccttt atgggagtt ctttgctgcc tcccgtcttg taaggaccgc | 2760 |
| cctgggcctg gaagaagccc tccctccttt cctcctcgcg tgatctcgtc atcgcctcca | 2820 |
| tgtcgagtcg cttctcgatt atgggcggga ttcttttgcc tagacaattg tactaacctt | 2880 |
| cttctctttc ctctcctgac ag | 2902 |

<210> SEQ ID NO 52
<211> LENGTH: 2908
<212> TYPE: DNA
<213> ORGANISM: Artificial Sequence
<220> FEATURE:
<223> OTHER INFORMATION: CMV-CDK9-U1U2U3-EF1

<400> SEQUENCE: 52

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tgcagcggga cgcgccaccc cgagcccag ctccggcgcc | 360 |
| ccggctcccc gcgcccccga tcggggccgc cgctagtagt ggcggcggcg gaggcggggg | 420 |
| cagcggcggc ggcggcggag gcgcctctgc agctccggct ccccctggcc tctcgggaac | 480 |
| tacaagtccc agggggcctg gcggtgggcg gcgggcggaa gaggcggggt cggcgccgcg | 540 |
| aggccggaag tggccgtgga ggcggaagtg gcgcggccgc ggagggggcct ggagtgcggc | 600 |
| ggcggcggga cccggagcag gagcggcggc agcagcgact gggggcggcg gcggcgcgtt | 660 |
| ggaggcggcc ggatccgttt aaacggctcg catctctcct tcacgcgccc gccgccctac | 720 |
| ctgaggccgc catccacgcc ggttgagtcg cgttctgccg cctcccgcct gtggtgcctc | 780 |
| ctgaactgcg tccgccgtct aggtaagttt aaagctcagg tcgagaccgg gcctttgtcc | 840 |
| ggcgctccct tggagcctac ctagactcag ccggctctcc acgctttgcc tgaccctgct | 900 |
| tgctcaactc tacgtctttg tttcgttttc tgttctgcgc cgttacagat cactagtgtt | 960 |
| taaacagagt aatgacatgg ttccttccat cctccaaagg tgaccaataa tagtttgtaa | 1020 |
| gtatcattat gaactaatga attttcaaca tatttgatat atttcaatcc attgccatca | 1080 |
| ttgttcttat cgatatttga gttggctcac tttgccagta agagtctatt caaattggct | 1140 |
| tctgagtcca tttgacacaa caccttttgat ctttgacagt ttccttggtt ttaggtgcta | 1200 |
| gatgatttct caggctcacc ttagacattt cctgccacag acttagaatc agccatttct | 1260 |
| ctaaggaccc tgattccatt tcatgagaaa tgatagagac cacaatcaaa acaagtcatg | 1320 |
| aatttatact gatatttca attcaaatta aagatgaggt ttttgctaaa tttttttgag | 1380 |

```
tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttatttt gaagcttttt aaaaaagaca   1560
tccttacctg ttttaactgt agattatatt aacttaaata ggtacagccc acgcttgact   1620
agttaacgct ggtgggtagg gatgagggag ggagggcat tgtgatgtac agggctgctc    1680
tgtgagatca agggtctctt aagggtggga gctgggcag ggactacgag agcagccaga    1740
tgggctgaaa gtggaactca agggtttct ggcacctacc tacctgcttc ccgctggggg    1800
gtggggagtt ggcccagagt cttaagattg gggcagggtg gagaggtggg ctcttcctgc   1860
ttcccactca tcttatagct ttcttttccc agatccgaat tcgagatcca aaccaaggag   1920
gaaaggatat cacagaggag agctagtcgg gtttgccgcc agaacacagg taagtgccgt   1980
gtgtggttcc cgcgggcctg gcctctttac gggttatggc ccttgcgtgc cttgaattac   2040
ttccacctgg ctgcagtacg tgattcttga tcccgagctt cgggttggaa gtgggtggga   2100
gagttcgagg ccttgcgctt aaggagcccc ttcgcctcgt gcttgagttg aggcctggcc   2160
tgggcgctgg ggccgccgcg tgcgaatctg gtggcacctt cgcgcctgtc tcgctgcttt   2220
cgataagtct ctagccattt aaaattttg atgacctgct gcgacgcttt ttttctggca    2280
agatagtctt gtaaatgcgg gccaagatct gcacactggt atttcggttt ttggggccgc   2340
gggcggcgac ggggcccgtg cgtcccagcg cacatgttcg gcgaggcggg gcctgcgagc   2400
gcggccaccg agaatcggac gggggtagtc tcaagctggc cggcctgctc tggtgcctgg   2460
cctcgcgccg ccgtgtatcg ccccgccctg gcggcaagg ctggcccggt cggcaccagt    2520
tgcgtgagcg gaaagatggc cgcttcccgg ccctgctgca gggagctcaa aatggaggac   2580
gcggcgctcg ggagagcggg cggtgagtc acccacacaa aggaaaaggg ctttccgtc     2640 ctcagccgtc gcttcatgtg actccacgga gtaccgggcg ccgtccaggc acctcgatta   2700
gttctcgagc ttttggagta cgtcgtcttt aggttggggg gaggggtttt atgcgatgga   2760 gttccccac actgagtggg tggagactga agttaggcca gcttggcact tgatgtaatt    2820
ctccttggaa tttgcccttt ttgagtttgg atcttggttc attctcaagc ctcagacagt   2880
ggttcaaagt ttttttcttc catttcag                                      2908

<210> SEQ ID NO 53
<211> LENGTH: 2316
<212> TYPE: DNA
<213> ORGANISM: Artificial Sequence
<220> FEATURE:
<223> OTHER INFORMATION: CMV-CDK9-U1U2U3-mROSA

<400> SEQUENCE: 53
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg ggtcgcgaca tgcagcggga cgcgccaccc cgagcccag ctccggcgcc     360 ccggctcccc gcgcccccga tcggggccgc cgctagtagt ggcggcggcg gaggcggggg    420
cagcggcggc ggcggcggag gcgcctctgc agctccggct ccccctggcc tctcgggaac   480
tacaagtccc aggggggcctg gcggtgggcg gcgggcggaa gaggcggggt cggcgccgcg   540
```

```
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagtttgtaa   1020
gtatcattat gaactaatga attttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200
gatgatttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa tttttttgag   1380
tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttatttt gaagcttttt aaaaaagaca   1560
tccttacctg ttttaactgt agattatatt aacttaaata ggtacagccc acgcttgact   1620
agttaacgct ggtgggtagg gatgagggag ggaggggcat tgtgatgtac agggctgctc   1680
tgtgagatca agggtctctt aagggtggga gctgggcag ggactacgag agcagccaga   1740
tgggctgaaa gtggaactca aggggtttct ggcacctacc tacctgcttc ccgctggggg   1800
gtggggagtt ggcccagagt cttaagattg gggcagggtg gagaggtggg ctcttcctgc   1860
ttcccactca tcttatagct ttcttttccc agatccgaat tcgagatcca aaccaaggag   1920
gaaaggatat cacagaggag agctagttca gagagcctcg gctaggtagg ggatcgggac   1980
tctggcggga gggcggcttg gtgcgtttgc ggggatgggc ggccgcggca ggccctccga   2040
gcgtggtgga gccgttctgt gagacagccg ggtacgagtc gtgacgctgg aaggggcaag   2100
cgggtggtgg gcaggaatgc ggtccgccct gcagcaaccg gaggggagg gagaaggag    2160 cggaaaagtc tccaccggac gcggccatgg ctcgggggg ggggggcagc ggaggagcgc    2220
ttccggccga cgtctcgtcg ctgattggct tcttttcctc ccgccgtgtg tgaaaacaca   2280
attgtactaa ccttcttctc tttcctctcc tgacag                             2316
```

<210> SEQ ID NO 54
<211> LENGTH: 3183
<212> TYPE: DNA
<213> ORGANISM: Artificial Sequence
<220> FEATURE:
<223> OTHER INFORMATION: CMV-CDK9-U1U2U3-hROSA

<400> SEQUENCE: 54

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
```

```
acatgacctt atgggacttt cctacttggc agtacatcta cgtattagtc atcgctatta    300
ccatggcccg ggtcgcgaca tgcagcggga cgcgccaccc cgagcccag  ctccggcgcc    360
ccggctcccc gcgccccga  tcggggccgc cgctagtagt ggcggcggcg gaggcggggg    420
cagcggcggc ggcggcggag gcgcctctgc agctccggct ccccctggcc tctcgggaac    480
tacaagtccc agggggcctg gcggtgggcg gcgggcggaa gaggcggggt cggcgccgcg    540
aggccggaag tggccgtgga ggcggaagtg gcgcggccgc ggaggggcct ggagtgcggc    600
ggcggcggga cccggagcag gagcggcggc agcagcgact gggggcggcg gcggcgcgtt    660
ggaggcggcc ggatccgttt aaacggctcg catctctcct tcacgcgccc gccgccctac    720
ctgaggccgc catccacgcc ggttgagtcg cgttctgccg cctcccgcct gtggtgcctc    780
ctgaactgcg tccgccgtct aggtaagttt aaagctcagg tcgagaccgg gcctttgtcc    840
ggcgctccct tggagcctac ctagactcag ccggctctcc acgctttgcc tgaccctgct    900
tgctcaactc tacgtctttg tttcgttttc tgttctgcgc cgttacagat cactagtgtt    960
taaacagagt aatgacatgg ttccttccat cctccaaagg tgaccaataa tagttttgtaa   1020
gtatcattat gaactaatga attttcaaca tatttgatat atttcaatcc attgccatca   1080
ttgttcttat cgatatttga gttggctcac tttgccagta agagtctatt caaattggct   1140
tctgagtcca tttgacacaa cacctttgat ctttgacagt ttccttggtt ttaggtgcta   1200
gatgatttct caggctcacc ttagacattt cctgccacag acttagaatc agccatttct   1260
ctaaggaccc tgattccatt tcatgagaaa tgatagagac cacaatcaaa acaagtcatg   1320
aatttatact gatattttca attcaaatta aagatgaggt ttttgctaaa ttttttttgag   1380
tttatatttg tatgtcttat gctgaaaaat cttgtttcct aattagtaac ataattattc   1440
atttgatggg taaatatttt agggccgatt ctttggtttt atagccaaga taccctgttg   1500
ataaagtctt gtgggagcaa ttataagact ggcttatttt gaagcttttt aaaaaagaca   1560
tccttacctg ttttaactgt agattatatt aacttaaata ggtacagccc acgcttgact   1620
agttaacgct ggtgggtagg gatgagggag ggaggggcat tgtgatgtac agggctgctc   1680
tgtgagatca agggtctctt aagggtggga gctgggcag  ggactacgag agcagccaga   1740
tgggctgaaa gtggaactca aggggtttct ggcacctacc tacctgcttc ccgctggggg   1800
gtggggagtt ggcccagagt cttaagattg gggcagggtg gagaggtggg ctcttcctgc   1860
ttcccactca tcttatagct ttcttttcccc agatccgaat tcgagatcca aaccaaggag   1920
gaaaggatat cacagaggag agctagtctc agagagcctc ggctaggtag gggagcggaa   1980
ctctggtggg aggggaggtg cggtgcactg gggggatggg tggctagggg ggccgtctgg   2040
tggcttgcgg gggttgcctt tcccgtggga agtcggaac  ataatgtttg ttacgttggg   2100
agggaaaggg gtggctggat gcaggcggga gggaggcccg cctgcggca  accggagggg   2160
gagggagaag ggagcggaaa atgctcgaaa ccggacggag ccattgctct cgcagaggga   2220
ggagcgcttc cggctagcct cttgtcgccg attggccgtt tctcctcccg ccgtgtgtga   2280
aaacacaaat ggcgtattct ggttggagta aagctcctgt cagttacacc gtcgggagta   2340
cgcagccgct tagcgactct cgcgttgccc cctgggtggg gcgggtaggt aggtggggtg   2400
tagagatgct gggtgtgcgg gcgcggccgg cctcctgcgg cgggagggga gggtcagtga   2460
aattggctct ggcgcgggcg tcctcccacc ctcccttcc  ttcggggag  tcggtttacc   2520
cgccgcctgc ttgtcttcga cacctgattg gctgtcgaag ctgtgggacc gggcccttgc   2580
tactggctcg agtctcacat gagcgaaacc actgcgcggg gcgcgggggt ggcggggagg   2640
```

```
cgggcgttgg tacggtcctc cccgaggccg agcgccgcag tgtctggccc cgcgcccctg    2700
cgcaacgtgg caggaagcgc gcgctggagg cgggggcggg ctgccggccg agacttctgg    2760
atggcggcgg ccgcggctcc gccccgggtt cccaccgcct gaagggcgag acaagcccga    2820
cctgctacag gcactcgtgg gggtggggga ggagcggggg tcggtccggc tggtttgtgg    2880
gtgggaggcg cttgttctcc aaaaaccggc gcgagctgca atcctgaggg agctgcggtg    2940
gaggaggtgg agagaaggcc gcaccttct gggcaggggg aggggagtgc cgcaataccct   3000 ttatgggagt tctttgctgc ctcccgtctt gtaaggaccg ccctgggcct ggaagaagcc    3060
ctccctcctt tcctcctcgc gtgatctcgt catcgcctcc atgtcgagtc gcttctcgat    3120
tatgggcggg attcttttgc ctagacaatt gtactaacct tcttctcttt cctctcctga    3180
cag                                                                 3183
```

<210> SEQ ID NO 55
<211> LENGTH: 1848
<212> TYPE: DNA
<213> ORGANISM: Artificial Sequence
<220> FEATURE:
<223> OTHER INFORMATION: CMV-bActine-U1-EF1

<400> SEQUENCE: 55

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tggtcgaggt gagccccacg ttctgcttca ctctccccat     360
ctcccccccc tccccacccc caattttgta tttatttatt ttttaattat tttgtgcagc     420 gatggggcg gggggggggg ggggcgcgc gccaggcggg gcggggcggg gcgaggggcg       480
gggcggggcg aggcggagag gtgcggcggc agccaatcag agcggcgcgc tccgaaagtt     540 tcctttatg gcgaggcggc ggcggcggcg gccctataaa aagcgaagcg cgcggcgggc      600
ggatccgttt aaacggctcg catctctcct tcacgcgccc gccgccctac ctgaggccgc     660
catccacgcc ggttgagtcg cgttctgccg cctcccgcct gtggtgcctc ctgaactgcg     720
tccgccgtct aggtaagttt aaagctcagg tcgagaccgg cctttgtcc ggcgctccct     780 tggagcctac ctagactcag ccggctctcc acgctttgcc tgaccctgct tgctcaactc     840
tacgtctttg tttcgttttc tgttctgcgc cgttacagat cactagtcgg gtttgccgcc     900
agaacacagg taagtgccgt gtgtggttcc cgcgggcctg gcctctttac gggttatggc     960
ccttgcgtgc cttgaattac ttccacctgg ctgcagtacg tgattcttga tcccgagctt    1020
cgggttggaa gtgggtggga gagttcgagg ccttgcgctt aaggagcccc ttcgcctcgt    1080
gcttgagttg aggcctggcc tgggcgctgg gccgccgcg tgcgaatctg gtggcaccctt    1140 cgcgcctgtc tcgctgcttt cgataagtct ctagccattt aaaattttg atgacctgct    1200 gcgacgcttt ttttctggca agatagtctt gtaaatgcgg gccaagatct gcacactggt    1260
atttcggttt ttggggccgc gggcggcgac ggggcccgtg cgtcccagcg cacatgttcg    1320
gcgaggcggg gcctgcgagc gcggccaccg agaatcggac gggggtagtc tcaagctggc    1380
cggcctgctc tggtgcctgg cctcgcgccg ccgtgtatcg ccccgccctg ggcggcaagg    1440
```

```
ctggcccggt cggcaccagt tgcgtgagcg aaagatggcc cgcttcccgg ccctgctgca    1500
gggagctcaa aatggaggac gcggcgctcg ggagagcggg cgggtgagtc acccacacaa    1560
aggaaaaggg cctttccgtc ctcagccgtc gcttcatgtg actccacgga gtaccgggcg    1620
ccgtccaggc acctcgatta gttctcgagc ttttggagta cgtcgtcttt aggttggggg    1680
gaggggtttt atgcgatgga gtttccccac actgagtggg tggagactga agttaggcca    1740
gcttggcact tgatgtaatt ctccttggaa tttgcccttt ttgagtttgg atcttggttc    1800
attctcaagc ctcagacagt ggttcaaagt tttttttcttc catttcag               1848
```

`<210>` SEQ ID NO 56
`<211>` LENGTH: 1256
`<212>` TYPE: DNA
`<213>` ORGANISM: Artificial Sequence
`<220>` FEATURE:
`<223>` OTHER INFORMATION: CMV-bActine-U1-mROSA

`<400>` SEQUENCE: 56

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tggtcgaggt gagccccacg ttctgcttca ctctccccat    360 ctccccccc tccccacccc caattttgta tttatttatt ttttaattat tttgtgcagc    420 gatggggcg gggggggggg gggggcgcgc gccaggcggg gcggggcggg gcgaggggcg    480
gggcggggca aggcggagag gtgcggcggc agccaatcag agcggcgcgc tccgaaagtt    540
tccttttatg gcgaggcggc ggcggcggcg gccctataaa aagcgaagcg cgcggcgggc    600
ggatccgttt aaacggctcg catctctcct tcacgcgccc gccgccctac ctgaggccgc    660
catccacgcc ggttgagtcg cgttctgccg cctcccgcct gtggtgcctc ctgaactgcg    720
tccgccgtct aggtaagttt aaagctcagg tcgagaccgg gcctttgtcc ggcgctccct    780
tggagcctac ctagactcag ccggctctcc acgctttgcc tgaccctgct tgctcaactc    840
tacgtctttg tttcgttttc tgttctgcgc cgttacagat cactagttca gagagcctcg    900
gctaggtagg ggatcgggac tctggcggga gggcggcttg gtgcgtttgc ggggatgggc    960
ggccgcggca ggccctccga gcgtggtgga gccgttctgt gagacagccg ggtacgagtc    1020
gtgacgctgg aaggggcaag cgggtggtgg gcaggaatgc ggtccgccct gcagcaaccg    1080
gagggggagg gagaagggag cggaaaagtc tccaccggac gcggccatgg ctcgggggg    1140 gggggcagc ggaggagcgc ttccggccga cgtctcgtcg ctgattggct tcttttcctc    1200
ccgccgtgtg tgaaaacaca attgtactaa ccttcttctc tttcctctcc tgacag       1256
```

`<210>` SEQ ID NO 57
`<211>` LENGTH: 2123
`<212>` TYPE: DNA
`<213>` ORGANISM: Artificial Sequence
`<220>` FEATURE:
`<223>` OTHER INFORMATION: CMV-bActine-U1-hROSA

`<400>` SEQUENCE: 57

```
gcgttacata acttacggta aatggcccgc ctggctgacc gcccaacgac ccccgcccat     60
tgacgtcaat aatgacgtat gttcccatag taacgccaat agggactttc cattgacgtc    120
```

```
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tggtcgaggt gagccccacg ttctgcttca ctctccccat      360
ctccccccc tccccacccc caattttgta tttatttatt ttttaattat tttgtgcagc      420
gatggggcg gggggggggg ggggcgcgc gccaggcggg gcgggggggg gcaggggcg         480
gggcggggcg aggcggagag gtgcggcggc agccaatcag agcggcgcgc tccgaaagtt      540
tccttttatg gcgaggcggc ggcggcggcg gccctataaa aagcgaagcg cgcggcgggc      600
ggatccgttt aaacggctcg catctctcct tcacgcgccc gccgccctac ctgaggccgc      660
catccacgcc ggttgagtcg cgttctgccg cctcccgcct gtggtgcctc ctgaactgcg      720
tccgccgtct aggtaagttt aaagctcagg tcgagaccgg gcctttgtcc ggcgctccct      780
tggagcctac ctagactcag ccggctctcc acgctttgcc tgaccctgct tgctcaactc      840
tacgtctttg tttcgttttc tgttctgcgc cgttacagat cactagtctc agagagcctc      900
ggctaggtag gggagcggaa ctctggtggg aggggaggtg cggtgcactg ggggatggg       960
tggctagggg ggccgtctgg tggcttgcgg gggttgcctt tcccgtggga agtcgggaac     1020
ataatgtttg ttacgttggg agggaaaggg gtggctggat gcaggcggga gggaggcccg     1080
ccctgcggca accggagggg gagggagaag ggagcggaaa atgctcgaaa ccggacggag     1140
ccattgctct cgcagaggga ggagcgcttc cggctagcct cttgtcgccg attggccgtt     1200
tctcctcccg ccgtgtgtga aaacacaaat ggcgtattct ggttggagta aagctcctgt     1260
cagttacacc gtcgggagta cgcagccgct tagcgactct cgcgttgccc ctgggtgggg    1320
gcgggtaggt aggtgggtg tagagatgct gggtgtgcgg gcgcggccgg cctcctgcgg     1380
cgggagggga gggtcagtga aattggctct ggcgcgggcg tcctcccacc ctcccttcc      1440
ttcgggggag tcggtttacc cgccgcctgc ttgtcttcga cacctgattg gctgtcgaag     1500
ctgtgggacc gggcccttgc tactggctcg agtctcacat gagcgaaacc actgcgcggg     1560
gcgcggggt ggcggggagg cgggcgttgg tacggtcctc cccgaggccg agcgccgcag     1620
tgtctggccc cgcgcccctg cgcaacgtgg caggaagcgc gcgctggagg cggggcggg     1680
ctgccggccg agacttctgg atggcggcgg ccgcggctcc gccccgggtt cccaccgcct     1740
gaagggcgag acaagcccga cctgctacag gcactcgtgg gggtggggga ggagcggggg     1800
tcggtccggc tggtttgtgg gtgggaggcg cttgttctcc aaaaaccggc gcgagctgca     1860
atcctgaggg agctgcggtg gaggaggtgg agagaaggcc gcacccttct gggcaggggg    1920
aggggagtgc cgcaataact ttatggggagt tctttgctgc ctcccgtctt gtaaggaccg    1980
ccctgggcct ggaagaagcc ctccctcctt tcctcctcgc gtgatctcgt catcgcctcc     2040
atgtcgagtc gcttctcgat tatgggcggg attcttttgc ctagacaatt gtactaacct     2100
tcttctcttt cctctcctga cag                                            2123
```

<210> SEQ ID NO 58
<211> LENGTH: 2239
<212> TYPE: DNA
<213> ORGANISM: Artificial Sequence
<220> FEATURE:
<223> OTHER INFORMATION: CMV-bActine-U2-EF1

<400> SEQUENCE: 58

```
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg ggtcgcgaca tggtcgaggt gagcccacg  ttctgcttca ctctccccat   360
ctcccccccc tccccacccc caattttgta tttatttatt ttttaattat tttgtgcagc   420 gatggggcg gggggggggg ggggcgcgc gccaggcggg gcgggcggg gcgaggggcg     480 gggcggggcg aggcggagag gtgcggcggc agccaatcag agcggcgcgc tccgaaagtt   540 tcctttatg gcgaggcggc ggcggcgcg gccctataaa aagcgaagcg cgcggcgggc     600
ggatccacta gtgtttaaac agagtaatga catggttcct tccatcctcc aaaggtgacc   660
aataatagtt tgtaagtatc attatgaact aatgaatttt caacatattt gatatatttc   720
aatccattgc catcattgtt cttatcgata tttgagttgg ctcactttgc cagtaagagt   780
ctattcaaat tggcttctga gtccattga  cacaacacct tgatctttg  acagtttcct   840 tggttttagg tgctagatga tttctcaggc tcaccttaga catttcctgc cacagactta   900
gaatcagcca tttctctaag gaccctgatt ccatttcatg agaaatgata gagaccacaa   960
tcaaaacaag tcatgaattt atactgatat tttcaattca aattaaagat gaggtttttg  1020 ctaaatttt  ttgagtttat atttgtatgt cttatgctga aaaatcttgt ttcctaatta  1080
gtaacataat tattcatttg atgggtaaat attttagggc cgattcttg  gttttatagc  1140 caagataccc tgttgataaa gtcttgtggg agcaattata agactggctt attttgaagc  1200
tttttaaaaa agacatcctt acctgtttta actgtagatt atattaactt aaataggtac  1260
agcccacgct tgactagtcg ggtttgccgc cagaacacag gtaagtgccg tgtgtggttc  1320
ccgcgggcct ggcctcttta cgggttatgg cccttgcgtg ccttgaatta cttccacctg  1380
gctgcagtac gtgattcttg atcccgagct tcgggttgga agtgggtggg agagttcgag  1440
gccttgcgct taaggagccc cttcgcctcg tgcttgagtt gaggcctggc ctgggcgctg  1500
gggccgccgc gtgcgaatct ggtggcacct tcgcgcctgt ctcgctgctt tcgataagtc  1560
tctagccatt taaaattttt gatgacctgc tgcgacgctt tttttctggc aagatagtct  1620
tgtaaatgcg ggccaagatc tgcacactgg tatttcggtt tttggggccg cgggcggcga  1680
cggggcccgt gcgtcccagc gcacatgttc ggcgaggcgg ggcctgcgag cgcggccacc  1740
gagaatcgga cgggggtagt ctcaagctgg ccggcctgct ctggtgcctg gcctcgcgcc  1800
gccgtgtatc gccccgccct gggcggcaag gctggcccgg tcggcaccag ttgcgtgagc  1860
ggaaagatgg ccgcttcccg gccctgctgc agggagctca aaatggagga cgcggcgctc  1920
gggagagcgg gcgggtgagt cacccacaca aaggaaaagg cctttccgt  cctcagccgt  1980 cgcttcatgt gactccacgg agtaccgggc gccgtccagg cacctcgatt agttctcgag  2040
cttttggagt acgtcgtctt taggttgggg ggagggggttt tatgcgatgg agtttcccca  2100
cactgagtgg gtggagactg aagttaggcc agcttggcac ttgatgtaat tctccttgga  2160
atttgccctt tttgagtttg gatcttggtt cattctcaag cctcagacag tggttcaaag  2220
tttttttctt ccatttcag                                              2239
```

<210> SEQ ID NO 59
<211> LENGTH: 1647

<212> TYPE: DNA
<213> ORGANISM: Artificial Sequence
<220> FEATURE:
<223> OTHER INFORMATION: CMV-bActine-U2-mROSA

<400> SEQUENCE: 59

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tggtcgaggt gagccccacg ttctgcttca ctctccccat     360
ctccccccccc tccccacccc caattttgta tttatttatt ttttaattat tttgtgcagc    420
gatgggggcg ggggggggggg gggggcgcgc gccaggcggg gcggggcggg gcgaggggcg    480
gggcggggcg aggcggagag gtgcggcggc agccaatcag agcggcgcgc tccgaaagtt    540
tccttttatg gcgaggcggc ggcggcggcg gccctataaa aagcgaagcg cgcggcgggc    600
ggatccacta gtgtttaaac agagtaatga catggttcct tccatcctcc aaaggtgacc    660
aataatagtt tgtaagtatc attatgaact aatgaatttt caacatattt gatatatttc    720
aatccattgc catcattgtt cttatcgata tttgagttgg ctcactttgc cagtaagagt    780
ctattcaaat tggcttctga gtccatttga cacaacacct ttgatctttg acagtttcct    840
tggttttagg tgctagatga tttctcaggc tcaccttaga catttcctgc cacagactta    900
gaatcagcca tttctctaag gaccctgatt ccatttcatg agaaatgata gagaccacaa    960
tcaaaacaag tcatgaattt atactgatat tttcaattca aattaaagat gaggtttttg   1020
ctaaattttt ttgagtttat atttgtatgt cttatgctga aaaatcttgt ttcctaatta   1080
gtaacataat tattcatttg atgggtaaat attttagggc cgattcttty gttttatagc   1140
caagataccc tgttgataaa gtcttgtggg agcaattata agactggctt attttgaagc   1200
tttttaaaaa agacatcctt acctgtttta actgtagatt atattaactt aaataggtac   1260
agcccacgct tgactagttc agagagcctc ggctaggtag gggatcggga ctctggcggg   1320
agggcggctt ggtgcgtttg cggggatggg cggccgcggc aggccctccg agcgtggtgg   1380
agccgttctg tgagacagcc gggtacgagt cgtgacgctg gaaggggcaa gcgggtggtg   1440
ggcaggaatg cggtccgccc tgcagcaacc ggagggggag ggagaaggga gcggaaaagt   1500
ctccaccgga cgcggccatg gctcgggggg ggggggggcag cggaggagcg cttccggccg   1560
acgtctcgtc gctgattggc ttcttttcct cccgccgtgt gtgaaaacac aattgtacta   1620
accttcttct ctttcctctc ctgacag                                        1647
```

<210> SEQ ID NO 60
<211> LENGTH: 2514
<212> TYPE: DNA
<213> ORGANISM: Artificial Sequence
<220> FEATURE:
<223> OTHER INFORMATION: CMV-bActine-U2-hROSA

<400> SEQUENCE: 60

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
```

```
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tggtcgaggt gagccccacg ttctgcttca ctctccccat      360
ctcccccccc tccccacccc caattttgta tttatttatt ttttaattat tttgtgcagc      420 gatggggggcg ggggggggggg gggggcgcgc gccaggcggg gcggggcggg gcgaggggcg     480
gggcggggcg aggcggagag gtgcggcggc agccaatcag agcggcgcgc tccgaaagtt      540
tccttttatg gcgaggcggc ggcggcggcg gccctataaa aagcgaagcg cgcggcgggc      600
ggatccacta gtgtttaaac agagtaatga catggttcct tccatcctcc aaaggtgacc      660
aataatagtt tgtaagtatc attatgaact aatgaatttt caacatattt gatatatttc      720
aatccattgc catcattgtt cttatcgata tttgagttgg ctcactttgc cagtaagagt      780
ctattcaaat tggcttctga gtccatttga cacaacacct ttgatctttg acagtttcct      840
tggttttagg tgctagatga tttctcaggc tcaccttaga catttcctgc cacagactta      900
gaatcagcca tttctctaag gaccctgatt ccatttcatg agaaatgata gagaccacaa      960
tcaaaacaag tcatgaattt atactgtatt tttcaattca aattaaagat gaggtttttg     1020 ctaaatttt  ttgagtttat atttgtatgt cttatgctga aaaatcttgt ttcctaatta     1080
gtaacataat tattcatttg atgggtaaat attttagggc cgattctttg gttttatagc     1140
caagatcccc tgttgataaa gtcttgtggg agcaattata agactggctt attttgaagc     1200 ttttttaaaaa agacatcctt acctgtttta actgtagatt atattaactt aaataggtac    1260
agcccacgct tgactagtct cagagagcct cggctaggta ggggagcgga actctggtgg     1320
gaggggaggt gcggtgcact gggggatgg gtggctaggg gggccgtctg gtggcttgcg      1380
ggggttgcct ttcccgtggg aagtcgggaa cataatgttt gttacgttgg gagggaaagg     1440
ggtggctgga tgcaggcggg agggaggccc gccctgcggc aaccggaggg ggagggagaa     1500
gggagcggaa aatgctcgaa accggacgga gccattgctc tcgcagaggg aggagcgctt     1560
ccggctagcc tcttgtcgcc gattggccgt ttctcctccc gccgtgtgtg aaaacacaaa     1620
tggcgtattc tggttggagt aaagctcctg tcagttacac cgtcgggagt acgcagccgc     1680
ttagcgactc tcgcgttgcc ccctgggtgg ggcgggtagg taggtggggt gtagagatgc     1740
tgggtgtgcg ggcgcggccg gcctcctgcg gcggagggg agggtcagtg aaattggctc     1800
tggcgcgggc gtcctcccac cctcccttc cttcggggga gtcggtttac ccgccgcctg     1860
cttgtcttcg acacctgatt ggctgtcgaa gctgtgggac cgggcccttg ctactggctc     1920
gagtctcaca tgagcgaaac cactgcgcgg ggcgcggggg tggcgggag cgggcgttg     1980 gtacggtcct ccccgaggcc gagcgccgca gtgtctggcc ccgcgcccct cgcaacgtg     2040 gcaggaagcg cgcgctggag gcgggggcgg gctgccggcc gagacttctg gatggcggcg     2100
gccgcggctc cgccccgggt tcccaccgcc tgaaggcgga gacaagcccg acctgctaca     2160
ggcactcgtg ggggtggggg aggagcgggg gtcggtccgg ctggtttgtg ggtgggaggc     2220
gcttgttctc caaaaaccgg cgcgagctgc aatcctgagg gagctgcggt ggaggaggtg     2280
gagagaaggc cgcaccccttc tgggcagggg gagggagtg ccgcaatacc tttatgggag     2340
ttctttgctg cctcccgtct tgtaaggacc gccctgggcc tggaagaagc cctccctcct     2400
ttcctcctcg cgtgatctcg tcatcgcctc catgtcgagt cgcttctcga ttatgggcgg     2460
gattcttttg cctagacaat tgtactaacc ttcttctctt tcctctcctg acag          2514
```

<210> SEQ ID NO 61
<211> LENGTH: 1894
<212> TYPE: DNA
<213> ORGANISM: Artificial Sequence
<220> FEATURE:
<223> OTHER INFORMATION: CMV-bActine-U3-EF1

<400> SEQUENCE: 61

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tggtcgaggt gagcccacg ttctgcttca ctctccccat       360
ctccccccc tccccacccc caattttgta tttatttatt ttttaattat tttgtgcagc      420
gatggggcg gggggggggg ggggcgcgc gccaggcggg gcggggcggg gcgaggggcg       480
gggcggggcg aggcggagag gtgcggcggc agccaatcag agcggcgcgc tccgaaagtt    540
tccttttatg gcgaggcggc ggcggcgcg gccctataaa aagcgaagcg cgcggcgggc     600
ggatccgttt aacgctggtg gtagggatg agggagggag gggcattgtg atgtacaggg      660
ctgctctgtg agatcaaggg tctcttaagg gtgggagctg gggcagggac tacgagagca     720
gccagatggg ctgaaagtgg aactcaaggg gtttctggca cctacctacc tgcttcccgc     780
tggggggtgg ggagttggcc cagagtctta agattgggc agggtggaga ggtgggctct      840
tcctgcttcc cactcatctt atagctttct tccccagat ccgaattcga gatccaaacc      900
aaggaggaaa ggatatcaca gaggagagct agtcgggttt gccgccagaa cacaggtaag     960
tgccgtgtgt ggttcccgcg ggcctggcct ctttacgggt tatggccctt gcgtgccttg    1020
aattacttcc acctggctgc agtacgtgat tcttgatccc gagcttcggg ttggaagtgg    1080
gtgggagagt tcgaggcctt gcgcttaagg agccccttcg cctcgtgctt gagttgaggc    1140
ctggcctggg cgctgggcc gccgcgtgcg aatctggtgg caccttcgcg cctgtctcgc    1200
tgctttcgat aagtctctag ccatttaaaa tttttgatga cctgctgcga cgcttttttt    1260
ctggcaagat agtcttgtaa atgcgggcca agatctgcac actggtattt cggttttttgg   1320
ggccgcgggc ggcgacgggg cccgtgcgtc cagcgcaca tgttcggcga ggcggggcct    1380
gcgagcgcgg ccaccgagaa tcggacgggg gtagtctcaa gctggccggc ctgctctggt    1440
gcctggcctc gcgccgccgt gtatcgcccc gccctgggcg gcaaggctgg cccggtcggc   1500
accagttgcg tgagcggaaa gatggccgct tcccggccct gctgcaggga gctcaaaatg    1560
gaggacgcgg cgctcgggag agcgggcggg tgagtcaccc acacaaagga aaagggcctt   1620
tccgtcctca gccgtcgctt catgtgactc cacggagtac cgggcgccgt ccaggcacct    1680
cgattagttc tcgagctttt ggagtacgtc gtctttaggt tgggggggag ggttttatgc     1740
gatggagttt ccccacactg agtgggtgga gactgaagtt aggccagctt ggcacttgat   1800
gtaattctcc ttggaatttg cccttttga gtttggatct tggttcattc tcaagcctca    1860
gacagtggtt caaagtttt ttcttccatt tcag                                 1894
```

<210> SEQ ID NO 62
<211> LENGTH: 1302
<212> TYPE: DNA
<213> ORGANISM: Artificial Sequence
<220> FEATURE:

<223> OTHER INFORMATION: CMV-bActine-U3-mROSA

<400> SEQUENCE: 62

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tggtcgaggt gagccccacg ttctgcttca ctctccccat     360
ctccccccccc tccccacccc caattttgta tttatttatt ttttaattat tttgtgcagc    420
gatggggcg gggggggggg ggggcgcgc gccaggcggg gcgggcggg gcgaggggcg        480
gggcggggcg aggcggagag gtgcggcggc agccaatcag agcggcgcgc tccgaaagtt     540
tccttttatg gcgaggcggc ggcggcggcg gccctataaa aagcgaagcg cgcggcgggc     600
ggatccgttt aacgctggtg ggtagggatg agggagggag gggcattgtg atgtacaggg     660
ctgctctgtg agatcaaggg tctcttaagg gtgggagctg gggcagggac tacgagagca    720
gccagatggg ctgaaagtgg aactcaaggg gtttctggca cctacctacc tgcttcccgc    780
tgggggggtgg ggagttggcc cagagtctta agattgggc agggtggaga ggtgggctct    840
tcctgcttcc cactcatctt atagctttct ttccccagat ccgaattcga gatccaaacc    900
aaggaggaaa ggatatcaca gaggagagct agttcagaga gcctcggcta ggtaggggat    960
cgggactctg gcgggagggc ggcttggtgc gtttgcgggg atgggcggcc gcggcaggcc   1020
ctccgagcgt ggtggagccg ttctgtgaga cagccgggta cgagtcgtga cgctggaagg   1080
ggcaagcggg tggtgggcag gaatgcggtc cgccctgcag caaccggagg gggagggaga   1140
agggagcgga aaagtctcca ccggacgcgg ccatggctcg gggggggggg ggcagcggag   1200
gagcgcttcc ggccgacgtc tcgtcgctga ttggcttctt ttcctcccgc cgtgtgtgaa   1260
aacacaattg tactaacctt cttctctttc ctctcctgac ag                      1302
```

<210> SEQ ID NO 63
<211> LENGTH: 2169
<212> TYPE: DNA
<213> ORGANISM: Artificial Sequence
<220> FEATURE:
<223> OTHER INFORMATION: CMV-bActine-U3-hROSA

<400> SEQUENCE: 63

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg ggtcgcgaca tggtcgaggt gagccccacg ttctgcttca ctctccccat     360
ctccccccccc tccccacccc caattttgta tttatttatt ttttaattat tttgtgcagc    420
gatggggcg gggggggggg ggggcgcgc gccaggcggg gcgggcggg gcgaggggcg        480
gggcggggcg aggcggagag gtgcggcggc agccaatcag agcggcgcgc tccgaaagtt     540
tccttttatg gcgaggcggc ggcggcggcg gccctataaa aagcgaagcg cgcggcgggc     600
ggatccgttt aacgctggtg ggtagggatg agggagggag gggcattgtg atgtacaggg     660
```

```
ctgctctgtg agatcaaggg tctcttaagg gtgggagctg ggcagggac tacgagagca      720
gccagatggg ctgaaagtgg aactcaaggg gtttctggca cctacctacc tgcttcccgc      780
tgggggtgg ggagttggcc cagagtctta agattgggc agggtggaga ggtgggctct       840
tcctgcttcc cactcatctt atagctttct ttccccagat ccgaattcga gatccaaacc      900
aaggaggaaa ggatatcaca gaggagagct agtctcagag agcctcggct aggtagggga      960
gcggaactct ggtgggaggg gaggtgcggt gcactggggg gatgggtggc tagggggcc      1020
gtctggtggc ttgcggggt tgcctttccc gtgggaagtc gggaacataa tgtttgttac      1080
gttgggaggg aaaggggtgg ctggatgcag gcgggaggga ggcccgccct gcggcaaccg     1140
gaggggagg gagaagggag cggaaaatgc tcgaaaccgg acggagccat tgctctcgca     1200
gagggaggag cgcttccggc tagcctcttg tcgccgattg gccgtttctc ctcccgccgt     1260
gtgtgaaaac acaaatggcg tattctggtt ggagtaaagc tcctgtcagt tacaccgtcg    1320
ggagtacgca gccgcttagc gactctcgcg ttgcccctg ggtggggcgg gtaggtaggt     1380
ggggtgtaga gatgctgggt gtgcgggcgc ggccggcctc ctgcggcggg aggggagggt    1440
cagtgaaatt ggctctggcg cgggcgtcct cccacccctcc ccttccttcg ggggagtcgg   1500
tttacccgcc gcctgcttgt cttcgacacc tgattggctg tcgaagctgt gggaccgggc   1560
ccttgctact ggctcgagtc tcacatgagc gaaaccactg cgcggggcgc ggggttggcg   1620
gggaggcggg cgttggtacg gtcctccccg aggccgagcg ccgcagtgtc tggccccgcg   1680
cccctgcgca acgtgcagg aagcgcgcgc tggaggcggg ggcgggctgc cggccgagac    1740
ttctggatgg cggcggccgc ggctccgccc cgggttccca ccgcctgaag ggcgagacaa    1800
gcccgacctg ctacaggcac tcgtgggggt ggggaggag cggggtcgg tccggctggt     1860
ttgtgggtgg gaggcgcttg ttctccaaaa accggcgcga gctgcaatcc tgaggagct    1920
gcggtggagg aggtggagag aaggccgcac ccttctgggc aggggagggg gagtgccgca   1980
atacctttat gggagttctt tgctgcctcc cgtcttgtaa ggaccgccct gggcctggaa    2040
gaagccctcc ctcctttcct cctcgcgtga tctcgtcatc gcctccatgt cgagtcgctt    2100
ctcgattatg ggcgggattc ttttgcctag acaattgtac taaccttctt ctctttcctc    2160
tcctgacag                                                            2169
```

<210> SEQ ID NO 64
<211> LENGTH: 2514
<212> TYPE: DNA
<213> ORGANISM: Artificial Sequence
<220> FEATURE:
<223> OTHER INFORMATION: CMV-bActine-U1U2-EF1

<400> SEQUENCE: 64

```
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggcccg ggtcgcgaca tggtcgaggt gagccccacg ttctgcttca ctctccccat      360
ctcccccccc tccccacccc caattttgta tttatttatt ttttaattat tttgtgcagc      420
gatgggggcg ggggggggg ggggcgcgc gccaggcggg gcgggcggg gcgaggggcg         480
```

| | |
|---|---|
| gggcggggcg aggcggagag gtgcggcggc agccaatcag agcggcgcgc tccgaaagtt | 540 |
| tccttttatg gcgaggcggc ggcggcggcg gccctataaa aagcgaagcg cgcggcgggc | 600 |
| ggatccgttt aaacggctcg catctctcct tcacgcgccc gccgccctac ctgaggccgc | 660 |
| catccacgcc ggttgagtcg cgttctgccg cctcccgcct gtggtgcctc ctgaactgcg | 720 |
| tccgccgtct aggtaagttt aaagctcagg tcgagaccgg gcctttgtcc ggcgctccct | 780 |
| tggagcctac ctagactcag ccggctctcc acgctttgcc tgaccctgct tgctcaactc | 840 |
| tacgtctttg tttcgttttc tgttctgcgc cgttacagat cactagtgtt taaacagagt | 900 |
| aatgacatgg ttccttccat cctccaaagg tgaccaataa tagtttgtaa gtatcattat | 960 |
| gaactaatga attttcaaca tatttgatat atttcaatcc attgccatca ttgttcttat | 1020 |
| cgatatttga gttggctcac tttgccagta agagtctatt caaattggct tctgagtcca | 1080 |
| tttgacacaa cacctttgat ctttgacagt ttccttggtt ttaggtgcta gatgatttct | 1140 |
| caggctcacc ttagacattt cctgccacag acttagaatc agccatttct ctaaggaccc | 1200 |
| tgattccatt tcatgagaaa tgatagagac cacaatcaaa acaagtcatg aatttatact | 1260 |
| gatattttca attcaaatta aagatgaggt ttttgctaaa ttttttttgag tttatatttg | 1320 |
| tatgtcttat gctgaaaaat cttgtttcct aattagtaac ataattattc atttgatggg | 1380 |
| taaatatttt agggccgatt cttttggtttt atagccaaga taccctgttg ataaagtctt | 1440 |
| gtgggagcaa ttataagact ggcttatttt gaagcttttt aaaaaagaca tccttacctg | 1500 |
| ttttaactgt agattatatt aacttaaata ggtacagccc acgcttgact agtcgggttt | 1560 |
| gccgccagaa cacaggtaag tgccgtgtgt ggttcccgcg ggcctggcct ctttacgggt | 1620 |
| tatggccctt gcgtgccttg aattacttcc acctggctgc agtacgtgat tcttgatccc | 1680 |
| gagcttcggg ttggaagtgg gtgggagagt tcgaggcctt gcgcttaagg agccccttcg | 1740 |
| cctcgtgctt gagttgaggc ctggcctggg cgctggggcc gccgcgtgcg aatctggtgg | 1800 |
| caccttcgcg cctgtctcgc tgctttcgat aagtctctag ccatttaaaa tttttgatga | 1860 |
| cctgctgcga cgcttttttt ctggcaagat agtcttgtaa atgcgggcca agatctgcac | 1920 |
| actggtatttt cggttttttgg ggccgcggc ggcgacgggg cccgtgcgtc ccagcgcaca | 1980 |
| tgttcggcga ggcggggcct gcgagcgcgg ccaccgagaa tcggacgggg gtagtctcaa | 2040 |
| gctgccggc ctgctctggt gcctggcctc gcgccgccgt gtatcgcccc gcctgggcg | 2100 |
| gcaaggctgg cccggtcggc accagttgcg tgagcggaaa gatggccgct tcccggccct | 2160 |
| gctgcaggga gctcaaaatg gaggacgcg cgctcgggag agcgggcggg tgagtcaccc | 2220 |
| acacaaagga aaagggcctt tccgtcctca gccgtcgctt catgtgactc cacggagtac | 2280 |
| cgggcgccgt ccaggcacct cgattagttc tcgagctttt ggagtacgtc gtctttaggt | 2340 |
| tgggggagg ggttttatgc gatggagttt ccccacactg agtgggtgga gactgaagtt | 2400 |
| aggccagctt ggcacttgat gtaattctcc ttggaatttg ccctttttga gtttggatct | 2460 |
| tggttcattc tcaagcctca gacagtggtt caaagttttt tcttccatt tcag | 2514 |

<210> SEQ ID NO 65
<211> LENGTH: 1922
<212> TYPE: DNA
<213> ORGANISM: Artificial Sequence
<220> FEATURE:
<223> OTHER INFORMATION: CMV-bActine-U1U2-mROSA

<400> SEQUENCE: 65

| | |
|---|---|
| gcgttacata acttacggta aatggcccgc ctggctgacc gcccaacgac ccccgcccat | 60 |

```
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg ggtcgcgaca tggtcgaggt gagccccacg ttctgcttca ctctccccat    360 ctccccccccc tccccacccc caattttgta tttatttatt ttttaattat tttgtgcagc    420
gatgggggcg ggggggggg ggggcgcgc gccaggcggg gcggggcggg gcgaggggcg      480
gggcggggcg aggcggagag gtgcggcggc agccaatcag agcggcgcgc tccgaaagtt    540
tccttttatg gcgaggcggc ggcggcggcg gccctataaa aagcgaagcg cgcggcgggc    600
ggatccgttt aaacggctcg catctctcct tcacgcgccc gccgccctac ctgaggccgc    660
catccacgcc ggttgagtcg cgttctgccg cctcccgcct gtggtgcctc ctgaactgcg    720
tccgccgtct aggtaagttt aaagctcagg tcgagaccgg ccttttgtcc ggcgctccct    780
tggagcctac ctagactcag ccggctctcc acgctttgcc tgaccctgct tgctcaactc    840
tacgtctttg tttcgttttc tgttctgcgc cgttacagat cactagtgtt taaacagagt    900
aatgacatgg ttccttccat cctccaaagg tgaccaataa tagtttgtaa gtatcattat    960
gaactaatga tttttcaaca tatttgatat atttcaatcc attgccatca ttgttcttat   1020
cgatatttga gttggctcac tttgccagta agagtctatt caaattggct tctgagtcca   1080
tttgacacaa cacctttgat ctttgacagt tccttggtt ttaggtgcta gatgatttct     1140
caggctcacc ttagacattt cctgccacag acttagaatc agccatttct ctaaggaccc    1200
tgattccatt tcatgagaaa tgatagagac cacaatcaaa acaagtcatg aatttatact    1260
gatattttca attcaaatta aagatgaggt ttttgctaaa ttttttttgag tttatatttg    1320 tatgtcttat gctgaaaaat cttgtttcct aattagtaac ataattattc atttgatggg    1380 taaatattt agggccgatt cttggttttt atagccaaga taccctgttg ataaagtctt     1440
gtgggagcaa ttataagact ggcttatttt gaagcttttt aaaaaagaca tccttacctg    1500
ttttaactgt agattatatt aacttaaata ggtacagccc acgcttgact agttcagaga    1560
gcctcggcta ggtaggggat cgggactctg gcgggagggc ggcttggtgc gtttgcgggg    1620
atgggcggcc gcggcaggcc ctccgagcgt ggtggagccg ttctgtgaga cagccgggta    1680
cgagtcgtga cgctggaagg ggcaagcggg tggtgggcag gaatgcggtc cgccctgcag    1740
caaccggagg gggagggaga agggagcgga aaagtctcca ccggacgcgg ccatggctcg    1800 ggggggggg ggcagcggag gagcgcttcc ggccgacgtc tcgtcgctga ttggcttctt     1860
ttcctcccgc cgtgtgtgaa aacacaattg tactaacctt cttctctttc ctctcctgac    1920
ag                                                                  1922

<210> SEQ ID NO 66
<211> LENGTH: 2789
<212> TYPE: DNA
<213> ORGANISM: Artificial Sequence
<220> FEATURE:
<223> OTHER INFORMATION: CMV-bActine-U1U2-hROSA

<400> SEQUENCE: 66
gcgttacata acttacggta aatggcccgc ctggctgacc gcccaacgac ccccgcccat      60
tgacgtcaat aatgacgtat gttcccatag taacgccaat agggactttc cattgacgtc    120
```

```
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg ggtcgcgaca tggtcgaggt gagccccacg ttctgcttca ctctccccat    360
ctcccccccc tccccacccc caattttgta tttatttatt ttttaattat tttgtgcagc    420 gatggggcg gggggggggg ggggcgcgc gccaggcggg gcgggcggg gcgaggggcg       480 gggcggggcg aggcggagag gtgcggcggc agccaatcag agcggcgcgc tccgaaagtt    540 tcctttatg gcgaggcggc ggcggcgcg gccctataaa aagcgaagcg cgcggcgggc      600
ggatccgttt aaacggctcg catctctcct tcacgcgccc gccgcctac ctgaggccgc     660 catccacgcc ggttgagtcg cgttctgccg cctcccgcct gtggtgcctc ctgaactgcg    720
tccgccgtct aggtaagttt aaagctcagg tcgagaccgg gcctttgtcc ggcgctccct    780
tggagcctac ctagactcag ccggctctcc acgctttgcc tgaccctgct tgctcaactc    840
tacgtctttg tttcgttttc tgttctgcgc cgttacagat cactagtgtt taaacagagt    900
aatgacatgg ttccttccat cctccaaagg tgaccaataa tagtttgtaa gtatcattat    960
gaactaatga atttcaaca tatttgatat atttcaatcc attgccatca ttgttcttat    1020
cgatatttga gttggctcac tttgccagta agagtctatt caaattggct tctgagtcca    1080
tttgacacaa caccttgat ctttgacagt ttccttggtt ttaggtgcta gatgatttct     1140
caggctcacc ttagacattt cctgccacag acttagaatc agccatttct ctaaggaccc    1200
tgattccatt tcatgagaaa tgatagagac cacaatcaaa acaagtcatg aatttatact    1260
gatattttca attcaaatta aagatgaggt ttttgctaaa tttttttgag tttatatttg    1320
tatgtcttat gctgaaaaat cttgtttcct aattagtaac ataattattc atttgatggg    1380
taaatatttt agggccgatt ctttggtttt atagccaaga taccctgttg ataaagtctt    1440
gtgggagcaa ttataagact ggcttatttt gaagcttttt aaaaaagaca tccttacctg    1500
ttttaactgt agattatatt aacttaaata ggtacagccc acgcttgact agtctcagag    1560
agcctcggct aggtagggga gcggaactct ggtgggaggg gaggtgcggt gcactggggg    1620
gatgggtggc tagggggggcc gtctggtggc ttgcgggggt tgccttttccc gtgggaagtc  1680 gggaacataa tgtttgttac gttgggaggg aaaggggtgg ctggatgcag gcgggaggga   1740
ggcccgccct gcggcaaccg gagggggagg gagaagggag cggaaaatgc tcgaaaccgg   1800
acggagccat tgctctcgca gagggaggag cgcttccggc tagcctcttg tcgccgattg   1860
gccgtttctc ctcccgccgt gtgtgaaaac acaaatggcg tattctggtt ggagtaaagc   1920
tcctgtcagt tacaccgtcg ggagtacgca gccgcttagc gactctcgcg ttgccccctg   1980
ggtggggcgg gtaggtaggt ggggtgtaga gatgctgggt gtgcgggcgc ggccggcctc   2040
ctgcggcggg aggggagggt cagtgaaatt ggctctggcg cgggcgtcct cccaccctcc   2100
ccttccttcg ggggagtcgg tttacccgcc gcctgcttgt cttcgacacc tgattggctg   2160
tcgaagctgt gggaccgggc ccttgctact ggctcgagtc tcacatgagc gaaaccactg   2220
cgcggggcgc ggggtggcg gggaggcggg cgttggtacg gtcctccccg aggccgagcg   2280
ccgcagtgtc tggccccgcg cccctgcgca acgtggcagg aagcgcgcgc tggaggcggg   2340
ggcgggctgc cggccgagac ttctggatgg cggcggccgc ggctccgccc cgggttccca   2400
ccgcctgaag ggcgagacaa gcccgacctg ctacaggcac tcgtgggggt gggggaggag   2460
cgggggtcgg tccggctggt ttgtgggtgg gaggcgcttg ttctccaaaa accggcgcga   2520
```

```
gctgcaatcc tgagggagct gcggtggagg aggtggagag aaggccgcac ccttctgggc    2580
agggggaggg gagtgccgca ataccttat gggagttctt tgctgcctcc cgtcttgtaa     2640
ggaccgccct gggcctggaa gaagccctcc ctcctttcct cctcgcgtga tctcgtcatc    2700
gcctccatgt cgagtcgctt ctcgattatg ggcgggattc ttttgcctag acaattgtac    2760
taaccttctt ctctttcctc tcctgacag                                      2789
```

<210> SEQ ID NO 67
<211> LENGTH: 2172
<212> TYPE: DNA
<213> ORGANISM: Artificial Sequence
<220> FEATURE:
<223> OTHER INFORMATION: CMV-bActine-U1U3-EF1

<400> SEQUENCE: 67

```
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tggtcgaggt gagcccacg ttctgcttca ctctccccat      360
ctcccccccc tccccacccc caattttgta tttatttatt ttttaattat tttgtgcagc    420
gatgggggcg ggggggggg ggggcgcgc gccaggcggg gcgggcggg gcgaggggcg       480 gggcggggcg aggcggagag gtgcggcggc agccaatcag agcggcgcgc tccgaaagtt    540 tcctttatg gcgaggcggc ggcggcgcg gccctataaa aagcgaagcg cgcggcgggc      600
ggatccgttt aaacggctcg catctctcct tcacgcgccc gccgccctac ctgaggccgc    660
catccacgcc ggttgagtcg cgttctgccg cctcccgcct gtggtgcctc ctgaactgcg    720
tccgccgtct aggtaagttt aaagctcagg tcgagaccgg ccttgtcc ggcgctccct      780 tggagcctac ctagactcag ccggctctcc acgctttgcc tgaccctgct tgctcaactc    840
tacgtctttg tttcgttttc tgttctgcgc cgttacagat cactagttaa cgctggtggg    900
tagggatgag ggaggaggg gcattgtgat gtacagggct gctctgtgag atcaagggtc     960
tcttaagggt gggagctggg gcagggacta cgagagcagc cagatgggct gaaagtggaa    1020
ctcaaggggt ttctggcacc tacctacctg cttccgcctg ggggtgggg agttggccca    1080 gagtcttaag attggggcag ggtggagagg tgggctcttc ctgcttccca ctcatcttat    1140
agctttcttt ccccagatcc gaattcgaga tccaaaccaa ggaggaaagg atatcacaga    1200
ggagagctag tcgggtttgc cgccagaaca caggtaagtg ccgtgtgtgg ttcccgcggg    1260
cctggcctct ttacgggtta tggcccttgc gtgccttgaa ttacttccac ctggctgcag    1320
tacgtgattc ttgatcccga gcttcgggtt ggaagtgggt gggagagttc gaggccttgc    1380
gcttaaggag ccccttcgcc tcgtgcttga gttgaggcct ggcctgggcg ctggggccgc    1440
cgcgtgcgaa tctggtggca ccttcgcgcc tgtctcgctg ctttcgataa gtctctagcc    1500
atttaaaatt tttgatgacc tgctgcgacg ctttttttct ggcaagatag tcttgtaaat    1560
gcgggccaag atctgcacac tggtatttcg gtttttgggg ccgcgggcgg cgacggggcc    1620
cgtgcgtccc agcgcacatg ttcggcgagg cggggcctgc gagcgcggcc accgagaatc    1680 ggacggggt agtctcaagc tggccggcct gctctggtgc ctggcctcgc gccgccgtgt    1740
```

| | |
|---|---|
| atcgccccgc cctgggcggc aaggctggcc cggtcggcac cagttgcgtg agcggaaaga | 1800 |
| tggccgcttc ccggccctgc tgcagggagc tcaaaatgga ggacgcggcg ctcgggagag | 1860 |
| cgggcgggtg agtcacccac acaaaggaaa agggcctttc cgtcctcagc cgtcgcttca | 1920 |
| tgtgactcca cggagtaccg ggcgccgtcc aggcacctcg attagttctc gagcttttgg | 1980 |
| agtacgtcgt ctttaggttg gggggagggg ttttatgcga tggagtttcc ccacactgag | 2040 |
| tgggtggaga ctgaagttag gccagcttgg cacttgatgt aattctcctt ggaatttgcc | 2100 |
| cttttttgagt ttggatcttg gttcattctc aagcctcaga cagtggttca agttttttt | 2160 |
| cttccatttc ag | 2172 |

<210> SEQ ID NO 68
<211> LENGTH: 1580
<212> TYPE: DNA
<213> ORGANISM: Artificial Sequence
<220> FEATURE:
<223> OTHER INFORMATION: CMV-bActine-U1U3-mROSA

<400> SEQUENCE: 68

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tggtcgaggt gagccccacg ttctgcttca ctctccccat | 360 |
| ctccccccc tccccacccc caattttgta tttatttatt ttttaattat tttgtgcagc | 420 |
| gatggggcg gggggggggg ggggcgcgc gccaggcggg gcgggcggg gcgaggggcg | 480 |
| gggcggggcg aggcggagag gtgcggcggc agccaatcag agcggcgcgc tccgaaagtt | 540 |
| tcctttatg gcgaggcggc ggcggcgcg cccctataaa aagcgaagcg cgcggcgggc | 600 |
| ggatccgttt aaacggctcg catctctcct tcacgcgccc gccgccctac ctgaggccgc | 660 |
| catccacgcc ggttgagtcg cgttctgccg cctcccgcct gtggtgcctc ctgaactgcg | 720 |
| tccgccgtct aggtaagttt aaagctcagg tcgagaccgg gcctttgtcc ggcgctccct | 780 |
| tggagcctac ctagactcag ccggctctcc acgctttgcc tgaccctgct tgctcaactc | 840 |
| tacgtctttg tttcgttttc tgttctgcgc cgttacagat cactagttaa cgctggtggg | 900 |
| tagggatgag ggagggaggg gcattgtgat gtacagggct gctctgtgag atcaagggtc | 960 |
| tcttaagggt gggagctggg gcagggacta cgagagcagc cagatgggct gaaagtggaa | 1020 |
| ctcaaggggt ttctggcacc tacctacctg cttcccgctg gggggtgggg agttggccca | 1080 |
| gagtcttaag attgggcag ggtggagagg tgggctcttc ctgcttccca ctcatcttat | 1140 |
| agctttcttt ccccagatcc gaattcgaga tccaaaccaa ggaggaaagg atatcacaga | 1200 |
| ggagagctag ttcagagagc ctcggctagg taggggatcg ggactctggc gggagggcgg | 1260 |
| cttggtgcgt ttgcggggat gggcggccgc ggcaggccct ccgagcgtgg tggagccgtt | 1320 |
| ctgtgagaca gccgggtacg agtcgtgacg ctggaagggg caagcgggtg gtgggcagga | 1380 |
| atgcggtccg ccctgcagca accggagggg gagggagaag ggagcggaaa agtctccacc | 1440 |
| ggacgcggcc atggctcggg ggggggggg cagcggagga gcgcttccgg ccgacgtctc | 1500 |
| gtcgctgatt ggcttctttt cctccgccg tgtgtgaaaa cacaattgta ctaaccttct | 1560 |
| tctctttcct ctcctgacag | 1580 |

<210> SEQ ID NO 69
<211> LENGTH: 2447
<212> TYPE: DNA
<213> ORGANISM: Artificial Sequence
<220> FEATURE:
<223> OTHER INFORMATION: CMV-bActine-U1U3-hROSA

<400> SEQUENCE: 69

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgaca tggtcgaggt gagccccacg ttctgcttca ctctccccat      360
ctccccccc tccccacccc caattttgta tttatttatt ttttaattat tttgtgcagc     420
gatggggcg gggggggggg gggggcgcgc gccaggcggg gcgggcggg gcgaggggcg     480
gggcggggca aggcggagag gtgcggcggc agccaatcag agcggcgcgc tccgaaagtt     540
tcctttatg gcgaggcggc ggcggcggcg gccctataaa aagcgaagcg cgcggcgggc     600
ggatccgttt aaacggctcg catctctcct tcacgcgccc gccgccctac ctgaggccgc     660
catccacgcc ggttgagtcg cgttctgccg cctcccgcct gtggtgcctc ctgaactgcg     720
tccgccgtct aggtaagttt aaagctcagg tcgagaccgg cctttgtcc ggcgctccct      780
tggagcctac ctagactcag ccggctctcc acgctttgcc tgaccctgct tgctcaactc     840
tacgtctttg tttcgttttc tgttctgcgc cgttacagat cactagtaa cgctggtggg     900
tagggatgag ggagggaggg gcattgtgat gtacagggct gctctgtgag atcaagggtc     960
tcttaagggt gggagctggg gcagggacta cgagagcagc cagatgggct gaaagtggaa    1020
ctcaaggggt ttctggcacc tacctacctg cttcccgctg gggggtgggg agttggccca    1080
gagtcttaag attggggcag ggtggagagg tgggctcttc ctgcttccca ctcatcttat    1140
agctttcttt ccccagatcc gaattcgaga tccaaaccaa ggaggaaagg atatcacaga    1200
ggagagctag tctcagagag cctcggctag gtagggagc ggaactctgg tgggagggga    1260
ggtgcggtgc actgggggga tggtggcta gggggccgt ctggtggctt gcggggttg     1320
cctttcccgt gggaagtcgg gaacataatg tttgttacgt tgggagggaa aggggtggct    1380
ggatgcaggc gggagggagg cccgcccgtc ggcaaccgga gggggaggga aaggagcg     1440
gaaaatgctc gaaaccggac ggagccattg ctctcgcaga gggaggagcg cttccggcta    1500
gcctcttgtc gccgattggc cgtttctcct cccgccgtgt tgaaaacac aaatggcgta    1560
ttctggttgg agtaaagctc ctgtcagtta caccgtcggg agtacgcagc cgcttagcga    1620
ctctcgcgtt gccccctggg tggggcgggt aggtaggtgg ggtgtagaga tgctgggtgt    1680
gcgggcgcgg ccggcctcct gcggcgggag gggagggtca gtgaaattgg ctctggcgcg    1740
ggcgtcctcc caccctcccc ttccttcggg ggagtcggtt tacccgccgc ctgcttgtct    1800
tcgacacctg attggctgtc gaagctgtgg gaccgggccc ttgctactgg ctcgagtctc    1860
acatgagcga aaccactgcg cggggcgcgg gggtggcggg gagggcggcg ttggtacggt    1920
cctccccgag gccgagcgcc gcagtgtctg gccccgcgcc cctgcgcaac gtggcaggaa    1980
gcgcgcgctg gaggcggggg cgggctgccg gccgagactt ctggatggcg gcggccgcgg    2040
```

| | |
|---|---|
| ctccgccccg ggttcccacc gcctgaaggg cgagacaagc ccgacctgct acaggcactc | 2100 |
| gtggggggtgg gggaggagcg ggggtcggtc cggctggttt gtgggtggga ggcgcttgtt | 2160 |
| ctccaaaaac cggcgcgagc tgcaatcctg agggagctgc ggtggaggag gtggagagaa | 2220 |
| ggccgcaccc ttctgggcag ggggagggga gtgccgcaat acctttatgg gagttctttg | 2280 |
| ctgcctcccg tcttgtaagg accgccctgg gcctggaaga agccctccct cctttcctcc | 2340 |
| tcgcgtgatc tcgtcatcgc ctccatgtcg agtcgcttct cgattatggg cgggattctt | 2400 |
| ttgcctagac aattgtacta accttcttct ctttcctctc ctgacag | 2447 |

<210> SEQ ID NO 70
<211> LENGTH: 2557
<212> TYPE: DNA
<213> ORGANISM: Artificial Sequence
<220> FEATURE:
<223> OTHER INFORMATION: CMV-bActine-U2U3-EF1

<400> SEQUENCE: 70

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg gtcgcgaca tggtcgaggt gagccccacg ttctgcttca ctctccccat | 360 |
| ctccccccc tccccacccc caattttgta tttatttatt ttttaattat tttgtgcagc | 420 |
| gatggggcg gggggggggg ggggcgcgc gccaggcggg gcgggcggg gcgaggggcg | 480 |
| gggcggggcg aggcggagag gtgcggcggc agccaatcag agcggcgcgc tccgaaagtt | 540 |
| tccttttatg gcgaggcggc ggcggcggcg gccctataaa aagcgaagcg cgcggcgggc | 600 |
| ggatccgttt aaacagagta atgacatggt tccttccatc ctccaaaggt gaccaataat | 660 |
| agtttgtaag tatcattatg aactaatgaa ttttcaacat atttgatata tttcaatcca | 720 |
| ttgccatcat tgttcttatc gatatttgag ttggctcact ttgccagtaa gagtctattc | 780 |
| aaattggctt ctgagtccat ttgacacaac acctttgatc tttgacagtt ccttggtttt | 840 |
| taggtgctag atgatttctc aggctcacct tagacatttc ctgccacaga cttagaatca | 900 |
| gccatttctc taaggaccct gattccattt catgagaaat gatagagacc acaatcaaaa | 960 |
| caagtcatga atttatactg atattttcaa ttcaaattaa agatgaggtt tttgctaaat | 1020 |
| tttttttgagt ttatatttgt atgtcttatg ctgaaaaatc ttgttttccta attagtaaca | 1080 |
| taattattca tttgatgggt aaatatttta gggccgattc ttttggtttta tagccaagat | 1140 |
| accctgttga taaagtcttg tgggagcaat tataagactg gcttatttg aagcttttta | 1200 |
| aaaaagacat ccttacctgt tttaactgta gattatatta acttaaatag gtacagccca | 1260 |
| cgcttgacta gttaacgctg gtgggtaggg atgaggagg gagggcatt gtgatgtaca | 1320 |
| gggctgctct gtgagatcaa gggtctctta agggtgggag ctgggcagg gactacgaga | 1380 |
| gcagccagat gggctgaaag tggaactcaa ggggtttctg gcacctacct acctgcttcc | 1440 |
| cgctgggggg tggggagttg gcccagagtc ttaagattgg ggcagggtgg agaggtgggc | 1500 |
| tcttcctgct tcccactcat cttatagctt tctttcccca gatccgaatt cgagatccaa | 1560 |
| accaaggagg aaaggatatc acagaggaga gctagtcggg tttgccgcca gaacacaggt | 1620 |
| aagtgccgtg tgtggttccc gcgggcctgg cctctttacg ggttatggcc cttgcgtgcc | 1680 |

```
ttgaattact tccacctggc tgcagtacgt gattcttgat cccgagcttc gggttggaag    1740
tgggtgggag agttcgaggc cttgcgctta aggagcccct tcgcctcgtg cttgagttga    1800
ggcctggcct gggcgctggg gccgccgcgt gcgaatctgg tggcaccttc gcgcctgtct    1860
cgctgctttc gataagtctc tagccattta aaattttga tgacctgctg cgacgctttt    1920
tttctggcaa gatagtcttg taaatgcggg ccaagatctg cacactggta tttcggtttt    1980
tggggccgcg ggcggcgacg gggcccgtgc gtcccagcgc acatgttcgg cgaggcgggg    2040
cctgcgagcg cggccaccga gaatcggacg ggggtagtct caagctggcc ggcctgctct    2100
ggtgcctggc ctcgcgccgc cgtgtatcgc cccgccctgg gcggcaaggc tggcccggtc    2160
ggcaccagtt gcgtgagcgg aaagatggcc gcttcccggc cctgctgcag ggagctcaaa    2220
atggaggacg cggcgctcgg gagagcgggc gggtgagtca cccacacaaa ggaaaagggc    2280
ctttccgtcc tcagccgtcg cttcatgtga ctccacggag taccgggcgc cgtccaggca    2340
cctcgattag ttctcgagct tttggagtac gtcgtcttta ggttgggggg aggggtttta    2400
tgcgatggag tttccccaca ctgagtgggt ggagactgaa gttaggccag cttggcactt    2460
gatgtaattc tccttggaat ttgccctttt tgagtttgga tcttggttca ttctcaagcc    2520
tcagacagtg gttcaaagtt tttttcttcc atttcag                             2557
```

<210> SEQ ID NO 71
<211> LENGTH: 1965
<212> TYPE: DNA
<213> ORGANISM: Artificial Sequence
<220> FEATURE:
<223> OTHER INFORMATION: CMV-bActine-U2U3-mROSA

<400> SEQUENCE: 71

```
gcgttacata acttacggta aatggcccgc ctggctgacc gcccaacgac ccccgcccat      60
tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatggcccg gtcgcgacca tggtcgaggt gagccccacg ttctgcttca ctctccccat     360 ctccccccc tccccacccc caattttgta tttatttatt ttttaattat tttgtgcagc     420 gatggggggcg gggggggggg gggggcgcgc gccaggcggg gcggggcggg gcgaggggcg     480
gggcggggcg aggcggagag gtgcggcggc agccaatcag agcggcgcgc tccgaaagtt     540
tccttttatg gcgaggcggc ggcggcggcg gccctataaa aagcgaagcg cgcggcgggc     600
ggatccgttt aaacagagta atgacatggt tccttccatc ctccaaaggt gaccaataat     660
agtttgtaag tatcattatg aactaatgaa ttttcaacat atttgatata tttcaatcca     720
ttgccatcat tgttcttatc gatatttgag ttggctcact ttgccagtaa gagtctattc     780
aaattggctt ctgagtccat ttgacacaac acctttgatc tttgacagtt tccttggttt     840
taggtgctag atgatttctc aggctcacct tagacatttc ctgccacaga cttagaatca     900
gccatttctc taaggaccct gattccattt catgagaaat gatagagacc acaatcaaaa     960
caagtcatga atttatactg atattttcaa ttcaaattaa agatgaggtt tttgctaaat    1020
ttttttgagt ttatatttgt atgtcttatg ctgaaaaatc ttgttcccta attagtaaca    1080
taattattca tttgatgggt aaatatttta gggccgattc tttggtttta tagccaagat    1140
```

```
accctgttga taaagtcttg tgggagcaat tataagactg gcttattttg aagcttttta    1200
aaaaagacat ccttacctgt tttaactgta gattatatta acttaaatag gtacagccca    1260
cgcttgacta gttaacgctg gtgggtaggg atgagggagg gaggggcatt gtgatgtaca    1320
gggctgctct gtgagatcaa gggtctctta agggtgggag ctgggcagg gactacgaga     1380 gcagccagat gggctgaaag tggaactcaa ggggtttctg gcacctacct acctgcttcc    1440
cgctgggggg tggggagttg gcccagagtc ttaagattgg ggcagggtgg agaggtgggc    1500
tcttcctgct tcccactcat cttatagctt tctttcccca gatccgaatt cgagatccaa    1560
accaaggagg aaaggatatc acagaggaga gctagttcag agagcctcgg ctaggtaggg    1620
gatcgggact ctggcgggag ggcggcttgg tgcgtttgcg gggatgggcg gccgcggcag    1680
gccctccgag cgtggtggag ccgttctgtg agacagccgg gtacgagtcg tgacgctgga    1740
aggggcaagc gggtggtggg caggaatgcg gtccgccctg cagcaaccgg aggggagg    1800 agaagggagc ggaaaagtct ccaccggacg cggccatggc tcgggggggg ggggcagcg    1860 gaggagcgct tccggccgac gtctcgtcgc tgattggctt cttttcctcc cgccgtgtgt    1920
gaaaacacaa ttgtactaac cttcttctct ttcctctcct gacag                   1965

<210> SEQ ID NO 72
<211> LENGTH: 2832
<212> TYPE: DNA
<213> ORGANISM: Artificial Sequence
<220> FEATURE:
<223> OTHER INFORMATION: CMV-bActine-U2U3-hROSA

<400> SEQUENCE: 72
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tggtcgaggt gagcccacg ttctgcttca ctctccccat      360 ctccccccccc tccccacccc caatttttgta tttatttatt ttttaattat tttgtgcagc  420
gatgggggcg ggggggggg ggggcgcgc gccaggcggg gcggggcggg gcgaggggcg      480
gggcggggcg aggcggagag gtgcggcggc agccaatcag agcggcgcgc tccgaaagtt    540
tccttttatg gcgaggcggc ggcggcgcg gccctataaa aagcgaagcg cgcggcgggc     600
ggatccgttt aaacagagta atgacatggt tccttccatc ctccaaaggt gaccaataat    660
agtttgtaag tatcattatg aactaatgaa ttttcaacat atttgatata tttcaatcca    720
ttgccatcat tgttcttatc gatatttgag ttggctcact ttgccagtaa gagtctattc    780
aaattggctt ctgagtccat ttgacacaac cctttgatc tttgacagtt tccttggttt     840
taggtgctag atgatttctc aggctcacct tagacatttc ctgccacaga cttagaatca    900
gccatttctc taaggaccct gattccattt catgagaaat gatagagacc acaatcaaaa    960
caagtcatga atttatactg atattttcaa ttcaaattaa agatgaggtt tttgctaaat    1020
ttttttgagt ttatatttgt atgtcttatg ctgaaaaatc ttgtttccta attagtaaca    1080
taattattca tttgatgggt aaatatttta gggccgattc tttggttta tagccaagat     1140 accctgttga taaagtcttg tgggagcaat tataagactg gcttattttg aagcttttta    1200
aaaaagacat ccttacctgt tttaactgta gattatatta acttaaatag gtacagccca    1260
```

```
cgcttgacta gttaacgctg gtgggtaggg atgagggagg gaggggcatt gtgatgtaca   1320
gggctgctct gtgagatcaa gggtctctta agggtgggag ctgggcagg gactacgaga    1380 gcagccagat gggctgaaag tggaactcaa ggggtttctg gcacctacct acctgcttcc   1440 cgctggggggg tgggagttg gcccagagtc ttaagattgg ggcagggtgg agaggtgggc   1500
tcttcctgct tcccactcat cttatagctt tctttcccca gatccgaatt cgagatccaa   1560
accaaggagg aaaggatatc acagaggaga gctagtctca gagagcctcg gctaggtagg   1620
ggagcggaac tctggtggga ggggaggtgc ggtgcactgg ggggatgggt ggctaggggg   1680
gccgtctggt ggcttgcggg ggttgccttt cccgtgggaa gtcgggaaca taatgtttgt   1740
tacgttggga gggaaggggg tggctggatg caggcgggag ggaggcccgc cctgcggcaa   1800
ccggaggggg agggagaagg gagcggaaaa tgctcgaaac cggacggagc cattgctctc   1860
gcagagggag gagcgcttcc ggctagcctc ttgtcgccga ttggccgttt ctcctcccgc   1920
cgtgtgtgaa acacaaatg gcgtattctg gttggagtaa agctcctgtc agttacaccg    1980
tcgggagtac gcagccgctt agcgactctc gcgttgcccc ctgggtgggg cgggtaggta   2040
ggtggggtgt agagatgctg ggtgtgcggg gcgccggccggc ctcctgcggc gggaggggag  2100
ggtcagtgaa attggctctg gcgcgggcgt cctcccaccc tccccttcct tcgggggagt   2160
cggtttaccc gccgcctgct tgtcttcgac acctgattgg ctgtcgaagc tgtgggaccg   2220
ggcccttgct actggctcga gtctcacatg agcgaaacca ctgcgcgggg cgcgggggtg   2280
gcggggaggc gggcgttggt acggtcctcc ccgaggccga gcgccgcagt gtctggcccc   2340
gcgcccctgc gcaacgtggc aggaagcgcg cgctggaggc ggggcgggc tgccggccga    2400 gacttctgga tggcgcggc cgcggctccg ccccgggttc ccaccgcctg aagggcgaga   2460
caagcccgac ctgctacagg cactcgtggg ggtggggag gagcgggggt cggtccggct    2520
ggtttgtggg tgggaggcgc ttgttctcca aaaaccggcg cgagctgcaa tcctgaggga   2580
gctgcggtgg aggaggtgga gagaaggccg cacccttctg ggcaggggga ggggagtgcc   2640
gcaatacctt tatgggagtt ctttgctgcc tcccgtcttg taaggaccgc cctgggcctg   2700
gaagaagccc tccctccttt cctcctcgcg tgatctcgtc atcgcctcca tgtcgagtcg   2760
cttctcgatt atgggcggga ttcttttgcc tagacaattg tactaaccct cttctctttc   2820
ctctcctgac ag                                                      2832

<210> SEQ ID NO 73
<211> LENGTH: 2838
<212> TYPE: DNA
<213> ORGANISM: Artificial Sequence
<220> FEATURE:
<223> OTHER INFORMATION: CMV-bActine-U1U2U3-EF1

<400> SEQUENCE: 73
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatggcccg gtcgcgaca tggtcgaggt gagccccacg ttctgcttca ctctccccat    360 ctccccccccc tccccacccc caatttttgta tttatttatt ttttaattat tttgtgcagc  420
```

```
gatggggcg ggggggggg gggggcgcgc gccaggcggg gcggggcggg gcgaggggcg    480
gggcggggcg aggcggagag gtgcggcggc agccaatcag agcggcgcgc tccgaaagtt   540
tccttttatg gcgaggcggc ggcggcggcg gccctataaa aagcgaagcg cgcggcgggc   600
ggatccgttt aaacggctcg catctctcct tcacgcgccc gccgcccTac ctgaggccgc   660
catccacgcc ggttgagtcg cgttctgccg cctcccgcct gtggtgcctc ctgaactgcg   720
tccgccgtct aggtaagttt aaagctcagg tcgagaccgg gcctttgtcc ggcgctccct   780
tggagcctac ctagactcag ccggctctcc acgctttgcc tgaccctgct tgctcaactc   840
tacgtctttg tttcgttttc tgttctgcgc cgttacagat cactagtgtt taaacagagt   900
aatgacatgg ttccttccat cctccaaagg tgaccaataa tagtttgtaa gtatcattat   960
gaactaatga atttTcaaca tatttgatat atttcaatcc attgccatca ttgttcttat  1020
cgatatttga gttggctcac tttgccagta agagtctatt caaattggct tctgagtcca  1080
tttgacacaa cacctttgat ctttgacagt ttccttggtt ttaggtgcta gatgatttct  1140
caggctcacc ttagacattt cctgccacag acttagaatc agccatttct ctaaggaccc  1200
tgattccatt tcatgagaaa tgatagagac cacaatcaaa acaagtcatg aatttatact  1260
gatattttca attcaaatta aagatgaggt ttttgctaaa tttttttgag tttatatttg  1320
tatgtcttat gctgaaaaat cttgtttcct aattagtaac ataattattc atttgatggg  1380
taaatatttt agggccgatt ctttggtttt atagccaaga tacccTgttg ataaagtctt  1440
gtgggagcaa ttataagact ggcttatttt gaagcttttt aaaaaagaca tccttacctg  1500
ttttaactgt agattatatt aacttaaata ggtacagccc acgcttgact agttaacgct  1560
ggtgggtagg gatgagggag ggagggggcat tgtgatgtac agggctgctc tgtgagatca  1620
agggtctctt aagggtggga gctggggcag ggactacgag agcagccaga tgggctgaaa  1680
gtggaactca aggggtttct ggcacctacc tacctgcttc ccgctggggg gtggggagtt  1740
ggcccagagt cttaagattg gggcagggtg gagaggtggg ctcttcctgc ttcccactca  1800
tcttatagct ttcttTcccc agatccgaat tcgagatcca aaccaaggag gaaaggatat  1860
cacagaggag agctagtcgg gtttgccgcc agaacacagg taagtgccgt gtgtggttcc  1920
cgcgggcctg gcctctttac gggttatggc ccttgcgtgc cttgaattac ttccacctgg  1980
ctgcagtacg tgattcttga tcccgagctt cgggttggaa gtgggtggga gagttcgagg  2040
ccttgcgctt aaggagcccc ttcgcctcgt gcttgagttg aggcctggcc tgggcgctgg  2100
ggccgccgcg tgcgaatctg gtggcacctt cgcgcctgtc tcgctgcttt cgataagtct  2160
ctagccattt aaaattttTg atgacctgct gcgacgcttt ttttctggca agatagtctt  2220
gtaaatgcgg gccaagatct gcacactggt atttcggttt ttggggccgc gggcggcgac  2280
ggggcccgtg cgtcccagcg cacatgttcg gcgaggcggg gcctgcgagc gcggccaccg  2340
agaatcggac gggggtagtc tcaagctggc cggcctgctc tggtgcctgg cctcgcgccg  2400
ccgtgtatcg ccccgccctg ggcggcaagg ctggcccggt cggcaccagt tgcgtgagcg  2460
gaaagatggc cgcttcccgg ccctgctgca gggagctcaa aatggaggac gcggcgctcg  2520
ggagagcggg cgggtgagtc acccacacaa aggaaaaggg cctttccgtc ctcagccgtc  2580
gcttcatgtg actccacgga gtaccgggcg ccgtccaggc acctcgatta gttctcgagc  2640
ttttggagta cgtcgtcttt aggttggggg gaggggtttt atgcgatgga gtttccccac  2700
actgagtggg tggagactga agttaggcca gcttggcact tgatgtaatt ctccttggaa  2760
tttgcccttt ttgagtttgg atcttggttc attctcaagc ctcagacagt ggttcaaagt  2820
```

```
tttttttcttc catttcag                                              2838

<210> SEQ ID NO 74
<211> LENGTH: 2246
<212> TYPE: DNA
<213> ORGANISM: Artificial Sequence
<220> FEATURE:
<223> OTHER INFORMATION: CMV-bActine-U1U2U3-mROSA

<400> SEQUENCE: 74
gcgttacata acttacggta aatggcccgc ctggctgacc gcccaacgac ccccgcccat    60
tgacgtcaat aatgacgtat gttcccatag taacgccaat agggactttc cattgacgtc   120
aatgggtgga gtatttacgg taaactgccc acttggcagt acatcaagtg tatcatatgc   180
caagtacgcc ccctattgac gtcaatgacg gtaaatggcc cgcctggcat tatgcccagt   240
acatgacctt atgggacttt cctacttggc agtacatcta cgtattagtc atcgctatta   300
ccatggcccg gtcgcgaca tggtcgaggt gagccccacg ttctgcttca ctctccccat   360 ctccccccccc tccccacccc caattttgta tttatttatt ttttaattat tttgtgcagc   420
gatgggggcg ggggggggg ggggcgcgc gccaggcggg gcgggcggg gcgaggggcg   480 ggcggggcg aggcggagag gtgcggcggc agccaatcag agcggcgcgc tccgaaagtt   540
tccttttatg gcgaggcggc ggcggcgcg gccctataaa aagcgaagcg cgcggcgggc   600
ggatccgttt aaacggctcg catctctcct tcacgcgccc gccgcctac ctgaggccgc   660 catccacgcc ggttgagtcg cgttctgccg cctcccgcct gtggtgcctc ctgaactgcg   720
tccgccgtct aggtaagttt aaagctcagg tcgagaccgg gcctttgtcc ggcgctccct   780
tggagcctac ctagactcag ccggctctcc acgctttgcc tgaccctgct tgctcaactc   840
tacgtctttg tttcgtttc tgttctgcgc cgttacagat cactagtgtt taaacagagt   900
aatgacatgg ttccttccat cctccaaagg tgaccaataa tagtttgtaa gtatcattat   960
gaactaatga attttcaaca tatttgatat atttcaatcc attgccatca ttgttcttat  1020
cgatatttga gttggctcac tttgccagta agagtctatt caaattggct tctgagtcca  1080
tttgacacaa cacctttgat cttgtgacagt ttccttggtt ttaggtgcta gatgatttct  1140
caggctcacc ttagacattt cctgccacag acttagaatc agccatttct ctaaggaccc  1200
tgattccatt tcatgagaaa tgatagagac cacaatcaaa acaagtcatg aatttatact  1260
gatattttca attcaaatta aagatgaggt ttttgctaaa ttttttttgag tttatatttg  1320 tatgtcttat gctgaaaaat cttgtttcct aattagtaac ataattattc atttgatggg  1380
taaatatttt agggccgatt ctttggtttt atagccaaga taccctgttg ataaagtctt  1440
gtgggagcaa ttataagact ggcttatttt gaagcttttt aaaaaagaca tccttacctg  1500
ttttaactgt agattatatt aacttaaata ggtacagccc acgcttgact agttaacgct  1560
ggtgggtagg gatgagggag ggaggggcat tgtgatgtac agggctgctc tgtgagatca  1620
agggtctctt aagggtggga gctggggcag ggactacgag agcagccaga tgggctgaaa  1680
gtggaactca agggggtttct ggcacctacc tacctgcttc ccgctggggg gtggggagtt  1740
ggcccagagt cttaagattg gggcagggtg gagaggtggg ctcttcctgc ttcccactca  1800
tcttatagct ttcttttcccc agatccgaat tcgagatcca aaccaaggag gaaaggatat  1860
cacagaggag agctagttca gagagcctcg gctaggtagg ggatcgggac tctgcgggga  1920
gggcggcttg gtgcgtttgc ggggatgggc ggccgcggca ggccctccga gcgtggtgga  1980
```

| | |
|---|---|
| gccgttctgt gagacagccg ggtacgagtc gtgacgctgg aaggggcaag cgggtggtgg | 2040 |
| gcaggaatgc ggtccgccct gcagcaaccg gaggggagg gagaagggag cggaaaagtc | 2100 |
| tccaccggac gcggccatgg ctcgggggg ggggggcagc ggaggagcgc ttccggccga | 2160 |
| cgtctcgtcg ctgattggct tcttttcctc ccgccgtgtg tgaaaacaca attgtactaa | 2220 |
| ccttcttctc tttcctctcc tgacag | 2246 |

<210> SEQ ID NO 75
<211> LENGTH: 3113
<212> TYPE: DNA
<213> ORGANISM: Artificial Sequence
<220> FEATURE:
<223> OTHER INFORMATION: CMV-bActine-U1U2U3-hROSA

<400> SEQUENCE: 75

| | |
|---|---|
| gcgttacata acttacggta aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggacttt cctacttggc agtacatcta cgtattagtc atcgctatta | 300 |
| ccatggcccg ggtcgcgaca tggtcgaggt gagccccacg ttctgcttca ctctccccat | 360 |
| ctccccccc tccccacccc caattttgta tttatttatt ttttaattat tttgtgcagc | 420 |
| gatggggcg ggggggggg gggggcgcgc gccaggcggg gcgggcggg gcgaggggcg | 480 |
| gggcggggcg aggcggagag gtgcggcggc agccaatcag agcggcgcgc tccgaaagtt | 540 |
| tccttttatg gcgaggcggc ggcggcggcg gccctataaa aagcgaagcg cgcggcgggc | 600 |
| ggatccgttt aaacggctcg catctctcct tcacgcgccc gccgccctac ctgaggccgc | 660 |
| catccacgcc ggttgagtcg cgttctgccg cctcccgcct gtggtgcctc ctgaactgcg | 720 |
| tccgccgtct aggtaagttt aaagctcagg tcgagaccgg gcctttgtcc ggcgctccct | 780 |
| tggagcctac ctagactcag ccggctctcc acgctttgcc tgaccctgct tgctcaactc | 840 |
| tacgtctttg tttcgttttc tgttctgcgc cgttacagat cactagtgtt taaacagagt | 900 |
| aatgacatgg ttccttccat cctccaaagg tgaccaataa tagtttgtaa gtatcattat | 960 |
| gaactaatga attttcaaca tatttgatat atttcaatcc attgccatca ttgttccttat | 1020 |
| cgatatttga gttggctcac tttgccagta agagtctatt caaattggct tctgagtcca | 1080 |
| tttgacacaa cacctttgat cttttgacagt ttccttggtt ttaggtgcta gatgatttct | 1140 |
| caggctcacc ttagacattt cctgccacag acttagaatc agccatttct ctaaggaccc | 1200 |
| tgattccatt tcatgagaaa tgatagagac cacaatcaaa acaagtcatg aatttatact | 1260 |
| gatatttttca attcaaatta aagatgaggt ttttgctaaa ttttttttgag tttatatttg | 1320 |
| tatgtcttat gctgaaaaat cttgtttcct aattagtaac ataattattc atttgatggg | 1380 |
| taaatatttt agggccgatt ctttggtttt atagccaaga taccctgttg ataaagtctt | 1440 |
| gtgggagcaa ttataagact ggcttatttt gaagcttttt aaaaaagaca tccttacctg | 1500 |
| ttttaactgt agattatatt aacttaaata ggtacagccc acgcttgact agttaacgct | 1560 |
| ggtgggtagg gatgagggag ggaggggcat tgtgatgtac agggctgctc tgtgagatca | 1620 |
| aggtctctt aagggtggga gctgggcag ggactacgag agcagccaga tgggctgaaa | 1680 |
| gtggaactca aggggtttct ggcacctacc tacctgcttc ccgctggggg gtggggagtt | 1740 |
| ggcccagagt cttaagattg gggcagggtg gagaggtggg ctcttcctgc ttcccactca | 1800 |

```
tcttatagct ttctttcccc agatccgaat tcgagatcca aaccaaggag gaaaggatat    1860
cacagaggag agctagtctc agagagcctc ggctaggtag gggagcggaa ctctggtggg    1920
aggggaggtg cggtgcactg gggggatggg tggctagggg ggccgtctgg tggcttgcgg    1980
gggttgcctt tcccgtggga agtcgggaac ataatgtttg ttacgttggg agggaaaggg    2040
gtggctggat gcaggcggga gggaggcccg ccctgcggca accggagggg gagggagaag    2100
ggagcggaaa atgctcgaaa ccggacggag ccattgctct cgcagaggga ggagcgcttc    2160
cggctagcct cttgtcgccg attggccgtt tctcctcccg ccgtgtgtga aaacacaaat    2220
ggcgtattct ggttggagta aagctcctgt cagttacacc gtcgggagta cgcagccgct    2280
tagcgactct cgcgttgccc cctgggtggg gcgggtaggt aggtggggtg tagagatgct    2340
gggtgtgcgg gcgcggccgg cctcctgcgg cgggagggga gggtcagtga aattggctct    2400
ggcgcgggcg tcctcccacc ctcccccttcc ttcggggggag tcggtttacc cgccgcctgc    2460
ttgtcttcga cacctgattg gctgtcgaag ctgtgggacc gggcccttgc tactggctcg    2520
agtctcacat gagcgaaacc actgcgcggg gcgcggggt ggcggggagg cgggcgttgg    2580
tacggtcctc cccgaggccg agcgccgcag tgtctggccc cgcgcccctg cgcaacgtgg    2640
caggaagcgc gcgctggagg cggggcggg ctgccggccg agacttctgg atggcggcgg    2700
ccgcggctcc gccccgggtt cccaccgcct gaagggcgag acaagcccga cctgctacag    2760
gcactcgtgg gggtgggga ggagcggggg tcggtccggc tggtttgtgg gtgggaggcg    2820
cttgttctcc aaaaaccggc gcgagctgca atcctgaggg agctgcggtg gaggaggtgg    2880
agagaaggcc gcaccttct gggcaggggg aggggagtgc cgcaatacct ttatgggagt    2940
tctttgctgc ctcccgtctt gtaaggaccg ccctgggcct ggaagaagcc ctccctcctt    3000
tcctcctcgc gtgatctcgt catcgcctcc atgtcgagtc gcttctcgat tatgggcggg    3060
attcttttgc ctagacaatt gtactaacct tcttctctttt cctctcctga cag          3113
```

TRANSCRIPTION UNITS AND THE USE THEREOF IN EXPRESSION VECTORS

The present invention relates to novel transcription units that may be used in expression vectors.

At present, the expression of recombinant proteins is still one of the main methods for producing therapeutic proteins, such as pharmacological antibodies.

The genes coding for the recombinant proteins are generally introduced into a circular expression vector.

One of the purposes of the invention is to provide a transcription unit allowing antibodies to be produced the gain in productivity of which is not linked to a particular antigenic target antibody and therefore by extrapolation to a given recombinant protein, nor linked to the culture medium.

One of the purposes of the invention is to provide a universal transcription unit able to supply better capacity for transcription and expression of a protein of interest relative to the conventional expression vectors.

Another purpose of the invention is to provide a transcription unit allowing the size of expression vector to be limited, in order to limit the problems of cloning or of transfection efficacy in the expression lines.

Finally, another purpose is to provide a transcription unit lacking viral promoters, in order to limit the potential health risks.

The present invention relates to transcription units for constructing the expression vectors.

According to a general aspect, the invention relates to a transcription unit consisting of a polynucleotide comprising the following regulatory elements:

(i)—the hCMVie virus enhancer (E2), said enhancer having the nucleotide sequence SEQ ID NO: 1, or
 a nucleic acid having at least 70% sequence identity with the sequence SEQ ID NO: 1 and essentially possessing properties of transcription activation, and (ii)—the promoter region of cyclin-dependent kinase 9 (CDK9), said promoter region having the nucleotide sequence SEQ ID NO: 2, or
 a nucleic acid having at least 70% sequence identity with the sequence SEQ ID NO: 2 and essentially possessing promoter activity, or
 the promoter region of β-actin, said promoter region having the nucleotide sequence SEQ ID NO: 3, or
 a nucleic acid having at least 70% sequence identity with the sequence SEQ ID NO: 3 and essentially possessing promoter activity.

By "regulatory elements" is meant, in the sense of the present invention, non-coding genomic elements allowing the transcription or translation of a coding nucleic acid to be controlled.

By "transcription unit" is meant a polynucleotide on which an RNA polymerase may be fixed, which makes it possible to synthesize an mRNA starting from a gene of interest bound to said transcription unit.

By "promoter region" is meant a region of DNA that generally contains a particular DNA sequence allowing the transcription of a particular gene of interest to be initiated.

In the sense of the present invention, the terms "promoter region" and "promoter" are interchangeable.

The promoter region is the zone of DNA on which the RNA polymerase is fixed initially, before triggering synthesis of the RNA.

A promoter is generally near the gene of interest to be controlled (from about twenty to about a hundred nucleotides distant) and is located upstream of the site of initiation of transcription of a gene. The presence of a promoter is essential for the transcription of a particular gene.

The promoter of the CDK9 gene represented by the sequence SEQ ID NO: 2 is a GC rich promoter lacking a TATA box.

"A nucleic acid having at least 70% sequence identity with the sequence SEQ ID NO: 2 and essentially possessing promoter activity" contained in a transcription unit according to the present invention is a nucleic acid essentially possessing the same capacity for initiating gene transcription as that of the promoter region of the CDK9 gene, represented by the sequence SEQ ID NO: 2.

The capacity of the promoter region of the CDK9 gene for initiating transcription of a gene can be determined by the method described by Liu et al. (*Gene* 252, 51-59 (2000)).

"A nucleic acid having at least 70% sequence identity with the sequence SEQ ID NO: 3 and essentially possessing promoter activity" contained in a transcription unit according to the present invention is a nucleic acid essentially possessing the same capacity for initiating gene transcription as that of the promoter region of the gene of β-actin, represented by the sequence SEQ ID NO: 3.

The capacity of the promoter region of the gene of β-actin for initiating transcription of a gene can be determined by the method described by Liu et al. (*Gene* 252, 51-59 (2000)).

By "enhancer" is meant a short DNA segment that can fix proteins for stimulating the transcription of a gene. An enhancer is not necessarily close to the gene of interest to be controlled, and can be located at 5' or at 3', or even in the middle of the gene to be controlled or in an intron.

The presence of an enhancer in an expression vector makes it possible to increase the transcription level of a gene.

"A nucleic acid having at least 70% sequence identity with the sequence SEQ ID: NO 1 and essentially possessing properties of transcription activation" is a nucleic acid essentially possessing the same capacity for stimulating gene transcription as that of the hCMVie virus enhancer represented by the sequence SEQ ID NO: 1, hereinafter also designated E2.

The properties of activation of transcription of a gene can be determined by the method described, by using reporter genes such as luciferase.

Several enhancers may coexist in a transcription unit according to the present invention; this makes it possible to stimulate gene transcription even more.

Consequently, a transcription unit according to the present invention may comprise:
 the hCMVie virus enhancer, said enhancer having the nucleotide sequence SEQ ID NO: 1, or a nucleic acid having at least 70% sequence identity with the sequence SEQ ID NO: 1 and essentially possessing properties of transcription activation, and
 at least one other enhancer selected from an SV40 enhancer and an Eμ enhancer.

The percentage identity between two nucleic acid sequences can be calculated from the following formula:

$$\frac{\text{the number of identical residues} \times 100}{\text{the number of residues of the shortest sequence}}$$

In a particular embodiment of the invention, the enhancer is located upstream of the promoter region. In other words, the enhancer is located at the 5' end of the DNA of the promoter region.

The transcription unit described according to the present invention is constituted by a polynucleotide comprising the following regulatory elements:
(i)—the hCMVie virus enhancer, said enhancer having the nucleotide sequence SEQ ID NO: 1, or
a nucleic acid having at least 70% sequence identity with the sequence SEQ ID NO: 1 and essentially possessing properties of transcription activation, and
(ii)—the promoter region of cyclin-dependent kinase 9 (CDK9), said promoter region having the nucleotide sequence SEQ ID NO: 2, or
a nucleic acid having at least 70% sequence identity with the sequence SEQ ID NO: 2 and essentially possessing promoter activity.

The transcription unit obtained is denoted by CMV-CDK9.

The transcription unit described according to the present invention is constituted by a polynucleotide comprising the following regulatory elements:
(i)—the hCMVie virus enhancer, said enhancer having the nucleotide sequence SEQ ID NO: 1, or
a nucleic acid having at least 70% sequence identity with the sequence SEQ ID NO: 1 and essentially possessing properties of transcription activation, and
(ii)—the promoter region of cyclin-dependent kinase 9 (CDK9), said promoter region having the nucleotide sequence SEQ ID NO: 2, or
a nucleic acid having at least 70% sequence identity with the sequence SEQ ID NO: 2 and essentially possessing promoter activity,
the enhancer being located upstream of the promoter region.

In another particular embodiment, a transcription unit according to the present invention is constituted by a polynucleotide comprising the following regulatory elements:
(i)—the hCMVie virus enhancer, said enhancer having the nucleotide sequence SEQ ID NO: 1, or
a nucleic acid having at least 70% sequence identity with the sequence SEQ ID NO: 1 and essentially possessing properties of transcription activation, and
(ii)—the promoter region of β-actin, said promoter region having the nucleotide sequence SEQ ID NO: 3, or
a nucleic acid having at least 70% sequence identity with the sequence SEQ ID NO: 3 and essentially possessing promoter activity.

The transcription unit obtained is denoted by CMV-βactin.

In a more particular embodiment, a transcription unit according to the present invention is constituted by a polynucleotide comprising the following regulatory elements:
(i)—the hCMVie virus enhancer, said enhancer having the nucleotide sequence SEQ ID NO: 1, or
a nucleic acid having at least 70% sequence identity with the sequence SEQ ID NO: 1 and essentially possessing properties of transcription activation, and
(ii)—the promoter region of β-actin, said promoter region having the nucleotide sequence SEQ ID NO: 3, or
a nucleic acid having at least 70% sequence identity with the sequence SEQ ID NO: 3 and essentially possessing promoter activity,
the enhancer being located upstream of the promoter region.

A transcription unit according to the present invention may also comprise a nucleic acid located downstream of the promoter region and upstream of the translation initiation site, said nucleic acid comprising at least one of the untranslated 5' regions (5' UTR) selected from the following:
(i)—the regulatory region R of the Long Terminal Repeat (LTR) (RU-5') of the HTLV-1 virus having the nucleotide sequence SEQ ID NO: 4 (U1), or
a nucleic acid having at least 70% sequence identity with the sequence SEQ ID NO: 4,
(ii)—the 5' UTR region of the NF-κB Repressing Factor (NRF) gene having the nucleotide sequence SEQ ID NO: 5 (U2), or
a nucleic acid having at least 70% sequence identity with the sequence SEQ ID NO: 5,
(iii)—the 5' UTR region of the eukaryotic Initiation Factor 4GI (eIF4GI) gene having the nucleotide sequence SEQ ID NO: 6 (U3), or
a nucleic acid having at least 70% sequence identity with the sequence SEQ ID NO: 6,
the aforesaid nucleic acids having at least 70% sequence identity with one of the sequences represented by the sequences SEQ ID NO: 4, SEQ ID NO: 5 or SEQ ID NO: 6 and essentially having properties of stabilization of the mRNAs and of translation facilitator.

The properties of stabilization of the mRNAs and of translation facilitator can be measured according to Fritz et al. (Sci. STKE, 5 Dec. 2000, Vol. 2000, Issue 61, p. 11).

The untranslated 5' region in a gene corresponds to the portion of the messenger RNA (mRNA) positioned upstream of the translation initiation site. This region allows ribosome fixation and may be involved in regulation of expression of the gene in question.

The translation initiation site is a nucleotide triplet that directs initiation of protein translation. This triplet is often the triplet ATG.

"The nucleic acids having at least 70% sequence identity with one of the sequences represented by the sequences SEQ ID NO: 4, SEQ ID NO: 5 or SEQ ID NO: 6" contained in the transcription units according to the present invention allow ribosome fixation and stabilization of the mRNAs.

The aforesaid nucleic acid located downstream of the promoter region and upstream of the translation initiation site may comprise a single 5' UTR region selected from:
(i)—the R region of the Long Terminal Repeat (LTR) of the HTLV-1 virus having the nucleotide sequence SEQ ID NO: 4 (U1), or
a nucleic acid having at least 70% sequence identity with the sequence SEQ ID NO: 4,
(ii)—the 5' UTR region of the NF-κB Repressing Factor (NRF) gene having the nucleotide sequence SEQ ID NO: 5 (U2), or
a nucleic acid having at least 70% sequence identity with the sequence SEQ ID NO: 5,
(iii)—the 5' UTR region of the eukaryotic Initiation Factor 4GI (eIF4GI) gene having the nucleotide sequence SEQ ID NO: 6 (U3), or
a nucleic acid having at least 70% sequence identity with the sequence SEQ ID NO: 6.

BY a 5' UTR region "located downstream of the promoter region and upstream of the translation initiation site" is meant a 5' UTR region located after the 3' end of the DNA of the promoter region and before the 5' end of the DNA of the translation initiation site.

The aforesaid nucleic acid located downstream of the promoter region and upstream of the translation initiation site may comprise two 5' UTR regions.

The presence of two 5' UTR regions in a transcription unit according to the invention makes it possible to accumulate or synergize the positive effects on the stability of the mRNAs and the efficacy of translation.

An aforesaid nucleic acid used in a transcription unit according to the present invention may comprise the R region of the Long Terminal Repeat (LTR) of the HTLV-1 virus and the 5' UTR region of the NF-κB Repressing Factor (NRF) gene, said nucleic acid being represented by the sequence SEQ ID NO: 7, or being a nucleic acid having at least 70% sequence identity with the sequence SEQ ID NO: 7. The nucleic acid obtained is denoted by U1U2.

An aforesaid nucleic acid used in a transcription unit according to the present invention may also comprise the R region of the Long Terminal Repeat (LTR) of the HTLV-1 virus and the 5' UTR region of the eukaryotic Initiation Factor 4GI (eIF4GI) gene, said nucleic acid being represented by the sequence SEQ ID NO: 8, or being a nucleic acid having at least 70% sequence identity with the sequence SEQ ID NO: 8. The nucleic acid obtained is denoted by U1U3.

An aforesaid nucleic acid used in a transcription unit according to the present invention may also comprise the 5' UTR region of the NF-κB Repressing Factor (NRF) gene and the 5' UTR region of the eukaryotic Initiation Factor 4GI (eIF4GI) gene, said nucleic acid being represented by the sequence SEQ ID NO: 9 or being a nucleic acid having at least 70% sequence identity with the sequence SEQ ID NO: 9. The nucleic acid obtained is denoted by U2U3.

The aforesaid nucleic acid located downstream of the promoter region and upstream of the translation initiation site may also comprise three 5' UTR regions, namely the R region of the Long Terminal Repeat (LTR) of the HTLV-1 virus, the 5' UTR region of the NF-κB Repressing Factor (NRF) gene and the 5' UTR region of the eukaryotic Initiation Factor 4GI (eIF4GI) gene, said nucleic acid being represented by the sequence SEQ ID NO: 10 or being a nucleic acid having at least 70% sequence identity with the sequence SEQ ID NO: 10. The nucleic acid obtained is denoted by U1U2U3.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the R region of the Long Terminal Repeat (LTR) of the HTLV-1 virus represented by the nucleotide sequence SEQ ID NO: 4, or a nucleic acid having at least 70% sequence identity with the sequence SEQ ID NO: 4,
said 5' UTR region being located downstream of the promoter region and upstream of the translation initiation site.

The invention describes in particular a transcription unit consisting of a polynucleotide comprising a nucleic acid represented by the sequence SEQ ID NO: 14 and consisting of:
(i) the hCMVie virus enhancer represented by the sequence SEQ ID NO: 1,
(ii) the promoter region of the CDK9 gene represented by the sequence SEQ ID NO: 2, and
(iii) the 5' UTR region of the LTR of the HTLV-1 virus, represented by the sequence SEQ ID NO: 4,
or of a nucleic acid having at least 70% sequence identity with the sequence SEQ ID NO: 14.

The transcription unit obtained is denoted by CMV-CDK9-U1, otherwise called E2-CDK9-U1.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the 5' UTR region of the NF-κB Repressing Factor (NRF) gene represented by the nucleotide sequence SEQ ID NO: 5, or a nucleic acid having at least 70% sequence identity with the sequence SEQ ID NO: 5,
said 5' UTR region being located downstream of the promoter region and upstream of the translation initiation site.

The invention describes in particular a transcription unit consisting of a polynucleotide comprising a nucleic acid represented by the sequence SEQ ID NO: 15 and consisting of:
(i) the hCMVie virus enhancer represented by the sequence SEQ ID NO: 1,
(ii) the promoter region of the CDK9 gene represented by the sequence SEQ ID NO: 2, and
(iii) the 5' UTR region of the NRF gene, represented by the sequence SEQ ID NO: 5,
or a nucleic acid having at least 70% sequence identity with the sequence SEQ ID NO: 15. The transcription unit obtained is denoted by CMV-CDK9-U2, otherwise called E2-CDK9-U2.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the 5' UTR region of the eukaryotic Initiation Factor 4GI (eIF4GI) gene represented by the nucleotide sequence SEQ ID NO: 6, or a nucleic acid having at least 70% sequence identity with the sequence SEQ ID NO: 6,
said 5' UTR region being located downstream of the promoter region and upstream of the translation initiation site.

The invention describes in particular a transcription unit consisting of a polynucleotide comprising a nucleic acid represented by the sequence SEQ ID NO: 16 and consisting of:
(i) the hCMVie virus enhancer represented by the sequence SEQ ID NO: 1,
(ii) the promoter region of the CDK9 gene represented by the sequence SEQ ID NO: 2, and
(iii) the 5' UTR region of the eIF4GI gene represented by the sequence SEQ ID NO: 6,
or of a nucleic acid having at least 70% sequence identity with the sequence SEQ ID NO: 16.

The transcription unit obtained is denoted by CMV-CDK9-U3, otherwise called E2-CDK9-U3.

The invention describes in particular a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus represented by the nucleotide sequence SEQ ID NO: 4, or a nucleic acid having at least 70% sequence identity with the sequence SEQ ID NO: 4, and (iv) the 5' UTR region of the NF-κB Repressing Factor (NRF) gene represented by the nucleotide sequence SEQ ID NO: 5, or a nucleic acid having at least 70% sequence identity with the sequence SEQ ID NO: 5, the 5' UTR regions being located downstream of the promoter region and upstream of the translation initiation site.

The invention describes in particular a transcription unit consisting of a polynucleotide comprising a nucleic acid represented by the sequence SEQ ID NO: 17 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 7, or of a nucleic acid having at least 70% sequence identity with the sequence SEQ ID NO: 17.

The transcription unit obtained is denoted by CMV-CDK9-U1U2, otherwise called E2-CDK9-U1U2.

The invention describes in particular a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

The invention describes in particular a transcription unit consisting of a polynucleotide comprising a nucleic acid represented by the sequence SEQ ID NO: 18 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 8, or of a nucleic acid having at least 70% sequence identity with the sequence SEQ ID NO: 18.

The transcription unit obtained is denoted by CMV-CDK9-U1U3, otherwise called E2-CDK9-U1U3.

The invention describes in particular a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

The invention describes in particular a transcription unit consisting of a polynucleotide comprising a nucleic acid represented by the sequence SEQ ID NO: 19 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 9, or of a nucleic acid having at least 70% sequence identity with the sequence SEQ ID NO: 19.

The transcription unit obtained is denoted by CMV-CDK9-U2U3, otherwise called E2-CDK9-U2U3.

The invention describes in particular a transcription unit comprising three 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, (iv) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (v) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

The invention describes in particular a transcription unit consisting of a polynucleotide comprising a nucleic acid represented by the sequence SEQ ID NO: 20 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 10, or of a nucleic acid having at least 70% sequence identity with the sequence SEQ ID NO: 20.

The transcription unit obtained is denoted by CMV-CDK9-U1U2U3, otherwise called E2-CDK9-U1U2U3.

In a particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, and (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, said 5' UTR region being located downstream of the promoter region and upstream of the translation initiation site.

In a particular embodiment of the invention, a transcription unit according to the present invention is constituted by a polynucleotide comprising a nucleic acid represented by the sequence SEQ ID NO: 21 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the R region of the LTR of the HTLV-1 virus represented by the nucleotide sequence SEQ ID NO: 4, or of a nucleic acid having at least 70% sequence identity with the sequence SEQ ID NO: 21.

The transcription unit obtained is denoted by CMV-βactin-U1, otherwise called E2-bActin-U1.

In another embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, and (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, said 5' UTR region being located downstream of the promoter region and upstream of the translation initiation site.

In a particular embodiment of the invention, a transcription unit according to the present invention is constituted by a polynucleotide comprising a nucleic acid represented by the sequence SEQ ID NO: 22 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the 5' UTR region of the NRF gene having the nucleotide sequence SEQ ID NO: 5, or of a nucleic acid having at least 70% sequence identity with the sequence SEQ ID NO: 22.

The transcription unit obtained is denoted by CMV-βactin-U2, otherwise called E2-bActin-U2.

In another embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, and (iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, said 5' UTR region being located downstream of the promoter region and upstream of the translation initiation site.

In a particular embodiment of the invention, a transcription unit according to the present invention is constituted by a polynucleotide comprising a nucleic acid represented by the sequence SEQ ID NO: 23 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the 5' UTR region of the eIF4GI gene having the nucleotide sequence SEQ ID NO: 6, or of a nucleic acid having at least 70% sequence identity with the sequence SEQ ID NO: 23.

The transcription unit obtained is denoted by CMV-βactin-U3, otherwise called E2-bActin-U3.

In another particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the 5' UTR region of the NF-κB Repressing Factor (NRF) gene having the nucleotide sequence SEQ ID NO: 5, or a nucleic acid having at least 70% sequence identity with the sequence SEQ ID NO: 5, the 5' UTR regions being located downstream of the promoter region and upstream of the translation initiation site.

In a particular embodiment of the invention, a transcription unit according to the present invention is constituted by a polynucleotide comprising a nucleic acid represented by the sequence SEQ ID NO: 24 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the 5' UTR region represented by the sequence SEQ ID NO: 7, or of a nucleic acid having at least 70% sequence identity with the sequence SEQ ID NO: 24.

The transcription unit obtained is denoted by CMV-βactin-U1U2, otherwise called E2-bActin-U1U2.

In another particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a particular embodiment of the invention, a transcription unit according to the present invention is constituted by a polynucleotide comprising a nucleic acid represented by the sequence SEQ ID NO: 25 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the 5' UTR region represented by the sequence SEQ ID NO: 8, or of a nucleic acid having at least 70% sequence identity with the sequence SEQ ID NO: 25.

The transcription unit obtained is denoted by CMV-βactin-U1U3, otherwise called E2-bActin-U1U3.

In another particular embodiment of the invention, a transcription unit according to the present invention is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a particular embodiment of the invention, a transcription unit according to the present invention is constituted by a polynucleotide comprising a nucleic acid represented by the sequence SEQ ID NO: 26 and consisting of:

(i) the hCMVie virus enhancer represented by the nucleotide sequence SEQ ID NO: 1, (ii) the promoter region of β-actin represented by the nucleotide sequence SEQ ID NO: 3, and (iii) the 5' UTR region represented by the sequence SEQ ID NO: 9, or of a nucleic acid having at least 70% sequence identity with the sequence SEQ ID NO: 26.

The transcription unit obtained is denoted by CMV-βactin-U2U3, otherwise called E2-bActin-U2U3.

In another particular embodiment of the invention, a transcription unit according to the present invention may comprise three 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, (iv) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (v) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a more particular embodiment, a transcription unit according to the invention is constituted by a polynucleotide comprising a nucleic acid represented by the sequence SEQ ID NO: 27 and consisting of:

(i) the hCMVie virus enhancer represented by the sequence SEQ ID NO: 1, (ii) the promoter region of β-actin represented by the sequence SEQ ID NO: 3, and (iii) the 5' UTR region represented by the sequence SEQ ID NO: 10, or of a nucleic acid having at least 70% sequence identity with the sequence SEQ ID NO: 27.

The transcription unit obtained is denoted by CMV-βactin-U1U2U3, otherwise called E2-bActin-U1U2U3.

A transcription unit according to the present invention may also comprise an intron located downstream of said promoter region.

By "intron" is meant a non-coding portion of a gene. An intron is often located between two exons. After transcription, this portion is excised from the RNA to give the messenger RNA. The presence of a heterologous intron makes it possible to optimize expression of the exogenous genes in a DNA construct.

In the construction of a transcription unit according to the present invention, an intron may be located:

(i) downstream of the 5' UTR region and upstream of the translation initiation site, or (ii) downstream of the promoter and upstream of the 5' UTR region, or (iii) after the translation initiation site and within a coding sequence, or (iv) between the stop codon of the coding sequence and the polyadenylation signal.

By "an intron located downstream of said promoter region" is meant an intron located after 3' of the DNA of the promoter region.

Said intron may be selected from the following:

the intron of the Elongation Factor 1α (EF1α) gene having the nucleotide sequence SEQ ID NO: 11, or a nucleic acid having at least 70% sequence identity with the sequence SEQ ID NO: 11, the murine ROSA intron having the nucleotide sequence SEQ ID NO: 12, or a nucleic acid having at least 70% sequence identity with the sequence SEQ ID NO: 12, the human ROSA intron having the nucleotide sequence SEQ ID NO: 13, or a nucleic acid having at least 70% sequence identity with the sequence SEQ ID NO: 13.

A transcription unit according to the present invention may comprise:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) a promoter region selected from:

cyclin-dependent kinase 9 (CDK9), said promoter region having the nucleotide sequence SEQ ID NO: 2, or a nucleic acid having at least 70% sequence identity with the sequence SEQ ID NO: 2 and essentially possessing promoter activity, or β-actin, said promoter region having the nucleotide sequence SEQ ID NO: 3, or a nucleic acid having at least 70% sequence identity with the sequence SEQ ID NO: 3 and essentially possessing promoter activity, and (iii) an intron selected from:

the intron of the Elongation Factor 1α (EF1α) gene having the nucleotide sequence SEQ ID NO: 11, or a nucleic acid having at least 70% sequence identity with the sequence SEQ ID NO: 11, the murine ROSA intron having the nucleotide sequence SEQ ID NO: 12, or a nucleic acid having at least 70% sequence identity with the sequence SEQ ID NO: 12, the human ROSA intron having the nucleotide sequence SEQ ID NO: 13, or a nucleic acid having at least 70% sequence identity with the sequence SEQ ID NO: 13.

said enhancer being located at 5' or at 3' of the transcription unit, or within the coding sequence or in an intron;

said intron being located:

(i) downstream of the 5' UTR region and upstream of the translation initiation site, or (ii) downstream of the promoter and upstream of the 5' UTR region, or (iii) after the translation initiation site and within the coding sequence, or (iv) between the stop codon of the coding sequence and the polyadenylation signal.

The invention also describes a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and (iii) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 28 and consisting of:

(i) the hCMVie virus enhancer represented by the nucleotide sequence SEQ ID NO: 1, (ii) the promoter region of the CDK9 gene represented by the nucleotide sequence SEQ ID NO: 2, and (iii) the intron of the EF1α gene represented by the nucleotide sequence SEQ ID NO: 11, or of a nucleic acid having at least 70% sequence identity with the sequence SEQ ID NO: 28.

The transcription unit obtained is denoted by CMV-CDK9-EF1α, otherwise called E2-CDK9-EF1α.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and (iii) the murine ROSA intron having the nucleotide sequence SEQ ID NO: 12, or a nucleic acid having at least 70% sequence identity with the sequence SEQ ID NO: 12.

The invention describes in particular a transcription unit according to the invention consisting of a polynucleotide comprising a nucleic acid represented by the sequence SEQ ID NO: 29 and consisting of:
  (i) the hCMVie virus enhancer represented by the nucleotide sequence SEQ ID NO: 1,
  (ii) the promoter region of the CDK9 gene represented by the nucleotide sequence SEQ ID NO: 2, and
  (iii) the murine ROSA intron having the nucleotide sequence SEQ ID NO: 12,
or of a nucleic acid having at least 70% sequence identity with the sequence SEQ ID NO: 29.

The transcription unit obtained is denoted by CMV-CDK9-mROSA, otherwise called E2-CDK9-mROSA.

The invention describes in particular a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
  (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
  (iii) the human ROSA intron having the nucleotide sequence SEQ ID NO: 13,
or a nucleic acid having at least 70% sequence identity with the sequence SEQ ID NO: 13.

The invention describes in particular a transcription unit according to the invention consisting of a polynucleotide comprising a nucleic acid represented by the sequence SEQ ID NO: 30 and consisting of:
  (i) the hCMVie virus enhancer represented by the nucleotide sequence SEQ ID NO: 1,
  (ii) the promoter region of the CDK9 gene represented by the nucleotide sequence SEQ ID NO: 2, and
  (iii) the human ROSA intron having the nucleotide sequence SEQ ID NO: 12,
or of a nucleic acid having at least 70% sequence identity with the sequence SEQ ID NO: 30.

The transcription unit obtained is denoted by CMV-CDK9-hROSA, otherwise called E2-CDK9-hROSA.

A particular embodiment of the invention relates to a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
  (ii) the promoter region of β-actin represented by the nucleotide sequence SEQ ID NO: 3, or a nucleic acid having at least 70% sequence identity with the sequence SEQ ID NO: 3 and essentially possessing promoter activity, and
  (iii) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 31 and consisting of:
  (i) the hCMVie virus enhancer represented by the nucleotide sequence SEQ ID NO: 1,
  (ii) the promoter region of β-actin represented by the nucleotide sequence SEQ ID NO: 3, and
  (iii) the intron of the EF1α gene represented by the nucleotide sequence SEQ ID NO: 11,
or of a nucleic acid having at least 70% sequence identity with the sequence SEQ ID NO: 31.

The transcription unit obtained is denoted by CMV-βactin-EF1α, otherwise called E2-bActin-EF.

A particular embodiment of the invention relates to a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
  (ii) the promoter region of β-actin represented by the nucleotide sequence SEQ ID NO: 3, or a nucleic acid having at least 70% sequence identity with the sequence SEQ ID NO: 3 and essentially possessing promoter activity, and
  (iii) the murine ROSA intron having the nucleotide sequence SEQ ID NO: 12,
or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 32 and consisting of:
  (i) the hCMVie virus enhancer represented by the nucleotide sequence SEQ ID NO: 1,
  (ii) the promoter region of β-actin represented by the nucleotide sequence SEQ ID NO: 3, and
  (iii) the murine ROSA intron having the nucleotide sequence SEQ ID NO: 12,
or of a nucleic acid having at least 70% sequence identity with the sequence SEQ ID NO: 32.

The transcription unit obtained is denoted by CMV-βactin-mROSA, otherwise called E2-bActin-mROSA.

A particular embodiment of the invention relates to a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
  (ii) the promoter region of β-actin represented by the nucleotide sequence SEQ ID NO: 3, or a nucleic acid having at least 70% sequence identity with the sequence SEQ ID NO: 3 and essentially possessing promoter activity, and
  (iii) the human ROSA intron having the nucleotide sequence SEQ ID NO: 13,
or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 33 and consisting of:
  (i) the hCMVie virus enhancer represented by the nucleotide sequence SEQ ID NO: 1,
  (ii) the promoter region of β-actin represented by the nucleotide sequence SEQ ID NO: 3, and
  (iii) the human ROSA intron having the nucleotide sequence SEQ ID NO: 13,
or of a nucleic acid having at least 70% sequence identity with the sequence SEQ ID NO: 33.

The transcription unit obtained is denoted by CMV-βactin-hROSA, otherwise called E2-bActin-hROSA.

A transcription unit according to the present invention may comprise:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) a promoter region selected from:

cyclin-dependent kinase 9 (CDK9), said promoter region having the nucleotide sequence SEQ ID NO: 2, or a nucleic acid having at least 70% sequence identity with the sequence SEQ ID NO: 2 and essentially possessing promoter activity, or β-actin, said promoter region having the nucleotide sequence SEQ ID NO: 3, or a nucleic acid having at least 70% sequence identity with the sequence SEQ ID NO: 3 and essentially possessing promoter activity, (iii) at least one of the untranslated 5' regions (5' UTR) selected from:

the R region of the Long Terminal Repeat (LTR) of the HTLV-1 virus having the nucleotide sequence SEQ ID NO: 4, or a nucleic acid having at least 70% sequence identity with the sequence SEQ ID NO: 4, the 5' UTR region of the NF-κB Repressing Factor (NRF) gene having the nucleotide sequence SEQ ID NO: 5, or a nucleic acid having at least 70% sequence identity with the sequence SEQ ID NO: 5, the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and (iv) an intron selected from:

the intron of the Elongation Factor 1α (EF1α) gene having the nucleotide sequence SEQ ID NO: 11, or a nucleic acid having at least 70% sequence identity with the sequence SEQ ID NO: 11, the murine ROSA intron having the nucleotide sequence SEQ ID NO: 12, or a nucleic acid having at least 70% sequence identity with the sequence SEQ ID NO: 12, the human ROSA intron having the nucleotide sequence SEQ ID NO: 13, or a nucleic acid having at least 70% sequence identity with the sequence SEQ ID NO: 13.

said enhancer being located at 5' or at 3' of the transcription unit, or within the coding sequence or in an intron;

said promoter region being located upstream of the 5' UTR region;

said intron being located:

(i) downstream of the 5' UTR region and upstream of the translation initiation site, or (ii) downstream of the promoter and upstream of the 5' UTR region, or (iii) after the translation initiation site and within the coding sequence, or (iv) between the stop codon of the coding sequence and the polyadenylation signal.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 34 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the R region of the LTR of the HTLV-1 virus having the nucleotide sequence SEQ ID NO: 4, and (iv) the intron of the Elongation Factor 1α (EF1α) gene having the nucleotide sequence SEQ ID NO: 11, or of a nucleic acid having at least 70% sequence identity with the sequence SEQ ID NO: 34.

The transcription unit obtained is denoted by CMV-CDK9-U1-EF1α, otherwise called E2-CDK9-U1-EF.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the murine ROSA intron having the nucleotide sequence SEQ ID NO: 12, or a nucleic acid having at least 70% sequence identity with the sequence SEQ ID NO: 12.

The invention describes in particular a transcription unit consisting of a polynucleotide comprising a nucleic acid represented by the sequence SEQ ID NO: 35 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the R region of the LTR of the HTLV-1 virus having the nucleotide sequence SEQ ID NO: 4, and (iv) the murine ROSA intron having the nucleotide sequence SEQ ID NO: 12, or of a nucleic acid having at least 70% sequence identity with the sequence SEQ ID NO: 35.

The transcription unit obtained is denoted by CMV-CDK9-U1-mROSA, otherwise called E2-CDK9-U1-mROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 36 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the R region of the LTR of the HTLV-1 virus having the nucleotide sequence SEQ ID NO: 4, and (iv) the human ROSA intron having the nucleotide sequence SEQ ID NO: 13, or of a nucleic acid having at least 70% sequence identity with the sequence SEQ ID NO: 36.

The transcription unit obtained is denoted by CMV-CDK9-U1-hROSA, otherwise called E2-CDK9-U1-hROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 37 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region of the NRF gene having the nucleotide sequence SEQ ID NO: 5, and (iv) the intron of the Elongation Factor 1α (EF1α) gene having the nucleotide sequence SEQ ID NO: 11, or of a nucleic acid having at least 70% sequence identity with the sequence SEQ ID NO: 37.

The transcription unit obtained is denoted by CMV-CDK9-U2-EF1α, otherwise called E2-CDK9-U2-EF.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the murine ROSA intron having the nucleotide sequence SEQ ID NO: 12, or a nucleic acid having at least 70% sequence identity with the sequence SEQ ID NO: 12.

The invention describes in particular a transcription unit consisting of a polynucleotide comprising a nucleic acid represented by the sequence SEQ ID NO: 38 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region of the NRF gene having the nucleotide sequence SEQ ID NO: 5, and (iv) the murine ROSA intron having the nucleotide sequence SEQ ID NO: 12, or of a nucleic acid having at least 70% sequence identity with the sequence SEQ ID NO: 38.

The transcription unit obtained is denoted by CMV-CDK9-U2-mROSA, otherwise called E2-CDK9-U2-mROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 39 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the NRF gene having the nucleotide sequence SEQ ID NO: 5, and
(iv) the human ROSA intron having the nucleotide sequence SEQ ID NO: 13,
or of a nucleic acid having at least 70% sequence identity with the sequence SEQ ID NO: 39.

The transcription unit obtained is denoted by CMV-CDK9-U2-hROSA, otherwise called E2-CDK9-U2-hROSA.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 40 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the intron of the Elongation Factor 1α (EF1α) gene having the nucleotide sequence SEQ ID NO: 11,
or of a nucleic acid having at least 70% sequence identity with the sequence SEQ ID NO: 40, and essentially possessing properties of transcription activation superior to those of the CMV enhancer associated with the promoter region of CDK9.

The transcription unit obtained is denoted by CMV-CDK9-U3-EF1α, otherwise called E2-CDK9-U3-EF.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the murine ROSA intron having the nucleotide sequence SEQ ID NO: 12,
or a nucleic acid having at least 70% sequence identity with the sequence SEQ ID NO: 12.

The invention describes in particular a transcription unit consisting of a polynucleotide comprising a nucleic acid represented by the sequence SEQ ID NO: 41 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the murine ROSA intron having the nucleotide sequence SEQ ID NO: 12,
or of a nucleic acid having at least 70% sequence identity with the sequence SEQ ID NO: 41.

The transcription unit obtained is denoted by CMV-CDK9-U3-mROSA, otherwise called E2-CDK9-U3-mROSA.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 42 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the human ROSA intron having the nucleotide sequence SEQ ID NO: 13, or of a nucleic acid having at least 70% sequence identity with the sequence SEQ ID NO: 42.

The transcription unit obtained is denoted by CMV-CDK9-U3-hROSA, otherwise called E2-CDK9-U3-hROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, (iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 43 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the intron of the Elongation Factor 1α (EF1α) gene having the nucleotide sequence SEQ ID NO: 11, or of a nucleic acid having at least 70% sequence identity with the sequence SEQ ID NO: 43.

The transcription unit obtained is denoted by CMV-CDK9-U1U2-EF1α, otherwise called E2-CDK9-U1U2-EF.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, and (iv) the murine ROSA intron having the nucleotide sequence SEQ ID NO: 12, or a nucleic acid having at least 70% sequence identity with the sequence SEQ ID NO: 12.

The invention describes in particular a transcription unit consisting of a polynucleotide comprising a nucleic acid represented by the sequence SEQ ID NO: 44 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the murine ROSA intron having the nucleotide sequence SEQ ID NO: 12, or of a nucleic acid having at least 70% sequence identity with the sequence SEQ ID NO: 44.

The transcription unit obtained is denoted by CMV-CDK9-U1U2-mROSA, otherwise called E2-CDK9-U1U2-mROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, and (iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 45 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the human ROSA intron having the nucleotide sequence SEQ ID NO: 13, or of a nucleic acid having at least 70% sequence identity with the sequence SEQ ID NO: 45.

The transcription unit obtained is denoted by CMV-CDK9-U1U2-hROSA, otherwise called E2-CDK9-U1U2-hROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 8, or a nucleic acid having at least 70% sequence identity with the sequence SEQ ID NO: 8, and (iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 46 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 8, and
(iv) the intron of the Elongation Factor 1α (EF1α) gene having the nucleotide sequence SEQ ID NO: 11,
or of a nucleic acid having at least 70% sequence identity with the sequence SEQ ID NO: 46.

The transcription unit obtained is denoted by CMV-CDK9-U1U3-EF1α, otherwise called E2-CDK9-U1U3-EF.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region represented by the sequence SEQ ID NO: 8, or a nucleic acid having at least 70% sequence identity with the sequence SEQ ID NO: 8, and
(iv) the murine ROSA intron having the nucleotide sequence SEQ ID NO: 12,
or a nucleic acid having at least 70% sequence identity with the sequence SEQ ID NO: 12.

The invention describes in particular a transcription unit consisting of a polynucleotide comprising a nucleic acid represented by the sequence SEQ ID NO: 47 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 8, and
(iv) the murine ROSA intron having the nucleotide sequence SEQ ID NO: 12,
or of a nucleic acid having at least 70% sequence identity with the sequence SEQ ID NO: 47.

The transcription unit obtained is denoted by CMV-CDK9-U1U3-mROSA, otherwise called E2-CDK9-U1U3-mROSA.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region represented by the sequence SEQ ID NO: 9, or a nucleic acid having at least 70% sequence identity with the sequence SEQ ID NO: 9, and
(iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 48 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 8, and
(iv) the human ROSA intron having the nucleotide sequence SEQ ID NO: 13,
or of a nucleic acid having at least 70% sequence identity with the sequence SEQ ID NO: 48.

The transcription unit obtained is denoted by CMV-CDK9-U1U3-hROSA, otherwise called E2-CDK9-U1U3-hROSA.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region represented by the sequence SEQ ID NO: 9, or a nucleic acid having at least 70% sequence identity with the sequence SEQ ID NO: 9, and
(iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 49 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 9, and
(iv) the intron of the Elongation Factor 1α (EF1α) gene having the nucleotide sequence SEQ ID NO: 11,
or of a nucleic acid having at least 70% sequence identity with the sequence SEQ ID NO: 49.

The transcription unit obtained is denoted by CMV-CDK9-U2U3-EF1α, otherwise called E2-CDK9-U2U3-EF.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, (iv) the murine ROSA intron having the nucleotide sequence SEQ ID NO: 12, or a nucleic acid having at least 70% sequence identity with the sequence SEQ ID NO: 12.

The invention describes in particular a transcription unit consisting of a polynucleotide comprising a nucleic acid represented by the sequence SEQ ID NO: 50 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 9, and (iv) the murine ROSA intron having the nucleotide sequence SEQ ID NO: 12, or of a nucleic acid having at least 70% sequence identity with the sequence SEQ ID NO: 50.

The transcription unit obtained is denoted by CMV-CDK9-U2U3-mROSA, otherwise called E2-CDK9-UU2U3-mROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, and (iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 51 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 9, and (iv) the human ROSA intron having the nucleotide sequence SEQ ID NO: 13, or of a nucleic acid having at least 70% sequence identity with the sequence SEQ ID NO: 51.

The transcription unit obtained is denoted by CMV-CDK9-U2U3-hROSA, otherwise called E2-CDK9-U2U3-hROSA.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 10, or a nucleic acid having at least 70% sequence identity with the sequence SEQ ID NO: 10, and (iv) the intron of the Elongation Factor 1α (EF1α) gene having the nucleotide sequence SEQ ID NO: 11, or a nucleic acid having at least 70% sequence identity with the sequence SEQ ID NO: 11.

The invention describes in particular a transcription unit consisting of a polynucleotide comprising a nucleic acid represented by the sequence SEQ ID NO: 52 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 10, and (iv) the intron of the Elongation Factor 1α (EF1α) gene having the nucleotide sequence SEQ ID NO: 11, or of a nucleic acid having at least 70% sequence identity with the sequence SEQ ID NO: 52.

The transcription unit obtained is denoted by CMV-CDK9-U1U2U3-EF1α, otherwise called E2-CDK9-U1U2U3-EF.

The invention describes in particular a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 10, or a nucleic acid having at least 70% sequence identity with the sequence SEQ ID NO: 10, and (iv) the murine ROSA intron having the nucleotide sequence SEQ ID NO: 12, or a nucleic acid having at least 70% sequence identity with the sequence SEQ ID NO: 12.

The invention describes in particular a transcription unit consisting of a polynucleotide comprising a nucleic acid represented by the sequence SEQ ID NO: 53 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 10, and
(iv) the murine ROSA intron having the nucleotide sequence SEQ ID NO: 12,
or of a nucleic acid having at least 70% sequence identity with the sequence SEQ ID NO: 53.

The transcription unit obtained is denoted by CMV-CDK9-U1U2U3-mROSA, otherwise called E2-CDK9-U1U2U3-mROSA.

The invention describes in particular a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region represented by the sequence SEQ ID NO: 10, or a nucleic acid having at least 70% sequence identity with the sequence SEQ ID NO: 10, and
(iv) the human ROSA intron having the nucleotide sequence SEQ ID NO: 13, or a nucleic acid having at least 70% sequence identity with the sequence SEQ ID NO: 13.

The invention describes in particular a transcription unit consisting of a polynucleotide comprising a nucleic acid represented by the sequence SEQ ID NO: 54 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 10, and
(iv) the human ROSA intron having the nucleotide sequence SEQ ID NO: 13,
or of a nucleic acid having at least 70% sequence identity with the sequence SEQ ID NO: 54.

The transcription unit obtained is denoted by CMV-CDK9-U1U2U3-hROSA, otherwise called E2-CDK9-U1U2U3-hROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and
(iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 55 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the R region of the LTR of the HTLV-1 virus having the nucleotide sequence SEQ ID NO: 4,
(iv) the intron of the Elongation Factor 1α (EF1α) gene having the nucleotide sequence SEQ ID NO: 11,
or of a nucleic acid having at least 70% sequence identity with the sequence SEQ ID NO: 55.

The transcription unit obtained is denoted by CMV-βactin-U1-EF1α, otherwise called E2-bActin-U1-EF.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and
(iv) the murine ROSA intron having the nucleotide sequence SEQ ID NO: 12,
or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 56 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the R region of the LTR of the HTLV-1 virus having the nucleotide sequence SEQ ID NO: 4, and
(iv) the murine ROSA intron having the nucleotide sequence SEQ ID NO: 12,
or of a nucleic acid having at least 70% sequence identity with the sequence SEQ ID NO: 56.

The transcription unit obtained is denoted by CMV-βactin-U1-mROSA, otherwise called E2-bActin-U1-mROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 57 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the R region of the LTR of the HTLV-1 virus having the nucleotide sequence SEQ ID NO: 4, and (iv) the human ROSA intron having the nucleotide sequence SEQ ID NO: 13, or of a nucleic acid having at least 70% sequence identity with the sequence SEQ ID NO: 57.

The transcription unit obtained is denoted by CMV-βactin-U1-hROSA, otherwise called E2-bActin-U1-hROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 58 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region of the NRF gene having the nucleotide sequence SEQ ID NO: 5, and (iv) the intron of the Elongation Factor 1α (EF1α) gene having the nucleotide sequence SEQ ID NO: 11, or of a nucleic acid having at least 70% sequence identity with the sequence SEQ ID NO: 58.

The transcription unit obtained is denoted by CMV-βactin-U2-EF1α, otherwise called E2-bActin-U2-EF.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the murine ROSA intron having the nucleotide sequence SEQ ID NO: 12, or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 59 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region of the NRF gene having the nucleotide sequence SEQ ID NO: 5, and (iv) the murine ROSA intron having the nucleotide sequence SEQ ID NO: 12, or of a nucleic acid having at least 70% sequence identity with the sequence SEQ ID NO: 59.

The transcription unit obtained is denoted by CMV-βactin-U2-mROSA, otherwise called E2-bActin-U2-mROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 60 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region of the NRF gene having the nucleotide sequence SEQ ID NO: 5, and (iv) the human ROSA intron having the nucleotide sequence SEQ ID NO: 13,
or of a nucleic acid having at least 70% sequence identity with the sequence SEQ ID NO: 60.

The transcription unit obtained is denoted by CMV-βactin-U2-hROSA, otherwise called E2-bActin-U2-hROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 61 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region of the eIF4GI gene having the nucleotide sequence SEQ ID NO: 6, and
(iv) the intron of the Elongation Factor 1α (EF1α) gene having the nucleotide sequence SEQ ID NO: 11,
or of a nucleic acid having at least 70% sequence identity with the sequence SEQ ID NO: 61.

The transcription unit obtained is denoted by CMV-βactin-U3-EF1α, otherwise called E2-bActin-U3-EF.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the murine ROSA intron having the nucleotide sequence SEQ ID NO: 12,
or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 62 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region of the eIF4GI gene having the nucleotide sequence SEQ ID NO: 6, and
(iv) the murine ROSA intron having the nucleotide sequence SEQ ID NO: 12,
or of a nucleic acid having at least 70% sequence identity with the sequence SEQ ID NO: 62.

The transcription unit obtained is denoted by CMV-βactin-U3-mROSA, otherwise called E2-bActin-U3-mROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 63 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region of the eIF4GI gene having the nucleotide sequence SEQ ID NO: 6, and
(iv) the human ROSA intron having the nucleotide sequence SEQ ID NO: 13,
or of a nucleic acid having at least 70% sequence identity with the sequence SEQ ID NO: 63.

The transcription unit obtained is denoted by CMV-βactin-U3-hROSA, otherwise called E2-bActin-U3-hROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region represented by the sequence SEQ ID NO: 7, or a nucleic acid having at least 70% sequence identity with the sequence SEQ ID NO: 7, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 64 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region represented by the nucleotide sequence SEQ ID NO: 7, and
(iv) the intron of the Elongation Factor 1α (EF1α) gene having the nucleotide sequence SEQ ID NO: 11,
or of a nucleic acid having at least 70% sequence identity with the sequence SEQ ID NO: 64.

The transcription unit obtained is denoted by CMV-βactin-U1U2-EF1α, otherwise called E2-bActin-U1U2-EF.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region represented by the sequence SEQ ID NO: 7, or a nucleic acid having at least 70% sequence identity with the sequence SEQ ID NO: 7, and
(iv) the murine ROSA intron having the nucleotide sequence SEQ ID NO: 12,
or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 65 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region represented by the nucleotide sequence SEQ ID NO: 7, and
(iv) the murine ROSA intron having the nucleotide sequence SEQ ID NO: 12,
or of a nucleic acid having at least 70% sequence identity with the sequence SEQ ID NO: 65.

The transcription unit obtained is denoted by CMV-βactin-U1U2-mROSA, otherwise called E2-bActin-U1U2-mROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region represented by the sequence SEQ ID NO: 7, or a nucleic acid having at least 70% sequence identity with the sequence SEQ ID NO: 7, and
(iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 66 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region represented by the nucleotide sequence SEQ ID NO: 7, and
(iv) the human ROSA intron having the nucleotide sequence SEQ ID NO: 13,
or of a nucleic acid having at least 70% sequence identity with the sequence SEQ ID NO: 66.

The transcription unit obtained is denoted by CMV-βactin-U1U2-hROSA, otherwise called E2-bActin-U1U2-hROSA.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of β-actin represented by the nucleotide sequence SEQ ID NO: 3, or a nucleic acid having at least 70% sequence identity with the sequence SEQ ID NO: 3 and essentially possessing promoter activity,
(iii) the 5' UTR region represented by the sequence SEQ ID NO: 8, or a nucleic acid having at least 70% sequence identity with the sequence SEQ ID NO: 8, and
(iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 67 and consisting of:
(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region represented by the nucleotide sequence SEQ ID NO: 8, and
(iv) the intron of the Elongation Factor 1α (EF1α) gene having the nucleotide sequence SEQ ID NO: 11,
or of a nucleic acid having at least 70% sequence identity with the sequence SEQ ID NO: 67.

The transcription unit obtained is denoted by CMV-βactin-U1U3-EF1α, otherwise called E2-bActin-U1U3-EF.

A particular embodiment of the invention relates to a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 8, or a nucleic acid having at least 70% sequence identity with the sequence SEQ ID NO: 8, and (iv) the murine ROSA intron having the nucleotide sequence SEQ ID NO: 12, or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 68 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 8, and (iv) the murine ROSA intron having the nucleotide sequence SEQ ID NO: 12, or of a nucleic acid having at least 70% sequence identity with the sequence SEQ ID NO: 68.

The transcription unit obtained is denoted by CMV-βactin-U1U3-mROSA, otherwise called E2-bActin-U1U3-mROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 8, or a nucleic acid having at least 70% sequence identity with the sequence SEQ ID NO: 9, and (iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 69 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 8, and (iv) the human ROSA intron having the nucleotide sequence SEQ ID NO: 13, or of a nucleic acid having at least 70% sequence identity with the sequence SEQ ID NO: 69.

The transcription unit obtained is denoted by CMV-βactin-U1U3-hROSA, otherwise called E2-bActin-U1U3-hROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 9, or a nucleic acid having at least 70% sequence identity with the sequence SEQ ID NO: 9, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 70 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 9, and (iv) the intron of the Elongation Factor 1α (EF1α) gene having the nucleotide sequence SEQ ID NO: 11, or of a nucleic acid having at least 70% sequence identity with the sequence SEQ ID NO: 70.

The transcription unit obtained is denoted by CMV-βactin-U2U3-EF1α, otherwise called E2-bActin-U2U3-EF.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 9, or a nucleic acid having at least 70% sequence identity with the sequence SEQ ID NO: 9, and (iv) the murine ROSA intron having the nucleotide sequence SEQ ID NO: 12, or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 71 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 9, and (iv) the murine ROSA intron having the nucleotide sequence SEQ ID NO: 12, or of a nucleic acid having at least 70% sequence identity with the sequence SEQ ID NO: 71.

The transcription unit obtained is denoted by CMV-βactin-U2U3-mROSA, otherwise called E2-bActin-U2U3-mROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 9, or a nucleic acid having at least 70% sequence identity with the sequence SEQ ID NO: 9, and (iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 72 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 9, (iv) the human ROSA intron having the nucleotide sequence SEQ ID NO: 13, and or of a nucleic acid having at least 70% sequence identity with the sequence SEQ ID NO: 72.

The transcription unit obtained is denoted by CMV-βactin-U2U3-hROSA, otherwise called E2-bActin-U2U3-hROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 10, or a nucleic acid having at least 70% sequence identity with the sequence SEQ ID NO: 10, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment of the invention, a transcription unit according to the invention is constituted by a polynucleotide comprising a nucleic acid represented by the sequence SEQ ID NO: 73 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 10, and (iv) the intron of the Elongation Factor 1α (EF1α) gene having the nucleotide sequence SEQ ID NO: 11, or of a nucleic acid having at least 70% sequence identity with the sequence SEQ ID NO: 73.

The transcription unit obtained is denoted by CMV-βactin-U1U2U3-EF1α, otherwise called E2-bActin-U1U2U3-EF.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 10, or a nucleic acid having at least 70% sequence identity with the sequence SEQ ID NO: 10, and (iv) the murine ROSA intron having the nucleotide sequence SEQ ID NO: 12, or a nucleic acid having at least 70% sequence identity with the sequence SEQ ID NO: 12.

In a more particular embodiment of the invention, a transcription unit according to the invention is constituted by a polynucleotide comprising a nucleic acid represented by the sequence SEQ ID NO: 74 and consisting of:

(i) the hCMVie virus enhancer represented by the nucleotide sequence SEQ ID NO: 1, (ii) the promoter region of β-actin represented by the nucleotide sequence SEQ ID NO: 3, (iii) the 5' UTR region represented by the nucleotide sequence SEQ ID NO: 10, and (iv) the murine ROSA intron having the nucleotide sequence SEQ ID NO: 12, or of a nucleic acid having at least 70% sequence identity with the sequence SEQ ID NO: 74.

The transcription unit obtained is denoted by CMV-βactin-U1U2U3-mROSA, otherwise called E2-bActin-U1U2U3-mROSA.

A particular embodiment of the invention relates to a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of β-actin represented by the nucleotide sequence SEQ ID NO: 3, or a nucleic acid having at least 70% sequence identity with the sequence SEQ ID NO: 3 and essentially possessing promoter activity, (iii) the 5' UTR region represented by the sequence SEQ ID NO: 10, or a nucleic acid having at least 70% sequence identity with the sequence SEQ ID NO: 10, and (iv) the human ROSA intron having the nucleotide sequence SEQ ID NO: 13, or a nucleic acid having at least 70% sequence identity with the sequence SEQ ID NO: 13.

In a more particular embodiment of the invention, a transcription unit according to the invention is constituted by a polynucleotide comprising a nucleic acid represented by the sequence SEQ ID NO: 75 and consisting of:

(i) the hCMVie virus enhancer represented by the nucleotide sequence SEQ ID NO: 1,
(ii) the promoter region of β-actin represented by the nucleotide sequence SEQ ID NO: 3,
(iii) the 5' UTR region represented by the nucleotide sequence SEQ ID NO: 10, and
(iv) the human ROSA intron having the nucleotide sequence SEQ ID NO: 13,
or of a nucleic acid having at least 70% sequence identity with the sequence SEQ ID NO: 75.

The transcription unit obtained is denoted by CMV-βactin-U1U2U3-hROSA, otherwise called E2-bActin-U1U2U3-hROSA.

In an advantageous embodiment, the present invention relates to a transcription unit, said transcription unit comprising the hCMVie virus enhancer, the promoter region of β-actin, the 5' UTR region of the HTLV-1 virus (U1), and the 5' UTR region is that of the eIF4GI gene (U3), said transcription unit having the nucleotide sequence SEQ ID NO: 25, or a nucleotide sequence having at least 70% identity with SEQ ID NO: 25 and giving a volume-based production of a protein of interest greater than that obtained with the combination of the CMV enhancer associated with the promoter region of β-actin.

By "volume-based production" is meant a quantity of protein expressed as weight per unit volume (g/L), also called protein titre or concentration of the protein of interest.

The present invention also relates to an expression vector comprising at least one transcription unit as defined above and at least one cloning site allowing integration of a nucleic acid coding for a protein of interest.

Said nucleic acid may be genomic DNA or cDNA.

By "cloning site" is meant a short DNA segment that comprises several restriction sites, recognized respectively by different restriction enzymes.

The present invention also relates to an expression vector comprising at least one transcription unit as defined above and at least one site for site-specific recombination allowing integration of a nucleic acid coding for a protein of interest.

Said nucleic acid may be genomic DNA or cDNA.

By "site for site-specific recombination" is meant a short DNA segment that is recognized by a recombinase, such as the loxP site, which is recognized by the recombinase Cre, the xis site that is recognized by the integrase Int, the FRT site that is recognized by the recombinase FLP.

An expression vector according to the present invention may further comprise a eukaryotic resistance gene, a bacterial resistance gene, a bacterial replication origin and a unit dedicated to gene amplification.

A eukaryotic resistance gene may be a gene with resistance to Geneticine (G418), Blasticidine, zeocine.

A bacterial resistance gene may be a gene with resistance to ampicillin, kanamycin, puromycin, Blasticidine, Zeocine.

A bacterial replication origin (Ori) is a particular DNA sequence of bacterial origin allowing initiation of replication of the genetic material such as an expression vector and of packaging in the bacterium the number of vector copies per bacterium. Such a replication origin may be selected from Ori-P, Ori-C, Ori-f1, ColE1, pSC101 Ori, p15A Ori, pACYC Ori, SV40 Ori, Pmb1 Ori, Puc Ori.

By "a unit dedicated to gene amplification" is meant any unit for performing gene amplification and/or enrichment with strong expressors. Most often, this unit allows the expression of a gene for resistance to an inhibitor with dose-dependent action; by increasing the dose of inhibitor, there is selection of variants more strongly expressing the resistance gene, in particular following gene amplification or integration in a site with strong expression. Most often, the genes near this unit also undergo gene amplification and/or increased expression. Such a unit may be the dhfr (dihydrofolate reductase) gene, whose inhibitor is methotrexate, or the glutamine synthetase gene, whose inhibitor is methionyl sulphoximine, a system for amplification of gene fragments that is based on selection of transformants resistant to methotrexate (MTX). It requires the prior introduction of a transcription unit comprising the nucleic acid coding for the DHFR (dihydrofolate reductase) enzyme in the expression vector for producing the recombinant molecule of interest (SHITARI et al., 1994).

A protein of interest capable of being produced by a vector according to the invention is a protein selected from the group consisting of the proteins participating in coagulation or an immunoglobulin, cytokines, hormones, growth factors or complement factors and any fusion protein.

In a more particular embodiment of the invention, the expression vector according to the invention comprises a transcription unit comprising a nucleic acid represented by the sequence SEQ ID NO: 21 and consisting of:
(i) the hCMVie virus enhancer represented by the nucleotide sequence SEQ ID NO: 1,
(ii) the promoter region of β-actin represented by the nucleotide sequence SEQ ID NO: 3, and
(iii) the R region of the LTR of the HTLV-1 virus represented by the nucleotide sequence SEQ ID NO: 4.

In a more particular embodiment of the invention, the expression vector according to the invention comprises a transcription unit comprising a nucleic acid represented by the sequence SEQ ID NO: 22 and consisting of:
(i) the hCMVie virus enhancer represented by the nucleotide sequence SEQ ID NO: 1,
(ii) the promoter region of β-actin represented by the nucleotide sequence SEQ ID NO: 3, and
(iii) the 5' UTR region of the NF-κB Repressing Factor (NRF) gene having the nucleotide sequence SEQ ID NO: 5.

In a more particular embodiment of the invention, the expression vector according to the invention comprises a transcription unit comprising a nucleic acid represented by the sequence SEQ ID NO: 23 and consisting of:
(i) the hCMVie virus enhancer represented by the nucleotide sequence SEQ ID NO: 1,
(ii) the promoter region of β-actin represented by the nucleotide sequence SEQ ID NO: 3, and
(iii) the 5' UTR region of the eukaryotic Initiation Factor 4GI (eIF4GI) gene having the nucleotide sequence SEQ ID NO: 6.

In a more particular embodiment of the invention, the expression vector according to the invention comprises a transcription unit comprising a nucleic acid represented by the sequence SEQ ID NO: 25 and consisting of:
(i) the hCMVie virus enhancer represented by the nucleotide sequence SEQ ID NO: 1,
(ii) the promoter region of β-actin represented by the nucleotide sequence SEQ ID NO: 3, and
(iii) the 5' UTR region represented by the nucleotide sequence SEQ ID NO: 8.

In a more particular embodiment of the invention, the expression vector according to the invention comprises a transcription unit comprising a nucleic acid represented by the sequence SEQ ID NO: 26 and consisting of:
(i) the hCMVie virus enhancer represented by the nucleotide sequence SEQ ID NO: 1,
(ii) the promoter region of β-actin represented by the nucleotide sequence SEQ ID NO: 3, and (iii) the 5' UTR region represented by the nucleotide sequence SEQ ID NO: 9.

In a more particular embodiment of the invention, the expression vector according to the invention comprises a transcription unit comprising a nucleic acid represented by the sequence SEQ ID NO: 27 and consisting of:
(i) the hCMVie virus enhancer represented by the nucleotide sequence SEQ ID NO: 1,
(ii) the promoter region of β-actin represented by the nucleotide sequence SEQ ID NO: 3, and
(iii) the 5' UTR region represented by the nucleotide sequence SEQ ID NO: 10.

The present invention describes in particular an expression vector according to the invention comprising a transcription unit comprising a nucleic acid represented by the sequence SEQ ID NO: 14 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the R region of the LTR of the HTLV-1 virus represented by the nucleotide sequence SEQ ID NO: 4.

The present invention describes in particular an expression vector according to the invention comprising a transcription unit comprising a nucleic acid represented by the sequence SEQ ID NO: 15 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the 5' UTR region of the NF-κB Repressing Factor (NRF) gene having the nucleotide sequence SEQ ID NO: 5.

The present invention describes in particular an expression vector according to the invention comprising a transcription unit comprising a nucleic acid represented by the sequence SEQ ID NO: 16 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the 5' UTR region of the eukaryotic Initiation Factor 4GI (eIF4GI) gene having the nucleotide sequence SEQ ID NO: 6.

The present invention describes in particular an expression vector according to the invention comprising a transcription unit comprising a nucleic acid represented by the sequence SEQ ID NO: 18 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the 5' UTR region represented by the nucleotide sequence SEQ ID NO: 8.

The present invention describes in particular an expression vector according to the invention comprising a transcription unit comprising a nucleic acid represented by the sequence SEQ ID NO: 19 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the 5' UTR region represented by the nucleotide sequence SEQ ID NO: 9.

The present invention describes in particular an expression vector according to the invention comprising a transcription unit comprising a nucleic acid represented by the sequence SEQ ID NO: 20 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the 5' UTR region represented by the nucleotide sequence SEQ ID NO: 10.

The present invention describes in particular an expression vector according to the invention comprising a transcription unit comprising a nucleic acid represented by the sequence SEQ ID NO: 40 and consisting of:
(i) the hCMVie virus enhancer represented by the nucleotide sequence SEQ ID NO: 1,
(ii) the promoter region of the CDK9 gene represented by the nucleotide sequence SEQ ID NO: 2,
(iii) the 5' UTR region of the eukaryotic Initiation Factor 4GI (eIF4GI) gene having the nucleotide sequence SEQ ID NO: 6, and
(iv) the intron of the EF1α gene represented by the nucleotide sequence SEQ ID NO: 11.

The present invention describes in particular an expression vector according to the invention comprising a transcription unit comprising a nucleic acid represented by the sequence SEQ ID NO: 41 and consisting of:
(i) the hCMVie virus enhancer represented by the nucleotide sequence SEQ ID NO: 1,
(ii) the promoter region of the CDK9 gene represented by the nucleotide sequence SEQ ID NO: 2,
(iii) the 5' UTR region of the eukaryotic Initiation Factor 4GI (eIF4GI) gene having the nucleotide sequence SEQ ID NO: 6, and
(iv) the murine ROSA intron having the nucleotide sequence SEQ ID NO: 12.

The present invention describes in particular the expression vector according to the invention comprising a transcription unit comprising a nucleic acid represented by the sequence SEQ ID NO: 42 and consisting of:
(i) the hCMVie virus enhancer represented by the nucleotide sequence SEQ ID NO: 1,
(ii) the promoter region of the CDK9 gene represented by the nucleotide sequence SEQ ID NO: 2,
(iii) the 5' UTR region of the eukaryotic Initiation Factor 4GI (eIF4GI) gene having the nucleotide sequence SEQ ID NO: 6, and
(iv) the human ROSA intron having the nucleotide sequence SEQ ID NO: 13.

In a more particular embodiment of the invention, the expression vector according to the invention is a vector derived from pcDNA3.1 (Invitrogen) comprising a transcription unit comprising a nucleic acid represented by the sequence SEQ ID NO: 27 and consisting of:
(i) the hCMVie virus enhancer represented by the sequence SEQ ID NO: 1,
(ii) the promoter region of β-actin represented by the sequence SEQ ID NO: 3,
(iii) the 5' UTR region represented by the sequence SEQ ID NO: 10.

In a more particular embodiment of the invention, the expression vector according to the invention is a vector derived from pcDNA3.1 (Invitrogen) comprising a transcription unit comprising a nucleic acid represented by the sequence SEQ ID NO: 25 and consisting of:
(i) the hCMVie virus enhancer represented by the sequence SEQ ID NO: 1,
(ii) the promoter region of β-actin represented by the sequence SEQ ID NO: 3,
(iii) the 5' UTR region represented by the sequence SEQ ID NO: 8.

In a more particular embodiment of the invention, the expression vector according to the invention is a vector derived from pREP4 comprising a transcription unit comprising a nucleic acid represented by the sequence SEQ ID NO: 21 and consisting of:

(i) the hCMVie virus enhancer represented by the sequence SEQ ID NO: 1, (ii) the promoter region of β-actin represented by the sequence SEQ ID NO: 3, (iii) the R region of the LTR of the HTLV-1 virus represented by the nucleotide sequence SEQ ID NO: 4.

In a more particular embodiment of the invention, the expression vector according to the invention is a vector derived from pREP4 comprising a transcription unit comprising a nucleic acid represented by the sequence SEQ ID NO: 23 and consisting of:

(i) the hCMVie virus enhancer represented by the sequence SEQ ID NO: 1, (ii) the promoter region of β-actin represented by the sequence SEQ ID NO: 3, (iii) the 5' UTR region of the eukaryotic Initiation Factor 4GI (eIF4GI) gene having the nucleotide sequence SEQ ID NO: 6.

In a more particular embodiment of the invention, the expression vector according to the invention is a vector derived from pREP4 comprising a transcription unit comprising a nucleic acid represented by the sequence SEQ ID NO: 25 and consisting of:

(i) the hCMVie virus enhancer represented by the sequence SEQ ID NO: 1, (ii) the promoter region of β-actin represented by the sequence SEQ ID NO: 3, (iii) the 5' UTR region represented by the nucleotide sequence SEQ ID NO: 8.

In a more particular embodiment of the invention, the expression vector according to the invention is a vector derived from pREP4 comprising a transcription unit comprising a nucleic acid represented by the sequence SEQ ID NO: 16 and consisting of:

(i) the hCMVie virus enhancer represented by the sequence SEQ ID NO: 1, (ii) the promoter region of the CDK9 gene represented by the sequence SEQ ID NO: 2, (iii) the 5' UTR region of the eukaryotic Initiation Factor 4GI (eIF4GI) gene having the nucleotide sequence SEQ ID NO: 6.

In a more particular embodiment of the invention, the expression vector according to the invention is a vector derived from pREP4 comprising a transcription unit comprising a nucleic acid represented by the sequence SEQ ID NO: 18 and consisting of:

(i) the hCMVie virus enhancer represented by the sequence SEQ ID NO: 1, (ii) the promoter region of the CDK9 gene represented by the sequence SEQ ID NO: 2, (iii) the 5' UTR region represented by the nucleotide sequence SEQ ID NO: 8.

In a more particular embodiment of the invention, the expression vector according to the invention is a vector derived from pCEP4 comprising a transcription unit comprising a nucleic acid represented by the sequence SEQ ID NO: 25 and consisting of:

(i) the hCMVie virus enhancer represented by the sequence SEQ ID NO: 1, (ii) the promoter region of β-actin represented by the sequence SEQ ID NO: 3, (iii) the 5' UTR region represented by the nucleotide sequence SEQ ID NO: 8.

In a more particular embodiment of the invention, the expression vector according to the invention is a vector derived from pCEP4 comprising a transcription unit comprising a nucleic acid represented by the sequence SEQ ID NO: 25 and consisting of: (E2-bActin-U1U3)

(i) the hCMVie virus enhancer represented by the sequence SEQ ID NO: 1, (ii) the promoter region of β-actin represented by the sequence SEQ ID NO: 3, (iii) the 5' UTR region represented by the nucleotide sequence SEQ ID NO: 8.

The present invention also has the objective of supplying the host cells comprising an expression vector as described in the present invention.

Said host cells may be a cell line selected from CHO-S, CHO, or HEK.

The present invention also relates to the use of a transcription unit consisting of a polynucleotide comprising the following regulatory elements:

the hCMVie virus enhancer (E2), said enhancer having the nucleotide sequence SEQ ID NO: 1, or a nucleic acid having at least 70% sequence identity with the sequence SEQ ID NO: 1 and essentially possessing properties of transcription activation, and the promoter region of:

cyclin-dependent kinase 9 (CDK9), said promoter region having the nucleotide sequence SEQ ID NO: 2, or a nucleic acid having at least 70% sequence identity with SEQ ID NO: 2 and essentially possessing promoter activity for preparing expression vectors used in the transfection of a host cell of the CHO cell line.

More particularly, the invention relates to the use of a transcription unit as described above for preparing expression vectors used in the transfection of a host cell of the CHO cell line, in which said polynucleotide also comprises a nucleic acid located downstream of said promoter region and upstream of the translation initiation site, said nucleic acid comprising at least one of the untranslated 5' regions (5' UTR) selected from the following:

the regulatory region R of the Long Terminal Repeat (LTR) of the HTLV-1 virus having the nucleotide sequence SEQ ID NO: 4, or a nucleic acid having at least 70% sequence identity with SEQ ID NO: 4, the 5' UTR region of the NF-κB Repressing Factor (NRF) gene having the nucleotide sequence SEQ ID NO: 5, or a nucleic acid having at least 70% sequence identity with SEQ ID NO: 5, the 5' UTR region of the eukaryotic Initiation Factor 4GI (eIF4GI) gene having the nucleotide sequence SEQ ID NO: 6, or a nucleic acid having at least 70% sequence identity with SEQ ID NO: 6, the aforesaid nucleic acids having at least 70% sequence identity with one of the sequences represented by SEQ ID NO: 4, SEQ ID NO: 5 or SEQ ID NO: 6 essentially having properties of stabilization of the mRNA and of translation facilitator.

In a particular embodiment, the invention relates to the use of a transcription unit as described above, said transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and (iii) the R region of the Long Terminal Repeat (LTR) of the HTLV-1 virus represented by the nucleotide sequence SEQ ID NO: 4, or a nucleic acid having at least 70% sequence identity with the sequence SEQ ID NO: 4, said 5' UTR region being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 14 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region of the LTR of the HTLV-1 virus, represented by the sequence SEQ ID NO: 4, or of a nucleic acid having at least 70% sequence identity with the sequence SEQ ID NO: 14.

The transcription unit obtained is denoted by CMV-CDK9-U1, otherwise called E2-CDK9-U1.

In another particular embodiment, the invention relates to the use of a transcription unit as described above, said transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and (iii) the 5' UTR region of the NF-κB Repressing Factor (NRF) gene represented by the nucleotide sequence SEQ ID NO: 5, or a nucleic acid having at least 70% sequence identity with the sequence SEQ ID NO: 5, said 5' UTR region being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 15 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region of the NRF gene, represented by the sequence SEQ ID NO: 5, or a nucleic acid having at least 70% sequence identity with the sequence SEQ ID NO: 15. The transcription unit obtained is denoted by CMV-CDK9-U2, otherwise called E2-CDK9-U2.

In another particular embodiment, the invention relates to the use of a transcription unit as described above, said transcription unit being a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and (iii) the 5' UTR region of the eukaryotic Initiation Factor 4GI (eIF4GI) gene represented by the nucleotide sequence SEQ ID NO: 6, or a nucleic acid having at least 70% sequence identity with the sequence SEQ ID NO: 6, said 5' UTR region being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 16 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region of the eIF4GI gene represented by the sequence SEQ ID NO: 6, or of a nucleic acid having at least 70% sequence identity with the sequence SEQ ID NO: 16.

The transcription unit obtained is denoted by CMV-CDK9-U3, otherwise called E2-CDK9-U3.

In another particular embodiment, the invention relates to the use of a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus represented by the nucleotide sequence SEQ ID NO: 4, or a nucleic acid having at least 70% sequence identity with the sequence SEQ ID NO: 4, and (iv) the 5' UTR region of the NF-κB Repressing Factor (NRF) gene represented by the nucleotide sequence SEQ ID NO: 5, or a nucleic acid having at least 70% sequence identity with the sequence SEQ ID NO: 5, the 5' UTR regions being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 17 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 7, or of a nucleic acid having at least 70% sequence identity with the sequence SEQ ID NO: 17.

The transcription unit obtained is denoted by CMV-CDK9-U1U2, otherwise called E2-CDK9-U1U2.

In another particular embodiment, the invention relates to the use of a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 18 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 8, or of a nucleic acid having at least 70% sequence identity with the sequence SEQ ID NO: 18.

The transcription unit obtained is denoted by CMV-CDK9-U1U3, otherwise called E2-CDK9-U1U3.

In another particular embodiment, the invention relates to the use of a transcription unit comprising two 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 19 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 9, or of a nucleic acid having at least 70% sequence identity with the sequence SEQ ID NO: 19.

The transcription unit obtained is denoted by CMV-CDK9-U2U3, otherwise called E2-CDK9-U2U3.

In another particular embodiment, the invention relates to the use of a transcription unit according to the present invention that may comprise three 5' UTR regions. Such a transcription unit is constituted by a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, (iv) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (v) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, the 5' UTR regions being located downstream of the promoter region and upstream of the translation initiation site.

In a more particular embodiment, the invention relates to the use of a transcription unit as described above, said transcription unit consisting of a polynucleotide comprising a nucleic acid represented by the sequence SEQ ID NO: 20 and consisting of:

(i) the hCMVie virus enhancer represented by the sequence SEQ ID NO: 1, (ii) the promoter region of the CDK9 gene represented by the sequence SEQ ID NO: 2, and (iii) the 5' UTR region represented by the sequence SEQ ID NO: 10, or of a nucleic acid having at least 70% sequence identity with the sequence SEQ ID NO: 20.

The transcription unit obtained is denoted by CMV-CDK9-U1U2U3, otherwise called E2-CDK9-U1U2U3.

The invention also relates to the use of a transcription unit for preparing expression vectors used in the transfection of a host cell of the CHO cell line, said transcription unit comprising:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) a promoter region of cyclin-dependent kinase 9 (CDK9), said promoter region having the nucleotide sequence SEQ ID NO: 2, or a nucleic acid having at least 70% sequence identity with the sequence SEQ ID NO: 2 and essentially possessing promoter activity,
(iii) an intron selected from:
the intron of the Elongation Factor 1α (EF1α) gene having the nucleotide sequence SEQ ID NO: 11, or a nucleic acid having at least 70% sequence identity with the sequence SEQ ID NO: 11,
the murine ROSA intron having the nucleotide sequence SEQ ID NO: 12, or a nucleic acid having at least 70% sequence identity with the sequence SEQ ID NO: 12,
the human ROSA intron having the nucleotide sequence SEQ ID NO: 13, or a nucleic acid having at least 70% sequence identity with the sequence SEQ ID NO: 13,
said enhancer being located at 5' or at 3' of the transcription unit, or within the coding sequence or in an intron;
said intron being located:
(i) downstream of the 5' UTR region and upstream of the translation initiation site, or
(ii) downstream of the promoter and upstream of the 5' UTR region, or
(iii) after the translation initiation site and within the coding sequence, or
(iv) between the stop codon of the coding sequence and the polyadenylation signal.

In a particular embodiment, the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 28 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the intron of the EF1α gene represented by the nucleotide sequence SEQ ID NO: 11,
or of a nucleic acid having at least 70% sequence identity with the sequence SEQ ID NO: 28.

The transcription unit obtained is denoted by CMV-CDK9-EF1α, otherwise called E2-CDK9-EF.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the murine ROSA intron having the nucleotide sequence SEQ ID NO: 12,
or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 29 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the murine ROSA intron having the nucleotide sequence SEQ ID NO: 12,
or of a nucleic acid having at least 70% sequence identity with the sequence SEQ ID NO: 29.

The transcription unit obtained is denoted by CMV-CDK9-mROSA, otherwise called E2-CDK9-mROSA.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, and
(iii) the human ROSA intron having the nucleotide sequence SEQ ID NO: 13,
or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 30 and consisting of:
(i) the hCMVie virus enhancer represented by the nucleotide sequence SEQ ID NO: 1,
(ii) the promoter region of the CDK9 gene represented by the nucleotide sequence SEQ ID NO: 2, and
(iii) the human ROSA intron having the nucleotide sequence SEQ ID NO: 12,
or of a nucleic acid having at least 70% sequence identity with the sequence SEQ ID NO: 30.

The transcription unit obtained is denoted by CMV-CDK9-hROSA, otherwise called E2-CDK9-hROSA.

The invention also relates to the use of a transcription unit for transfection of a host cell of the CHO cell line, said transcription unit comprising:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) a promoter region of cyclin-dependent kinase 9 (CDK9), said promoter region having the nucleotide sequence SEQ ID NO: 2, or a nucleic acid having at least 70% sequence identity with the sequence SEQ ID NO: 2 and essentially possessing promoter activity,
  (iii) at least one of the untranslated 5' regions (5' UTR) selected from:
    the R region of the Long Terminal Repeat (LTR) of the HTLV-1 virus having the nucleotide sequence SEQ ID NO: 4, or a nucleic acid having at least 70% sequence identity with the sequence SEQ ID NO: 4,
    the 5' UTR region of the NF-κB Repressing Factor (NRF) gene having the nucleotide sequence SEQ ID NO: 5, or a nucleic acid having at least 70% sequence identity with the sequence SEQ ID NO: 5,
    the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
  (iv) an intron selected from:
    the intron of the Elongation Factor 1α (EF1α) gene having the nucleotide sequence SEQ ID NO: 11, or a nucleic acid having at least 70% sequence identity with the sequence SEQ ID NO: 11,
    the murine ROSA intron having the nucleotide sequence SEQ ID NO: 12, or a nucleic acid having at least 70% sequence identity with the sequence SEQ ID NO: 12,
    the human ROSA intron having the nucleotide sequence SEQ ID NO: 13, or a nucleic acid having at least 70% sequence identity with the sequence SEQ ID NO: 13,
said enhancer being located at 5' or at 3' of the transcription unit, or within the coding sequence or in an intron;
said promoter region being located upstream of the 5' UTR region;
said intron being located:
  (i) downstream of the 5' UTR region and upstream of the translation initiation site, or
  (ii) downstream of the promoter and upstream of the 5' UTR region, or
  (iii) after the translation initiation site and within the coding sequence, or
  (iv) between the stop codon of the coding sequence and the polyadenylation signal.

A particular embodiment of the invention relates to the use of a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
  (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
  (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and
  (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 34 and consisting of:
  (i) the hCMVie virus enhancer represented by the nucleotide sequence SEQ ID NO: 1,
  (ii) the promoter region of cyclin-dependent kinase 9 (CDK9) represented by the nucleotide sequence SEQ ID NO: 2,
  (iii) the R region of the LTR of the HTLV-1 virus having the nucleotide sequence SEQ ID NO: 4, and
  (iv) the intron of the Elongation Factor 1α (EF1α) gene having the nucleotide sequence SEQ ID NO: 11,
or of a nucleic acid having at least 70% sequence identity with the sequence SEQ ID NO: 34.

The transcription unit obtained is denoted by CMV-CDK9-U1-EF1α, otherwise called E2-CDK9-U1-EF.

A particular embodiment of the invention relates to the use of a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
  (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
  (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and
  (iv) the murine ROSA intron having the nucleotide sequence SEQ ID NO: 12,
or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 35 and consisting of:
  (i) the hCMVie virus enhancer represented by the nucleotide sequence SEQ ID NO: 1,
  (ii) the promoter region of cyclin-dependent kinase 9 (CDK9) represented by the nucleotide sequence SEQ ID NO: 2,
  (iii) the R region of the LTR of the HTLV-1 virus having the nucleotide sequence SEQ ID NO: 4, and
  (iv) the murine ROSA intron having the nucleotide sequence SEQ ID NO: 12,
or of a nucleic acid having at least 70% sequence identity with the sequence SEQ ID NO: 35.

The transcription unit obtained is denoted by CMV-CDK9-U1-mROSA, otherwise called E2-CDK9-U1-mROSA.

A particular embodiment of the invention relates to the use of a transcription unit consisting of a polynucleotide comprising the following regulatory elements:
  (i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and
  (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
  (iii) the R region of the Long Terminal Repeat (LTR) of the HTLV-1 virus having the nucleotide sequence SEQ ID NO: 4, or a nucleic acid having at least 70% sequence identity with the sequence SEQ ID NO: 4, and (iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 36 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the R region of the LTR of the HTLV-1 virus having the nucleotide sequence SEQ ID NO: 4, and (iv) the human ROSA intron having the nucleotide sequence SEQ ID NO: 13, or of a nucleic acid having at least 70% sequence identity with the sequence SEQ ID NO: 36.

The transcription unit obtained is denoted by CMV-CDK9-U1-hROSA, otherwise called E2-CDK9-U1-hROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 37 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region of the NRF gene having the nucleotide sequence SEQ ID NO: 5, and (iv) the intron of the Elongation Factor 1α (EF1α) gene having the nucleotide sequence SEQ ID NO: 11, or of a nucleic acid having at least 70% sequence identity with the sequence SEQ ID NO: 37.

The transcription unit obtained is denoted by CMV-CDK9-U2-EF1α, otherwise called E2-CDK9-U2-EF.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the murine ROSA intron having the nucleotide sequence SEQ ID NO: 12, or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 38 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region of the NRF gene having the nucleotide sequence SEQ ID NO: 5, and (iv) the murine ROSA intron having the nucleotide sequence SEQ ID NO: 12, or of a nucleic acid having at least 70% sequence identity with the sequence SEQ ID NO: 38.

The transcription unit obtained is denoted by CMV-CDK9-U2-mROSA, otherwise called E2-CDK9-U2-mROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region of the NF-κB Repressing Factor (NRF) gene having the nucleotide sequence SEQ ID NO: 5, or a nucleic acid having at least 70% sequence identity with the sequence SEQ ID NO: 5, and (iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 39 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region of the NRF gene having the nucleotide sequence SEQ ID NO: 5, and (iv) the human ROSA intron having the nucleotide sequence SEQ ID NO: 13, or of a nucleic acid having at least 70% sequence identity with the sequence SEQ ID NO: 39.

The transcription unit obtained is denoted by CMV-CDK9-U2-hROSA, otherwise called E2-CDK9-U2-hROSA.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 40 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the intron of the Elongation Factor 1α (EF1α) gene having the nucleotide sequence SEQ ID NO: 11,
or of a nucleic acid having at least 70% sequence identity with the sequence SEQ ID NO: 40, and essentially possessing properties of transcription activation superior to those of the CMV enhancer associated with the promoter region of CDK9.

The transcription unit obtained is denoted by CMV-CDK9-U3-EF1α, otherwise called E2-CDK9-U3-EF.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the murine ROSA intron having the nucleotide sequence SEQ ID NO: 12,
or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 41 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the murine ROSA intron having the nucleotide sequence SEQ ID NO: 12,
or of a nucleic acid having at least 70% sequence identity with the sequence SEQ ID NO: 41.

The transcription unit obtained is denoted by CMV-CDK9-U3-mROSA, otherwise called E2-CDK9-U3-mROSA.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region of the eukaryotic Initiation Factor 4GI (eIF4GI) gene having the nucleotide sequence SEQ ID NO: 6, or a nucleic acid having at least 70% sequence identity with the sequence SEQ ID NO: 6, and
(iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 42 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region of the eIF4GI gene having the nucleotide sequence SEQ ID NO: 6, and
(iv) the human ROSA intron having the nucleotide sequence SEQ ID NO: 13,
or of a nucleic acid having at least 70% sequence identity with the sequence SEQ ID NO: 42.

The transcription unit obtained is denoted by CMV-CDK9-U3-hROSA, otherwise called E2-CDK9-U3-hROSA.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 43 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the intron of the Elongation Factor 1α (EF1α) gene having the nucleotide sequence SEQ ID NO: 11, or of a nucleic acid having at least 70% sequence identity with the sequence SEQ ID NO: 43.

The transcription unit obtained is denoted by CMV-CDK9-U1U2-EF1α, otherwise called E2-CDK9-U1U2-EF.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, and (iv) the murine ROSA intron having the nucleotide sequence SEQ ID NO: 12, or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 44 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the murine ROSA intron having the nucleotide sequence SEQ ID NO: 12, or of a nucleic acid having at least 70% sequence identity with the sequence SEQ ID NO: 44.

The transcription unit obtained is denoted by CMV-CDK9-U1U2-mROSA, otherwise called E2-CDK9-U1U2-mROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 7, or a nucleic acid having at least 70% sequence identity with the sequence SEQ ID NO: 7, and (iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 45 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 7, and (iv) the human ROSA intron having the nucleotide sequence SEQ ID NO: 13, or of a nucleic acid having at least 70% sequence identity with the sequence SEQ ID NO: 45.

The transcription unit obtained is denoted by CMV-CDK9-U1U2-hROSA, otherwise called E2-CDK9-U1U2-hROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 8, or a nucleic acid having at least 70% sequence identity with the sequence SEQ ID NO: 8, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 46 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 8, and (iv) the intron of the Elongation Factor 1α (EF1α) gene having the nucleotide sequence SEQ ID NO: 11, or of a nucleic acid having at least 70% sequence identity with the sequence SEQ ID NO: 46.

The transcription unit obtained is denoted by CMV-CDK9-U1U3-EF1α, otherwise called E2-CDK9-U1U3-EF.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 8, or a nucleic acid having at least 70% sequence identity with the sequence SEQ ID NO: 8, and (iv) the murine ROSA intron having the nucleotide sequence SEQ ID NO: 12, or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 47 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 8, and (iv) the murine ROSA intron having the nucleotide sequence SEQ ID NO: 12, or of a nucleic acid having at least 70% sequence identity with the sequence SEQ ID NO: 47.

The transcription unit obtained is denoted by CMV-CDK9-U1U3-mROSA, otherwise called E2-CDK9-U1U3-mROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, and (iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 48 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 8, and (iv) the human ROSA intron having the nucleotide sequence SEQ ID NO: 13, or of a nucleic acid having at least 70% sequence identity with the sequence SEQ ID NO: 48.

The transcription unit obtained is denoted by CMV-CDK9-U1U3-hROSA, otherwise called E2-CDK9-U1U3-hROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, and (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 49 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 9, and (iv) the intron of the Elongation Factor 1α (EF1α) gene having the nucleotide sequence SEQ ID NO: 11, or of a nucleic acid having at least 70% sequence identity with the sequence SEQ ID NO: 49.

The transcription unit obtained is denoted by CMV-CDK9-U2U3-EF1α, otherwise called E2-CDK9-U2U3-EF.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, (iv) the murine ROSA intron having the nucleotide sequence SEQ ID NO: 12, or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 50 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 9, and (iv) the murine ROSA intron having the nucleotide sequence SEQ ID NO: 12, or of a nucleic acid having at least 70% sequence identity with the sequence SEQ ID NO: 50.

The transcription unit obtained is denoted by CMV-CDK9-U2U3-mROSA, otherwise called E2-CDK9-U2U3-mROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 9, or a nucleic acid having at least 70% sequence identity with the sequence SEQ ID NO: 9, and (iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 51 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 9, and (iv) the human ROSA intron having the nucleotide sequence SEQ ID NO: 13, or of a nucleic acid having at least 70% sequence identity with the sequence SEQ ID NO: 51.

The transcription unit obtained is denoted by CMV-CDK9-U2U3-hROSA, otherwise called E2-CDK9-U2U3-hROSA.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 10, or a nucleic acid having at least 70% sequence identity with the sequence SEQ ID NO: 10, and (iv) the intron of the Elongation Factor 1α (EF1α) gene having the nucleotide sequence SEQ ID NO: 11, or a nucleic acid having at least 70% sequence identity with the sequence SEQ ID NO: 11.

In a more particular embodiment, the invention relates to the use of a transcription unit consisting of a polynucleotide comprising a nucleic acid represented by the sequence SEQ ID NO: 52 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 10, and (iv) the intron of the Elongation Factor 1α (EF1α) gene having the nucleotide sequence SEQ ID NO: 11, or of a nucleic acid having at least 70% sequence identity with the sequence SEQ ID NO: 52.

The transcription unit obtained is denoted by CMV-CDK9-U1U2U3-EF1α, otherwise called E2-CDK9-U1U2U3-EF.

A particular embodiment of the invention relates to the use of a transcription unit consisting of a polynucleotide comprising the following regulatory elements:

(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation, (ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity, (iii) the 5' UTR region represented by the sequence SEQ ID NO: 10, or a nucleic acid having at least 70% sequence identity with the sequence SEQ ID NO: 10, and (iv) the murine ROSA intron having the nucleotide sequence SEQ ID NO: 12, or a nucleic acid having at least 70% sequence identity with the sequence SEQ ID NO: 12.

In a more particular embodiment, the invention relates to the use of a transcription unit consisting of a polynucleotide comprising a nucleic acid represented by the sequence SEQ ID NO: 53 and consisting of:

(i) the hCMVie virus enhancer represented by the nucleotide sequence SEQ ID NO: 1, (ii) the promoter region of cyclin-dependent kinase 9 (CDK9) represented by the nucleotide sequence SEQ ID NO: 2, (iii) the 5' UTR region represented by the nucleotide sequence SEQ ID NO: 10, and (iv) the murine ROSA intron having the nucleotide sequence SEQ ID NO: 12, or of a nucleic acid having at least 70% sequence identity with the sequence SEQ ID NO: 53.

The transcription unit obtained is denoted by CMV-CDK9-U1U2U3-mROSA, otherwise called E2-CDK9-U1U2U3-mROSA.

A particular embodiment of the invention relates to the use of a transcription unit consisting of a polynucleotide comprising the following regulatory elements:
(i) the hCMVie virus enhancer represented by the nucleotide sequence SEQ ID NO: 1, or a nucleic acid having at least 70% sequence identity with the sequence SEQ ID NO: 1 and essentially possessing properties of transcription activation,
(ii) the promoter region of cyclin-dependent kinase 9 (CDK9) represented by the nucleotide sequence SEQ ID NO: 2, or a nucleic acid having at least 70% sequence identity with the sequence SEQ ID NO: 2 and essentially possessing promoter activity,
(iii) the 5' UTR region represented by the sequence SEQ ID NO: 10, or a nucleic acid having at least 70% sequence identity with the sequence SEQ ID NO: 10, and
(iv) the human ROSA intron having the nucleotide sequence SEQ ID NO: 13, or a nucleic acid having at least 70% sequence identity with the sequence SEQ ID NO: 13.

In a more particular embodiment, the invention relates to the use of a transcription unit consisting of a polynucleotide comprising a nucleic acid represented by the sequence SEQ ID NO: 54 and consisting of:
(i) the hCMVie virus enhancer represented by the nucleotide sequence SEQ ID NO: 1,
(ii) the promoter region of cyclin-dependent kinase 9 (CDK9) represented by the nucleotide sequence SEQ ID NO: 2,
(iii) the 5' UTR region represented by the nucleotide sequence SEQ ID NO: 10, and
(iv) the human ROSA intron having the nucleotide sequence SEQ ID NO: 13,
or of a nucleic acid having at least 70% sequence identity with the sequence SEQ ID NO: 54.

The transcription unit obtained is denoted by CMV-CDK9-U1U2U3-hROSA, otherwise called E2-CDK9-U1U2U3-hROSA.

In a more particular embodiment, the invention relates to the use of a transcription unit containing the promoter region of the CKD9 gene, the 5' UTR region of the eIF4GI gene (U3) and the intron of the EF1α gene for transfection of a host cell of the CHO cell line selected from CHO-S, CHO, said transcription unit allowing volume-based production of a protein of interest greater than that obtained with the combination of the CMV enhancer associated with the promoter region of CDK9.

In an even more particular embodiment, the invention relates to the use of a transcription unit having the nucleotide sequence SEQ ID NO: 40, or a nucleotide sequence having at least 70% identity with SEQ ID NO: 40 for transfection of a host cell of the CHO cell line selected from CHO-S, CHO, said transcription unit allowing volume-based production of a protein of interest greater than that obtained with the combination of the CMV enhancer associated with the promoter region of CDK9.

The CHO cell line used in the present invention may be selected from CHO-S, CHO.

The present invention also relates to the use of an expression vector described above for transfecting a host cell.

Another objective of the present invention is to provide an expression system comprising an expression vector according to the present invention and a host cell as described above, allowing the expression of a protein of interest encoded by a nucleic acid.

The present invention also relates to the use of an expression vector comprising at least one transcription unit according to the present invention in a host cell as described above for producing a protein encoded by a nucleic acid, said protein being produced with a titre higher than in the reference expression vector comprising at least one RSV promoter, a pCIneo intron, a polyadenylation sequence, a eukaryotic resistance gene, a bacterial resistance gene, a bacterial replication origin and a unit dedicated to gene amplification, said reference vector comprising the same nucleotide sequence.

The present invention also relates to a method for the in vitro production of a recombinant protein of interest comprising the steps of:
 introducing the expression vector comprising at least one transcription unit according to the present invention and a cDNA coding for a protein of interest into a host cell,
 selecting and identifying the host cells obtained in the preceding step stably expressing said protein of interest,
 extracting and purifying said protein of interest.

Such a recombinant protein may be a protein participating in coagulation, an immunoglobulin, cytokines, hormones, growth factors or complement factors and any fusion protein.

A method according to the present invention may further comprise a step of selecting and identifying the host cells obtained that stably express said protein of interest.

The present invention is illustrated by the figures and examples given below. However, the present invention is not in any way limited to the figures and examples given below.

FIGURES

Figure 29:
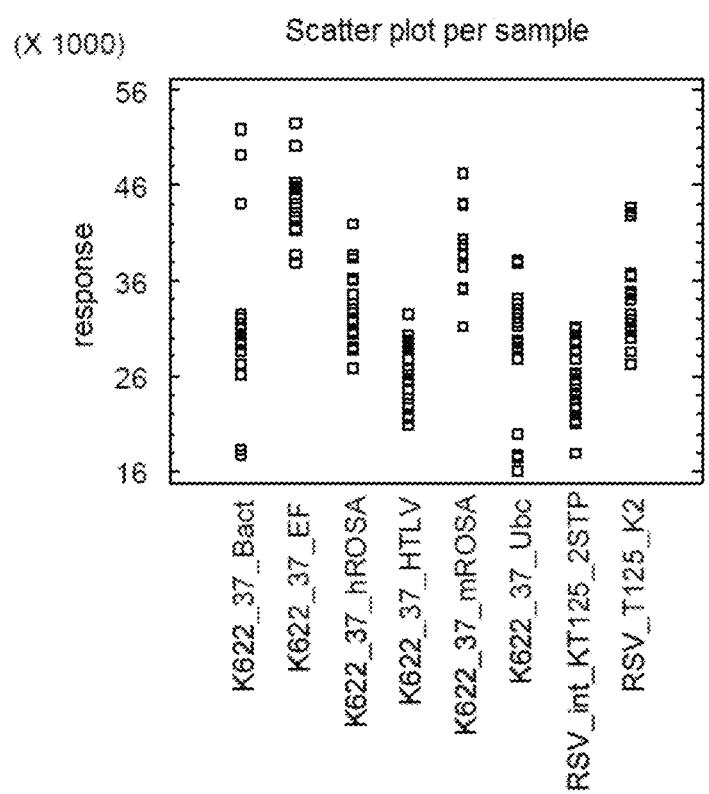

FIG. 29 illustrates the comparison of the effect of different introns in association with LTR RSV on expression of the free kappa chain of the anti-Rh(D) T125 antibody in the CHO-S line evaluated in transient transfection. The columns of points, from left to right, represent respectively the expression level of the free kappa chain under the control of the introns: β-actin (Bact), EF, mROSA, hROSA, HTLV, ubiquitin (ubc). The reference vectors are RSV_int_KT125_2STP and RSV_T125_K2. The y-axis shows the concentration of free kappa chains in the culture medium.

Figure 30:
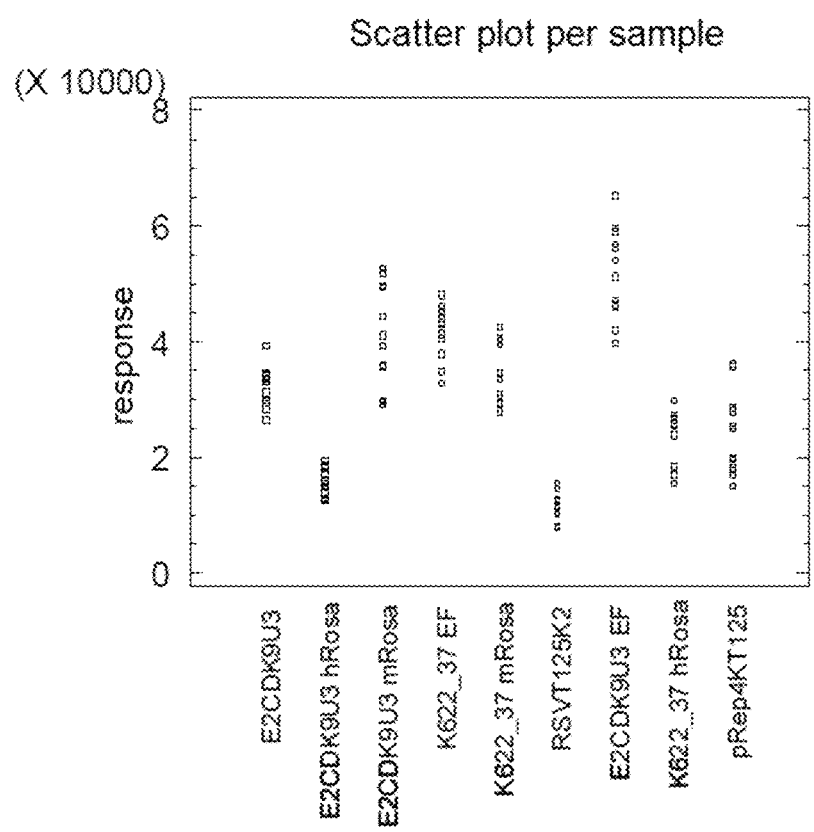

FIG. 30 illustrates comparison of the effect of different introns in association with the transcription unit E-2CDK9-U3 or LTR RSV on expression of the free kappa chain of the anti-Rh(D) T125 antibody in the CHO-S line evaluated in transient transfection. The columns of points, from left to right, represent respectively the expression level of the free kappa chain under the control of the combinations: E2-CDK9-U3 without intron, E2-CDK9-U3 with hROSA intron, E2-CDK9-U3 with mROSA intron, LTR RSV with EF intron, LTR RSV with mROSA intron, E2-CDK9-U3 with EF intron, LTR RSV with hROSA intron. The reference vectors are RSV_T125_K2 and pRep4KT125. The y-axis shows the concentration of free kappa chains in the culture medium.

Figure 31:
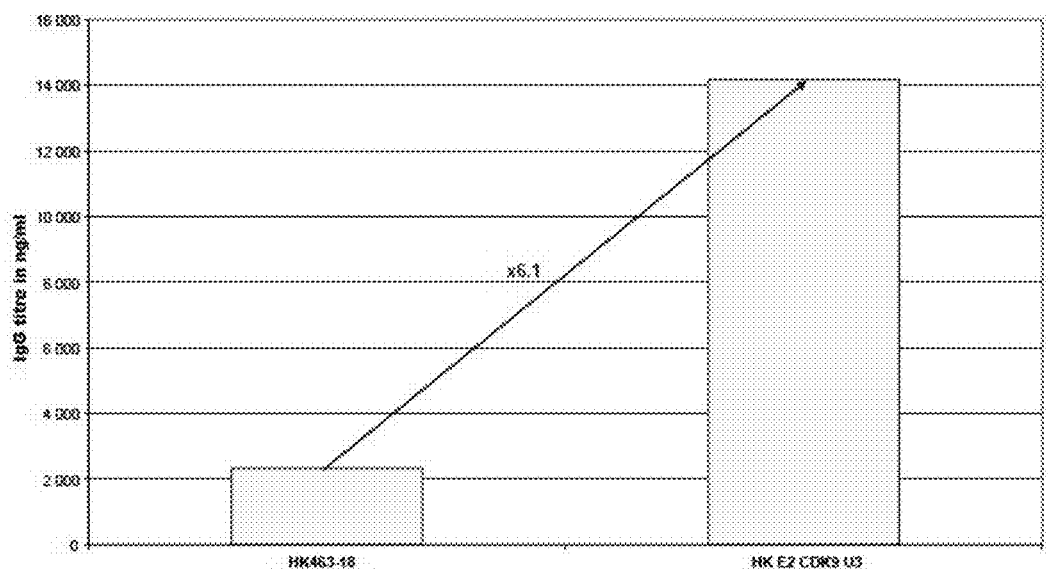

FIG. 31 illustrates comparison of expression as stable pools of transfectants expressing IgG anti-D as a function of the vector (E2CDK9U3/LTR RSV intron pCI neo) and more precisely the productivity as stable pools of the whole antibody anti-Rh(D) T125 with the vector with transcription unit E2-CDK9-U3 (HK E2 CDK9 U3) in comparison with the reference with LTR RSV intron pCI neo (HK463-18).

Figure 32:
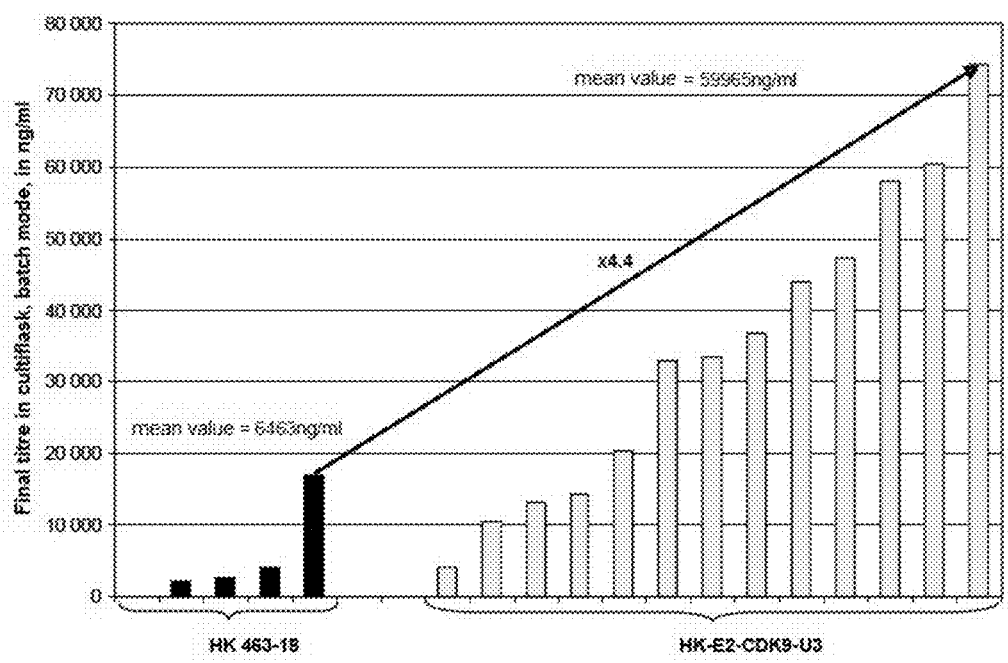

FIG. 32 is a distribution diagram of the transfectants expressing IgG anti-D as a function of the vector (E2CDK9U3/LTR RSV intron pCI neo). This diagram illustrates the productivity of clones producing the whole antibody anti-Rh(D) T125 with the vector with transcription unit E2-CDK9-U3 (HK E2 CDK9 U3) in comparison with the reference with LTR RSV intron pCI neo (HK463-18).

Figure 33:
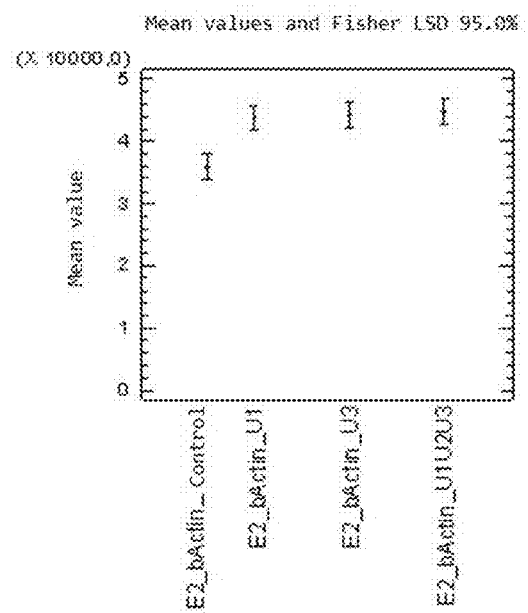

FIG. 33 illustrates the mean titres of kappa chains T125 obtained in the CHO-S line transfected by a vector containing a respective transcription unit given below: E2-bActin-Control, E2-bActin-U1, E2-bActin-U3, E2-bActin-U1U2U3. The result is evaluated on the basis of three independent experiments of transient transfection in triplicate. The y-axis shows the concentration of free kappa chains in the culture medium. P-value<0.05, n=10 to 13.

Figure 34:
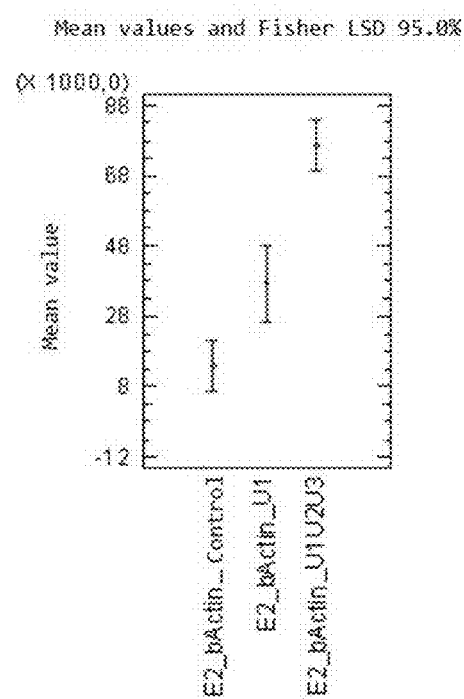

FIG. 34 illustrates the mean titres of kappa chains T125 obtained in the HEK line transfected by a vector containing a respective transcription unit given below: E2-bActin-Control, E2-bActin-U1, E2-bActin-U1U2U3. The result is evaluated on the basis of three independent experiments of transient transfection in triplicate. The y-axis shows the concentration of free kappa chains in the culture medium. P-value<0.05, n=10 to 15.

Figure 35:
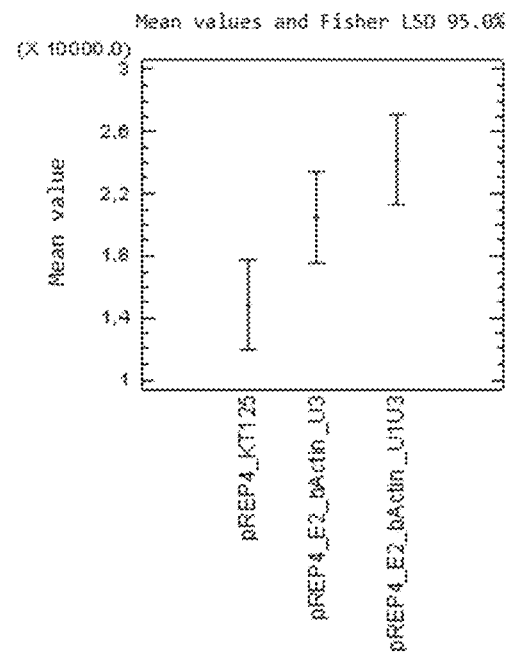

FIG. 35 illustrates the mean titres of kappa chains T125 obtained in the CHO-S line transfected respectively by the vector pREP4-KT125, pREP4-E2-bActin-U3, pREP4-E2-U1U3. The result is evaluated on the basis of three independent experiments of transient transfection in triplicate. The y-axis shows the concentration of free kappa chains in the culture medium. P-value<0.05, n=6.

Figure 36:
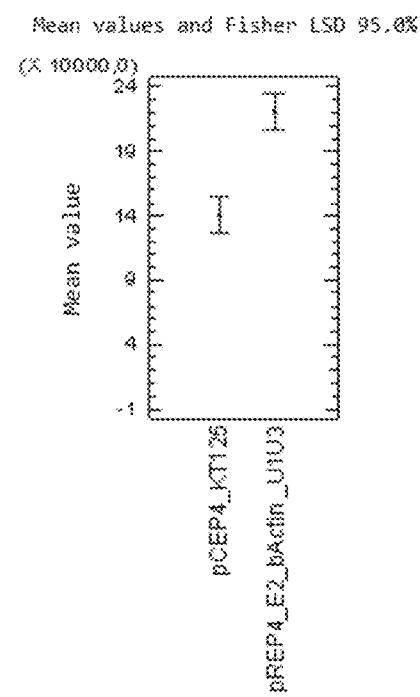

FIG. 36 illustrates the mean titres of kappa chains T125 obtained in the HEK line transfected respectively by the vector pCEP4-KT125, pCEP4-E2-bActin-U1U3. The result is evaluated on the basis of three independent experiments of transient transfection in triplicate. The y-axis shows the concentration of free kappa chains in the culture medium. P-value<0.05, n=6.

EXAMPLES

1. Materials and Methods 1.1. Transient Transfection

In CHO-S, the sequences to be expressed are evaluated in transient transfection according to the protocol of the FreeStyle kit (Invitrogen). The parent cells are seeded 24 h before transfection (D-1) in a conical flask (VWR) at $6^E5$ live cells/ml in FreeStyle CHO EM (Fisher Bioblock Scientific) and incubated at 120 r.p.m. 37° C., 8% $CO_2$. On the day of transfection, a FreeStyle MAX Reagent (Fisher Bioblock Scientific)/DNA complex, at 1:1 ratio, is formed in Opti Pro SFM (Invitrogen). The complex is then deposited on the previously centrifuged cells in suspension and taken up at $1^E6$ live cells/ml in FreeStyle CHO EM in a Cultiflask (Sartorius) (5 ml) and incubated at 200 r.p.m. at 37° C., 8% $CO_2$. The supernatants are collected on D+5 for evaluating the level of molecule secreted in the medium.

1.2. Stable Transfection

The evaluations are carried out on pools of transfectants ("transfection in stable pool") in order to compare the different constructs based on an expression level averaged over a large number of transfectants (several thousand) as well as for the best clones selected by ClonePixFL from these pools.

1.2.1. Obtaining the Pools and Evaluations in Pools

The CHO-S line is cultured in FreeStyle CHO EM medium+8 mM of glutamine, in a flask at 37° C., 8% $CO_2$, with stirring at 135 rpm.

The cells are subcultured on the previous day at $6 \times 10^5$ cells/ml.

On the day of electroporation, the cells are electroporated by Gene Pulser Xcell (BioRad) at a voltage of 300 V and a capacitance of 500 µF in 4-mm cuvettes (Biorad) with 5E6 live cells (q.s. 500 µl of electroporation buffer from the electrobuffer kit (Ozyme) containing linearized plasmid DNA). After electroporation, the cells are taken up at 3E5 live cells/ml in an F75 culture bottle.

On D+3: Putting in selective medium in order to obtain the following final concentrations: FreeStyle CHO EM+additives LFB for low-density cell cloning LDCC+G418 1 mg/ml.

On D+10: Dilution by half in FreeStyle CHO EM+additives LFB for low-density cell cloning LDCC+G418 1 mg/ml.

Starting from D+12 and 3 times per week: if the cell density is above 6E5 live cells/ml, transfer the cells at 3E5 live cells/ml to F25.

Starting from D+17 transfer to F25 or F75 bottle in FreeStyle CHO EM+G418 1 mg/ml.

Starting from D+25, carry out production in batch mode: inoculate the F25s to $3^E5$ live cells/ml in FreeStyle CHO EM+G418 1 mg/ml (production in pool).

The supernatant is collected at D+12 and assayed with the Fast ELYSA kit (RD-biotech).

1.2.2. Obtaining Clones and Evaluations of the Clones

The pools of cells obtained previously are spread out on semisolid medium (CloneMedia CHO—Molecular Devices) in the presence of fluorescent detection antibody.

The clones that are the strongest producers in each pool are selected firstly as a function of their fluorescence intensity (screening and picking by ClonePix$^{FL}$) and then as a function of their titre at saturation in P24.

The best clones are then evaluated in production in batch mode by inoculation of Cultiflasks at $3^E5$ live cells/ml in FreeStyle CHO EM+G418 1 mg/ml and culture with stirring at 250 r.p.m.

The supernatant is collected when viability is below 50% and assayed with the Fast ELYSA kit (RD-biotech).

1.3. Evaluation of the Level of Recombinant Protein Secreted

Evaluation of the level of free kappa chain of the anti-Rh(D) T125 antibody as well as the production of IgG1 of anti-CD20 or of anti-Rh(D) T125 are determined by the enzyme-linked immunosorbent assay (ELISA) technique.

The free kappa chain present in the culture supernatant is captured over a period of 2 h by an anti-human kappa goat antibody (Caltag Lab), which is adsorbed on 96-well plates. The antibody captured is then detected by a biotinylated goat anti-human kappa (Pierce) and then the addition of peroxidase-coupled streptavidin (Pierce). Between each step, 4 washings are carried out to remove the proteins and reagents not included in the complex. Detection is performed by adding the enzyme substrate, OPD (Sigma) and the reaction is stopped with 1N HCl. Reading is carried out with the spectrophotometer at 492 nm. The concentration of antibody is determined by comparison with a standard range.

The IgG1s produced in transient and stable transfections are evaluated using the Fast ELYSA kit (RD-biotech) according to the supplier's instructions. The optical density is read with a spectrophotometer at 450 nm. The concentration of antibody is determined by comparison with a standard range contained in the kit.

1.4. Statistical Analyses

The results for the production of free kappa chain or whole immunoglobulins are compared based on values normalized by the medians from one experiment to another. The statistical analyses are performed using the STATGRAPHICS Centurion XV software. Multiple extended tests are applied to the data with the 95.0% LSD method. The pairs of data have statistically significant differences at the 95.0% confidence level.

Example 1

Figure 6:
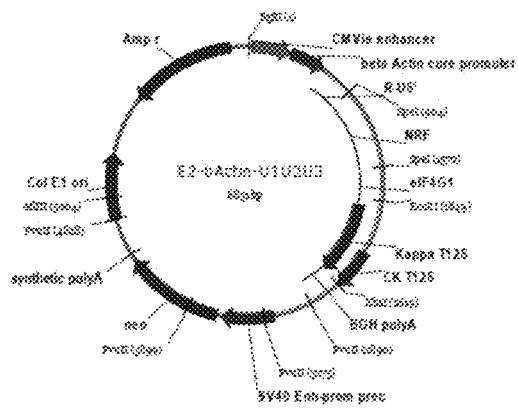
FIG. 6 illustrates the vector E2-bActin-U1U2U3 comprising a transcription unit comprising the hCMVie enhancer, the promoter region of β-actin, the R region of the LTR of the HTLV-1 virus, the 5' UTR region of the NRF gene and the 5' UTR region of the eIF4G1 gene.

Construction of the Vector E2-bActin-U1U2U3 (FIG. 6)

Digestion of the vector E2-bActin with BamHI+NheI
Recovery of the fragment with 5560 bases and removal of the fragment with 204 bases
Digestion of the synthetic insert with BamHI+NheI
Recovery on gel of the insert with 1271 bases
Ligation and obtaining E2-bActin-U1U2U3
Screening by PCR with suitable primers, which gives an amplicon with 944 bases Example 2

Figure 1:
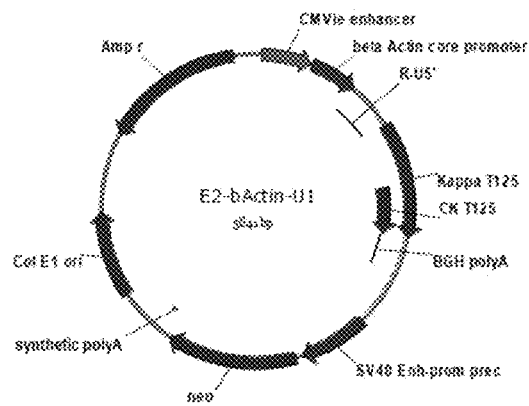
FIG. 1 illustrates the vector E2-bActin-U1 comprising a transcription unit comprising the hCMVie enhancer, the promoter region of β-actin and the R region of the LTR of the HTLV-1 virus.

Construction of the Vector E2-bActin-U1 (FIG. 1)

Digestion SpeI+NheI E2-bActin-U1U2U3
Recovery on gel of the fragment with 5841 bases, removal of the fragment with 990 bases
Ligation and obtaining E2-bActin-U1
Screening by PCR with suitable primers, which gives an amplicon with 1118 bases Example 3

Figure 3:
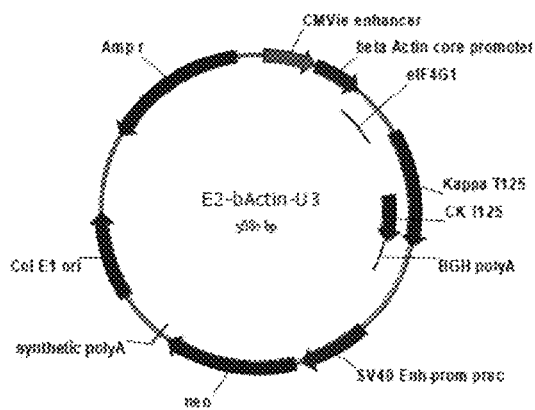
FIG. 3 illustrates the vector E2-bActin-U3 comprising a transcription unit comprising the hCMVie enhancer, the promoter region of β-actin and the 5' UTR region of the eIF4G1 gene.

Construction of the Vector E2-bActin-U3 (FIG. 3)

Digestion HpaI+PmeI on E2-bActin-U1U2U3
Recovery on gel of the fragment with 5887 bases, removal of the fragment with 944 bases
Ligation and obtaining E2-bActin-U3
Screening by PCR with suitable primers, which gives an amplicon with 1164 bases Example 4

Figure 5:
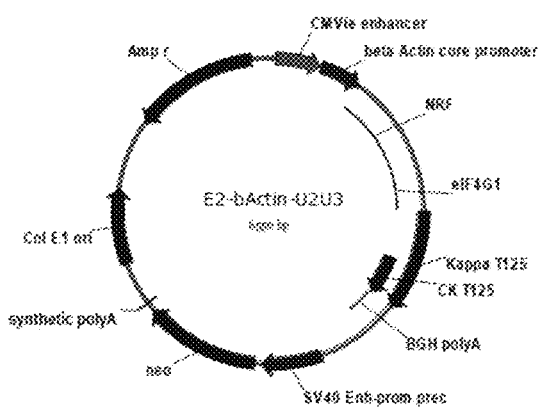
FIG. 5 illustrates the vector E2-bActin-U2U3 comprising a transcription unit comprising the hCMVie enhancer, the promoter region of β-actin, the 5' UTR region of the NRF gene and the 5' UTR region of the eIF4G1 gene.

Construction of the Vector E2-bActin-U2U3 (FIG. 5)

Digestion PmeI on E2-bActin-U1U2U3
Recovery of the fragment with 6550 bases and removal of the fragment with 281 bases
Ligation and obtaining E2-bActin-U2U3
Screening by PCR with suitable primers, which gives an amplicon with 1468 bases Example 5

Figure 2:
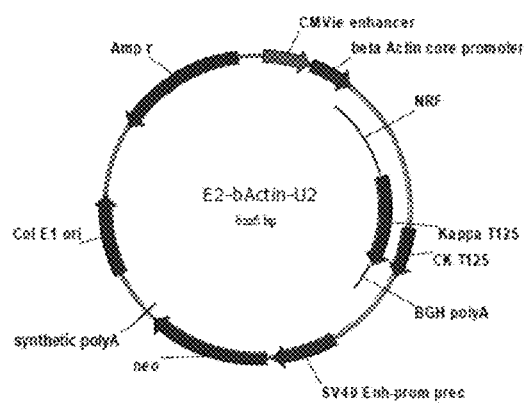
FIG. 2 illustrates the vector E2-bActin-U2 comprising a transcription unit comprising the hCMVie enhancer, the promoter region of β-actin and the 5' UTR region of the NRF gene.

Construction of the Vector E2-bActin-U2 (FIG. 2)

Digestion SpeI+NheI of E2-bActin-U2U3
Recovery on gel of the fragment with 6226 bases, removal of the fragment with 324 bases
Ligation and obtaining E2-bActin-U2
Screening by PCR with suitable primers, which gives an amplicon with 1468 bases Example 6

Figure 4:
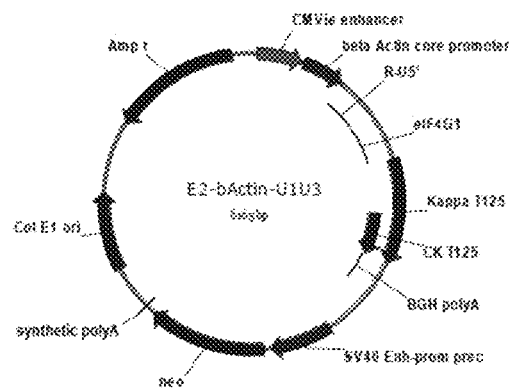
FIG. 4 illustrates the vector E2-bActin-U1U3 comprising a transcription unit comprising the hCMVie enhancer, the promoter region of β-actin, the R region of the LTR of the HTLV-1 virus and the 5' UTR region of the eIF4G1 gene.

Construction of the Vector E2-bActin-U1U3 (FIG. 4)

Digestion SpeI on E2-bActin-U1U2U3
Recovery on gel of the fragment with 6165 bases, removal of the fragment with 666 bases
Ligation and obtaining E2-bActin-U1U3
Screening by PCR with suitable primers, which gives an amplicon with 578 bases Example 7

Figure 12:
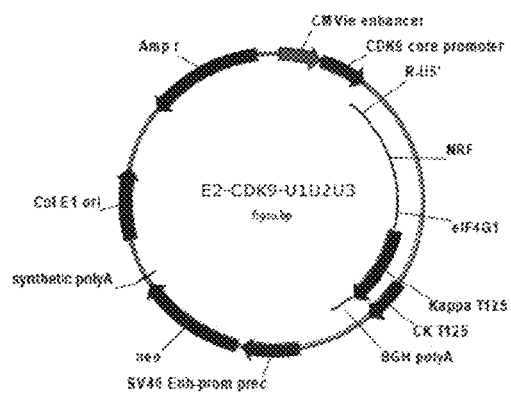
FIG. 12 illustrates the vector E2-CDK9-U1U2U3 comprising a transcription unit comprising the hCMVie enhancer, the promoter region of the CDK9 gene, the R region of the LTR of the HTLV-1 virus, the 5' UTR region of the NRF gene and the 5' UTR region of the eIF4G1 gene.

Construction of the Vector E2-CDK9-U1U2U3 (FIG. 12)

Digestion of the vector E2-CDK9 with BamHI and NheI
Recovery of the fragment with 5630 bases, removal of the fragment with 204 bases
Digestion of the synthetic insert with BamHI and NheI
Recovery on gel of the insert with 1271 bases
Ligation and obtaining E2-CDK9-U1U2U3
Screening by PCR with suitable primers, which gives an amplicon with 1014 bases Example 8

Figure 11:
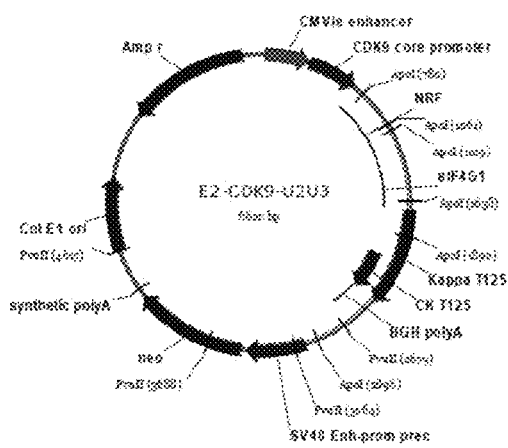
FIG. 11 illustrates the vector E2-CDK9-U2U3 comprising a transcription unit comprising the hCMVie enhancer, the promoter region of the CDK9 gene, the 5' UTR region of the NRF gene and the 5' UTR region of the eIF4G1 gene.

Construction of the Vector E2-CDK9-U2U3 (FIG. 11)

Digestion PmeI on E2-CDK9-U1U2U3
Recovery of the fragment with 6620 bases and removal of the fragment with 281 bases
Ligation and obtaining E2-CDK9-U2U3
Screening by PCR with suitable primers, which gives an amplicon with 1538 bases Example 9

Figure 8:
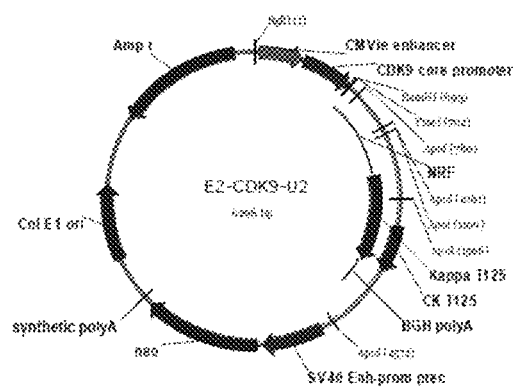
FIG. 8 illustrates the vector E2-CDK9-U2 comprising a transcription unit comprising the hCMVie enhancer, the promoter region of the CDK9 gene and the 5' UTR region of the NRF gene.

Construction of the Vector E2-CDK9-U2 (FIG. 8)

Digestion SpeI+NheI of E2-CDK9-U2U3
Recovery on gel of the fragment with 6296 bases, removal of the fragment with 324 bases
Ligation and obtaining E2-CDK9-U2
Screening by PCR with suitable primers, which gives an amplicon with 686 bases Example 10

Figure 7:
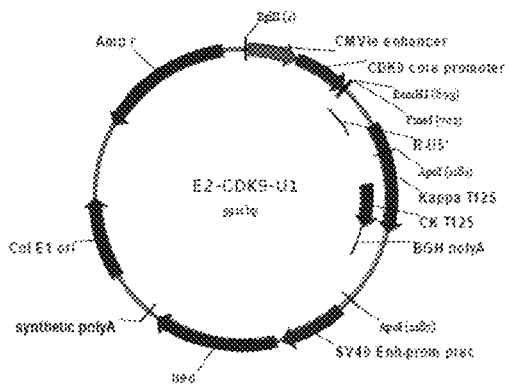
FIG. 7 illustrates the vector E2-CDK9-U1 comprising a transcription unit comprising the hCMVie enhancer, the promoter region of the CDK9 gene and the R region of the LTR of the HTLV-1 virus.

Construction of the Vector E2-CDK9-U1 (FIG. 7)

Digestion SpeI+NheI on E2-CDK9-U1U2U3
Recovery on gel of the fragment with 5911 bases, removal of the fragment with 990 bases
Ligation and obtaining E2-CDK9-U1
Screening by PCR with suitable primers, which gives an amplicon with 254 bases Example 11

Figure 9:
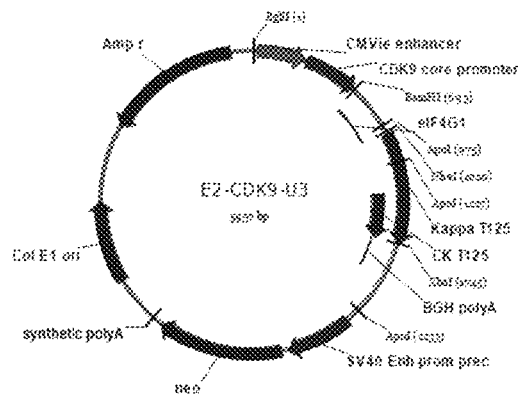
FIG. 9 illustrates the vector E2-CDK9-U3 comprising a transcription unit comprising the hCMVie enhancer, the promoter region of the CDK9 gene and the 5' UTR region of the eIF4G1 gene.

Construction of the Vector E2-CDK9-U3 (FIG. 9)

Digestion HpaI+PmeI on E2-CDK9-U1U2U3
Recovery on gel of the fragment with 5957 bases, removal of the fragment with 944 bases
Ligation and obtaining E2-CDK9-U3
Screening by PCR with suitable primers, which gives an amplicon with 1234 bases

Example 12

Figure 10:
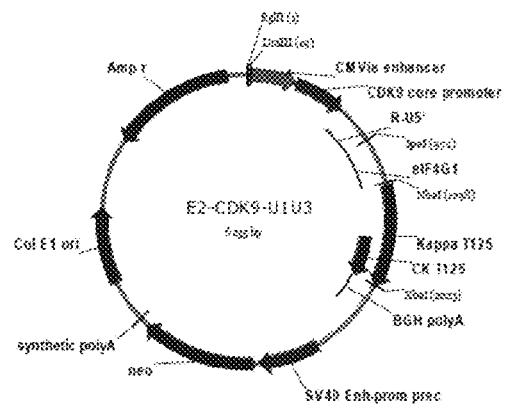
FIG. 10 illustrates the vector E2-CDK9-U1U3 comprising a transcription unit comprising the hCMVie enhancer, the promoter region of the CDK9 gene, the R region of the LTR of the HTLV-1 virus and the 5' UTR region of the eIF4G1 gene.

Construction of the Vector E2-CDK9-U1U3 (FIG. 10)

Digestion SpeI on E2-CDK9-U1U2U3
Recovery on gel of the fragment with 6235 bases, removal of the fragment with 666 bases
Ligation and obtaining E2-CDK9-U1U3
Screening by PCR with suitable primers, which gives an amplicon with 578 bases

Example 13

Figure 13:
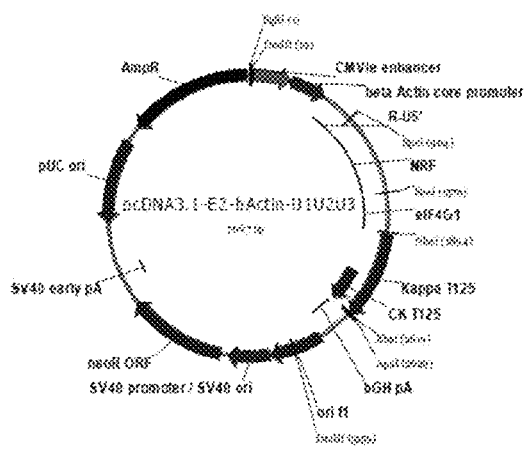
FIG. 13 illustrates the vector pcDNA3.1-E2-bActin-U1U2U3 originating from the vector pcDNA3.1 Invitrogen, comprising a transcription unit comprising the hCMVie enhancer, the promoter region of the CDK9 gene, the R region of the LTR of the HTLV-1 virus, the 5' UTR region of the NRF gene and the 5' UTR region of the eIF4G1 gene.

Construction of the Vector pcDNA3.1-E2-bActin-U1U2U3 (FIG. 13)

Digestion BglII+XbaI on E2-bActin-U1U2U3
Recovery on gel of the fragment with 2618 bases, removal of the fragment with 4213 bases
Ligation with substitution of the promoter region in pcDNA3.1 already containing the light chain KT125 and obtaining pcDNA3.1-E2-bActin-U1U2U3
Screening by PCR with suitable primers, which gives an amplicon with 651 bases

Example 14

Figure 14:
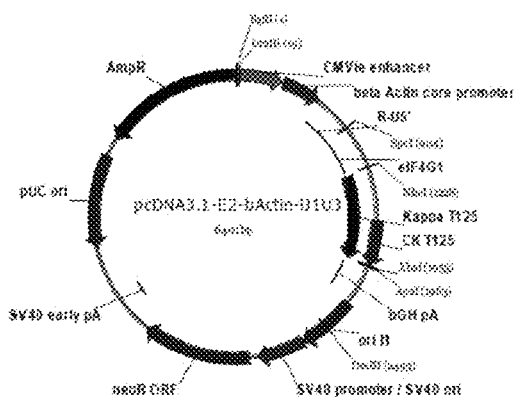
FIG. 14 illustrates the vector pcDNA3.1-E2-bActin-U1U3 originating from the vector pcDNA3.1 Invitrogen, comprising a transcription unit comprising the hCMVie enhancer, the promoter region of the CDK9 gene, the R region of the LTR of the HTLV-1 virus and the 5' UTR region of the eIF4G1 gene.

Construction of the Vector pcDNA3.1-E2-bActin-U1U3 (FIG. 14)

Digestion BglII+XbaI on E2-bActin-U1U3
Recovery on gel of the fragment with 1952 bases, removal of the fragment with 4213 bases
Ligation with substitution of the promoter region in pcDNA3.1 already containing the light chain KT125 and obtaining pcDNA3.1-E2-bActin-U1U3
Screening by PCR with suitable primers, which gives an amplicon with 578 bases

Example 15

Figure 15:
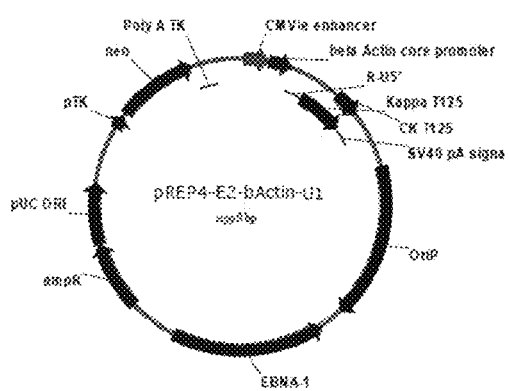
FIG. 15 illustrates the vector pREP4-E2-bActin-U1 originating from the vector pREP4, comprising a transcription unit comprising the hCMVie enhancer, the promoter region of β-actin and the R region of the LTR of the HTLV-1 virus.

Construction of the Vector pREP4-E2-bActin-U1 (FIG. 15)

Digestion BglII+XbaI on E2-bActin-U1
Recovery on gel of the fragment with 1628 bases, removal of the fragment with 4213 bases
Ligation with substitution of the promoter region in pREP4 already containing the light chain KT125 and obtaining pREP4-E2-bActin-U1
Screening by PCR with suitable primers, which gives an amplicon with 254 bases

Example 16

Figure 16:
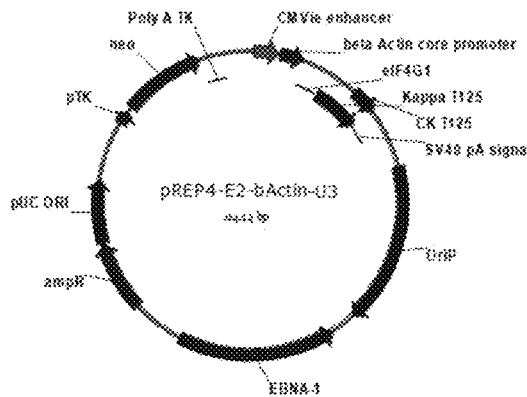
FIG. 16 illustrates the vector pREP4-E2-bActin-U3 originating from the vector pREP4, comprising a transcription unit comprising the hCMVie enhancer, the promoter region of β-actin and the 5' UTR region of the NRF gene.

Construction of the Vector pREP4-E2-bActin-U3 (FIG. 16)

Digestion BglII+XbaI on E2-bActin-U3
Recovery on gel of the fragment with 1674 bases, removal of the fragment with 4213 bases
Ligation with substitution of the promoter region in pREP4 already containing the light chain KT125 and obtaining pREP4-E2bActin-U3
Screening by PCR with suitable primers, which gives an amplicon with 752 bases

Example 17

Figure 17:
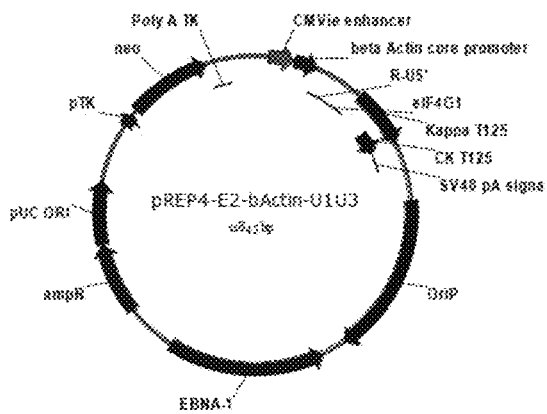
FIG. 17 illustrates the vector pREP4-E2-bActin-U1U3 originating from the vector pREP4, comprising a transcription unit comprising the hCMVie enhancer, the promoter region of β-actin, the R region of the LTR of the HTLV-1 virus and the 5' UTR region of the eIF4G1 gene.

Construction of the Vector pREP4-E2-bActin-U1U3 (FIG. 17)

Digestion SfuI+XbaI on pCEP4-E2-bActin-U1U3
Recovery on gel of the fragment with 4273 bases, removal of the fragment with 7188 bases
Ligation with substitution of the promoter region in pREP4 already containing the light chain KT125 and obtaining pREP4-E2-bActin-U1U3
Screening by PCR with suitable primers, which gives an amplicon with 578 bases

Example 18

Figure 18:
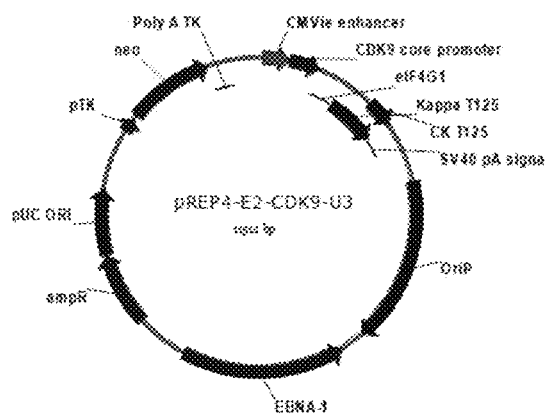
FIG. 18 illustrates the vector pREP4-E2-CDK9-U3 originating from the vector pREP4, comprising a transcription unit comprising the hCMVie enhancer, the promoter region of the CDK9 gene and the 5' UTR region of the NRF gene.

Construction of the Vector pREP4-E2-CDK9-U3 (FIG. 18)

Digestion BglII+XbaI on E2-CDK9-U3
Recovery on gel of the fragment with 1748 bases, removal of the fragment with 4213 bases
Ligation with substitution of the promoter region in pREP4 already containing the light chain KT125 and obtaining pREP4-E2-CDK9-U3
Screening by PCR with suitable primers, which gives an amplicon with 752 bases

Example 19

Figure 19:
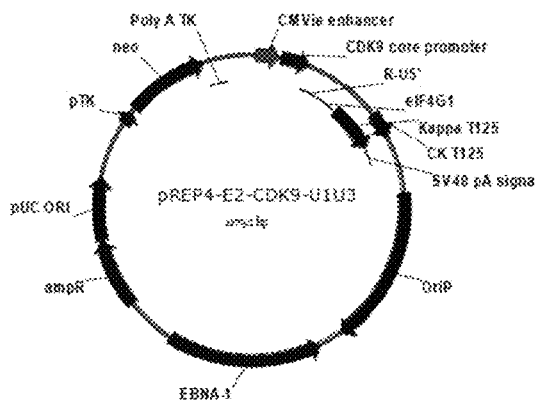
FIG. 19 illustrates the vector pREP4-E2-CDK9-U1U3 originating from the vector pREP4, comprising a transcription unit comprising the hCMVie enhancer, the promoter region of the CDK9 gene, the R region of the LTR of the HTLV-1 virus and the 5' UTR region of the eIF4G1 gene.

Construction of the Vector pREP4-E2-CDK9-U1U3 (FIG. 19)

Digestion BglII+XbaI on E2-CDK9-U1U3
Recovery on gel of the fragment with 2026 bases, removal of the fragment with 4213 bases
Ligation with substitution of the promoter region in pREP4 already containing the light chain KT125 and obtaining pREP4-E2-CDK9-U1U3
Screening by PCR with suitable primers, which gives an amplicon with 578 bases

Example 20

Figure 20:
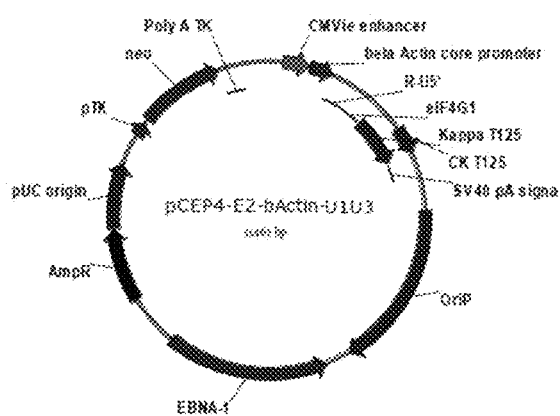
FIG. 20 illustrates the vector pcEP4-E2-bActin-U1U3 originating from the vector pCEP4, comprising a transcription unit comprising the hCMVie enhancer, the promoter region of β-actin, the R region of the LTR of the HTLV-1 virus and the 5' UTR region of the eIF4G1 gene.

Construction of the Vector pCEP4-E2-bActin-U1U3 (FIG. 20)

Digestion BglII+XbaI on E2-bActin-U1U3
Recovery on gel of the fragment with 1956 bases, removal of the fragment with 4213 bases
Ligation with substitution of the promoter region in pCEP4 already containing the light chain KT125 and obtaining pCEP4-E2-bActin-U1U3
Screening by PCR with suitable primers, which gives an amplicon with 578 bases

Example 21

Figure 21:
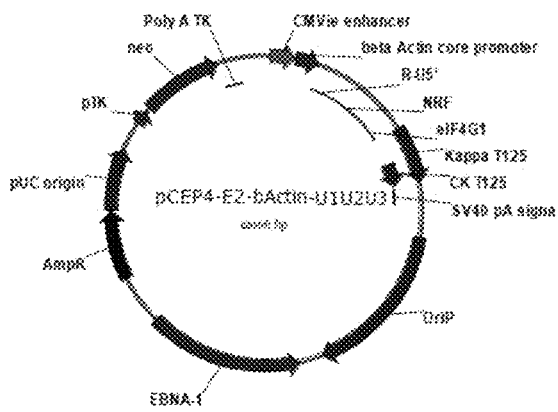
FIG. 21 illustrates the vector pcEP4-E2-bActin-U1U2U3 originating from the vector pCEP4, comprising a transcription unit comprising the hCMVie enhancer, the promoter region of β-actin, the R region of the LTR of the HTLV-1 virus, the 5' UTR region of the NRF gene and the 5' UTR region of the eIF4G1 gene.

Construction of the Vector pCEP4-E2-bActin-U1U2U3 (FIG. 21)

Digestion BglII+XbaI on E2-bActin-U1U2U3
Recovery on gel of the fragment with 2622 bases, removal of the fragment with 4213 bases Ligation with substitution of the promoter region in pCEP4 already containing the light chain KT125 and obtaining pCEP4-E2-bActin-U1U2U3
Screening by PCR with suitable primers, which gives an amplicon with 1010 bases

Example 22

Figure 22:
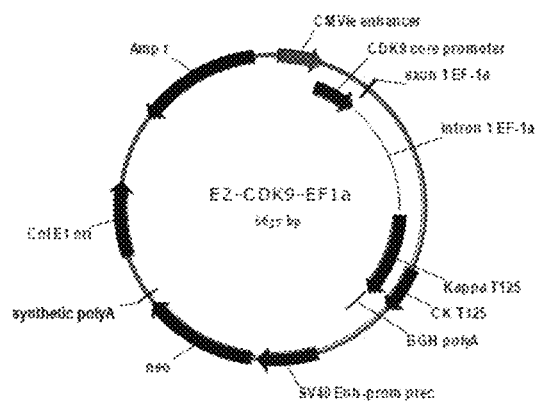
FIG. 22 illustrates the vector E2-CDK9-EF1α comprising a transcription unit comprising the hCMVie enhancer, the promoter region of the CDK9 gene and the first intron of the EF1α gene.

Construction of the Vector E2-CDK9-EF1α (FIG. 22)

Digestion SpeI+NheI of E2-CDK9
Recovery on gel of the fragment with 5636 bases, removal of the fragment with 198 bases
Digestion of the synthetic insert with SpeI and NheI
Recovery on gel of the insert with 1001 bases
Ligation and obtaining E2-CDK9-EF1α
Screening by PCR with suitable primers

Example 23

Figure 23:
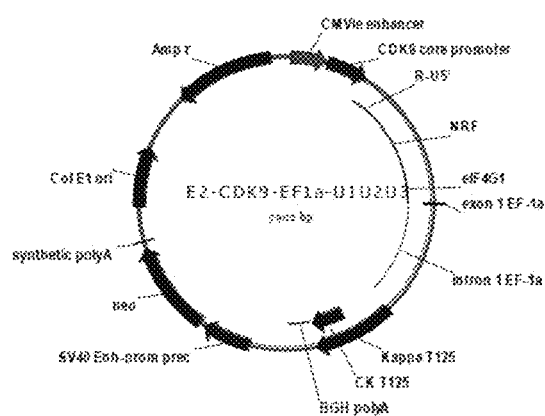
FIG. 23 illustrates the vector E2-CDK9-EF1α-U1U2U3 comprising a transcription unit comprising the hCMVie enhancer, the promoter region of the CDK9 gene, the first intron of the EF1α gene, the R region of the LTR of the HTLV-1 virus, the 5' UTR region of the NRF gene and the 5' UTR region of the eIF4G1 gene.

Construction of the Vector E2-CDK9-EF1α-U1U2U3 (FIG. 23)

Digestion SpeI+BamHI of E2-CDK9-EF1α
Recovery on gel of the fragment with 6631 bases, removal of the fragment with 6 bases
Digestion of the synthetic insert with BamHI and NheI
Recovery on gel of the insert with 1271 bases
Ligation and obtaining of E2-CDK9-EF1α-U1U2U3
Screening by PCR with suitable primers

Example 24

Figure 24:
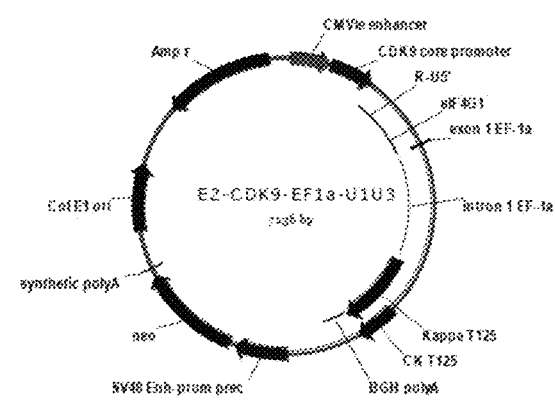
FIG. 24 illustrates the vector E2-CDK9-EF1α-U1U3 comprising a transcription unit comprising the hCMVie enhancer, the promoter region of the CDK9 gene, the first intron of the EF1α gene, the R region of the LTR of the HTLV-1 virus and the 5' UTR region of the eIF4G1 gene.

Construction of the Vector E2-CDK9-EF1α-U1U3 (FIG. 24)

Digestion SpeI on E2-CDK9-EF1α-U1U2U3
Recovery of the fragment with 7236 bases and removal of the fragment with 666 bases
Ligation and obtaining of E2-CDK9-EF1α-U1U3
Screening by PCR with suitable primers

Example 25

Figure 25:
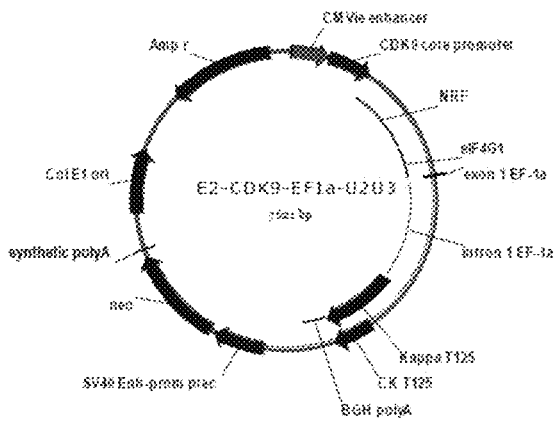
FIG. 25 illustrates the vector E2-CDK9-EF1α-U2U3 comprising a transcription unit comprising the hCMVie enhancer, the promoter region of the CDK9 gene, the first intron of the EF1α gene, the 5' UTR region of the NRF gene and the 5' UTR region of the eIF4G1 gene.

Construction of the Vector E2-CDK9-EF1α-U2U3 (FIG. 25)

Digestion HpaI/PmeI on E2-CDK9-EF1α-U1U2U3
Recovery of the fragment with 7230 bases, removal of the fragment with 672 bases
Ligation and obtaining of E2-CDK9-EF1α-U2U3
Screening by PCR with suitable primers

Example 26

Figure 26:
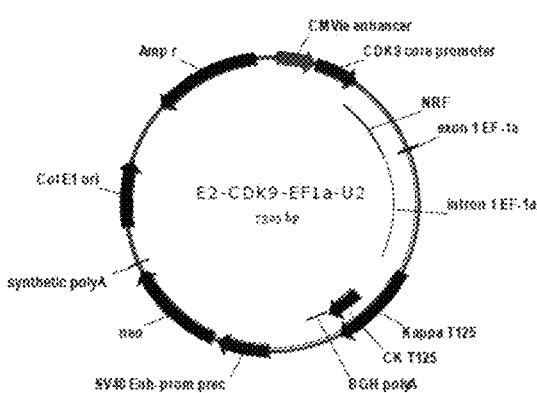
FIG. 26 illustrates the vector E2-CDK9-EF1α-U2 comprising a transcription unit comprising the hCMVie enhancer, the promoter region of the CDK9 gene, the first intron of the EF1α gene and the 5' UTR region of the NRF gene.

Construction of the Vector E2-CDK9-EF1α-U2 (FIG. 26)

Digestion SpeI of E2-CDK9-EF1α
Recovery on gel of the fragment with 6637 bases,
Digestion of the synthetic insert with SpeI
Recovery on gel of the insert with 666 bases
Ligation and obtaining of E2-CDK9-EF1α-U2
Screening by PCR with suitable primers

Example 27

Figure 27:
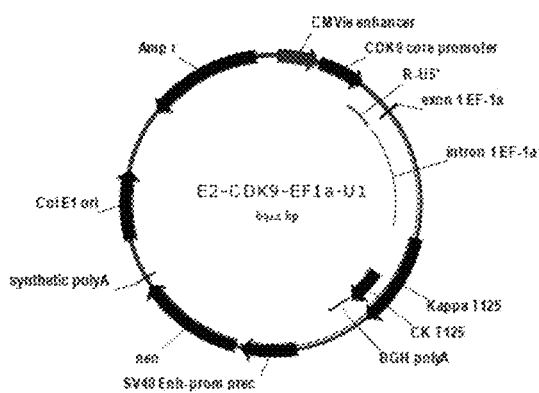
FIG. 27 illustrates the vector E2-CDK9-EF1α-U1 comprising a transcription unit comprising the hCMVie enhancer, the promoter region of the CDK9 gene, the first intron of the EF1α gene and the R region of the LTR of the HTLV-1 virus.

Construction of the Vector E2-CDK9-EF1α-U1 (FIG. 27)

Digestion BamHI+SpeI of E2-CDK9-EF1α
Recovery on gel of the fragment with 6631 bases and removal of the fragment with 6 bases
Digestion of the synthetic insert with BamHI+SpeI
Recovery on gel of the insert with 947 bases
Ligation and obtaining of E2-CDK9-EF1α-U1
Screening by PCR with suitable primers

Example 28

Figure 28:
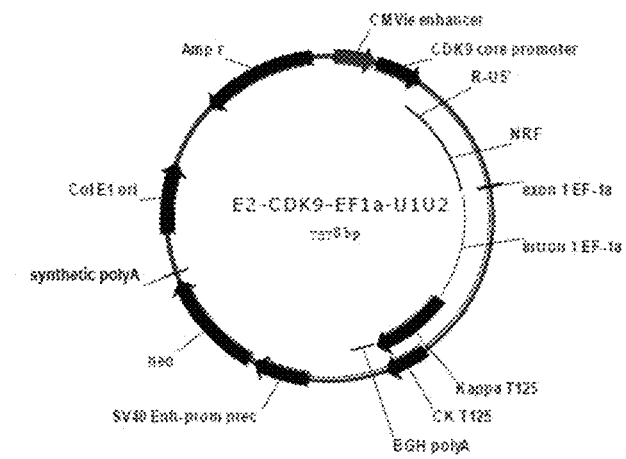
FIG. 28 illustrates the vector E2-CDK9-EF1α-U1U2 comprising a transcription unit comprising the hCMVie enhancer, the promoter region of the CDK9 gene, the first intron of the EF1α gene, the R region of the LTR of the HTLV-1 virus and the 5' UTR region of the NRF gene.

Construction of the Vector E2-CDK9-EF1α-U1U2 (FIG. 28)

Digestion SpeI of E2-CDK9-EF1α-U1
Recovery on gel of the fragment with 9612 bases
Digestion of the synthetic insert with SpeI
Recovery on gel of the insert with 947 bases
Ligation and obtaining of E2-CDK9-EF1α-U1U2
Screening by PCR with suitable primers

Example 29

Comparison of the Introns in Combination with the LTR RSV

The introns to be tested (Bact (β-actin), EF, mROSA, hROSA, HTLV, ubc (ubiquitin) are inserted into the expression vector K622_37, comprising the LTR RSV, to produce the light kappa chain of the T125 antibody. The productivity gain of the vectors thus constructed is compared with that of the reference vectors RSV_int_KT125_2STP and RSV_T125_K2.

The results obtained from 3 transfections carried out over the course of 3 different weeks are illustrated in FIG. 29 and reveal significant differences between the introns.

A multiple comparison is carried out for the mean values (ng/mL) of production of Ig light chain obtained with the different introns in the CHO-S line (Table 1). The method currently used for discriminating between the mean values is the Fisher least significant difference (LSD) method. Multiple extended tests are carried out with the 95.0% LSD method. These pairs have statistically significant differences at the 95.0% confidence level.

TABLE 1

|  | Sample size | Mean value | Homogeneous group |
|---|---|---|---|
| RSV_int_KT125_2STP | 18 | 25506.3 | X |
| K622_37_HTLV | 18 | 26511.3 | X |
| K622_37_Ubc | 18 | 28790.0 | XX |
| K622_37_Bact | 17 | 31992.3 | XX |
| K622_37_hROSA | 18 | 33561.0 | X |
| RSV_T125_K2 | 16 | 34362.8 | X |
| K622_37_mROSA | 15 | 38874.8 | X |
| K622_37_EF | 14 | 44104.4 | X |

Five homogeneous groups are identified using columns of X. The EF intron is significantly the most effective. The mROSA intron is in second place. The other introns do not have a positive effect in combination with the LTR RSV.

Example 30

Comparison of the Transcription Units in the Contexts of E2-CDK9-U3 and LTR RSV The different transcription units to be tested are tested for production of the light kappa chain of the T125 antibody. The productivity gain of the vectors thus constructed is compared with that of the reference vectors pRep4KT125 and RSV_T125_K2.

The results obtained from 3 transfections carried out over the course of 3 different weeks are illustrated in FIG. 30 and reveal significant differences between the combinations tested.

A multiple comparison is carried out for the mean values (ng/mL) of production of Ig light chain obtained with the different combinations in the CHO-S line (Table 2). The method currently used for discriminating between the mean values is the Fisher least significant difference (LSD) method. Multiple extended tests are carried out with the 95.0% LSD method. These pairs have statistically significant differences at the 95.0% confidence level.

TABLE 2

| | Sample size | Mean value | Homogeneous group |
|---|---|---|---|
| RSVT125K2 | 12 | 10940.2 | X |
| E2CDK9U3 hRosa | 12 | 15847.6 | X |
| K622__37 hRosa | 12 | 23340.0 | X |
| pRep4KT125 | 12 | 23843.2 | X |
| E2CDK9U3 | 12 | 31903.9 | X |
| K622__37 mRosa | 12 | 35041.1 | X |
| E2CDK9U3 mRosa | 12 | 40688.4 | X |
| K622__37 EF | 12 | 41708.2 | X |
| E2CDK9U3 EF | 12 | 51907.2 | X |

Five homogeneous groups are identified using columns of X.

The combination of E2-CDK9-U3 with the EF intron is significantly the most effective. In the context of E2-CDK9-U3, the EF intron thus supplies a gain of 63%.

The combinations of LTR RSV with EF intron and E2-CDK9-U3 with mROSA intron are also significantly very effective.

To a lesser extent, the other combinations tested are more effective than the reference RSV T125 K2.

Example 31

Production of the Whole Anti-Rh(D) Antibody (HK) by Vectors Containing E2CDK9U3

The whole anti-D antibodies (HK) are produced respectively in the CHO-S cells transfected by the vectors containing a transcription unit of structure E2-CDK9-U3 and in the CHO-S cells transfected by the vector containing a transcription unit of structure RSV-intron pCineo (reference vector).

Table 3 below shows the results from assay of the whole anti-D antibodies produced by pools of cells transfected by the vector HK463-18 or by the vector HK E2-CDK9-U3. These results are illustrated in FIG. 31.

TABLE 3

| Pool | Medium | Type of production batch | IgG assay by ELISA, in ng/ml | Gain E2CDK9U3/ RSV + intronpCI |
|---|---|---|---|---|
| F6-2 | Freestyle + G418 | D + 12 F25 | 2324 | |
| F11-2 | Freestyle + G418 | D + 12 F25 | 14 193 | 6.1 |

F6-2 = pool resulting from transfection with HK463-18;
F11-2 = pool resulting from transfection with HK E2-CDK9-U3

The transcription unit E2CDK9U3 makes it possible to obtain a productivity gain of the order of 6 times higher than that obtained with the reference vector.

Table 4 below shows the results from assay of the whole anti-D antibodies produced by the best clones (resulting from the method of screening described in Materials and Methods, on a limited number of colonies) originating from the pools described above, transfected by the vector HK463-18 or by the vector HK E2-CDK9-U3. These results are illustrated in FIG. 32.

TABLE 4

| | cultiflask | |
|---|---|---|
| name of vector | Prod Max D-1 ELISA IgG in ng/ml | prod max ELISA IgG in ng/ml |
| HK 463-18 | NA | <min |
| HK 463-18 | NA | 2 071 |
| HK 463-18 | NA | 2 732 |
| HK 463-18 | NA | 4 110 |
| HK 463-18 | NA | 16 937 |
| HK-E2-CDK9-U3 | NA | 4 061 |
| HK-E2-CDK9-U3 | NA | 10 585 |
| HK-E2-CDK9-U3 | 6 863 | 13 235 |
| HK-E2-CDK9-U3 | 13 389 | 14 221 |
| HK-E2-CDK9-U3 | 21 318 | 20 203 |
| HK-E2-CDK9-U3 | 29 860 | 33 069 |
| HK-E2-CDK9-U3 | 37 611 | 33 402 |
| HK-E2-CDK9-U3 | NA | 36 830 |
| HK-E2-CDK9-U3 | NA | 43 851 |
| HK-E2-CDK9-U3 | NA | 47 315 |
| HK-E2-CDK9-U3 | 58 007 | 58 007 |
| HK-E2-CDK9-U3 | 47 056 | 60 304 |
| HK-E2-CDK9-U3 | 61 902 | 74 233 |

The transcription unit E2-CDK9-U3 makes it possible to obtain a consistent productivity gain relative to the vector based on LTR RSV+intron pCI neo:
- the maximum productivity obtained with E2CDK9U3 is more than 4 times greater than that obtained with LTR RSV+intron pCI neo
- the productivities observed on the clones obtained with E2-CDK9-U3 are on average higher than those obtained with LTR RSV+intron pCI neo: average titre of 60.0 µg/ml on the clones obtained with E2-CDK9-U3, compared with an average titre of 6.5 µg/ml on the clones obtained with LTR RSV+intron pCI neo, or an average titre almost 10 times higher with E2-CDK9-U3

Example 32

Transient Expression of the T125 Kappa Chains in the CHO-S Line

The kappa chain is produced in the CHO-S cells transfected respectively by the vectors containing a transcription unit of structure: E2-bActin-Control, E2-bActin-U1, E2-bActin-U3 or E2-bActin-U1U2U3.

Table 5 below, as well as FIG. 33, illustrate the results from assay of the kappa chains in the culture medium.

These results show that a transcription unit according to the present invention containing at least one 5' UTR can increase the production of T125 kappa chains in the CHO-S cell line relative to that of a control vector only containing the hCMVie enhancer and the promoter of β-actin.

TABLE 5

|  | Sample size | Mean value | Homogeneous group |
|---|---|---|---|
| E2_bActin_Control | 10 | 35847.2 | X |
| E2_bActin_U1 | 12 | 43788.0 | X |
| E2_bActin_U3 | 11 | 44314.6 | X |
| E2_bActin_U1U2U3 | 12 | 44804.5 | X |
| E2_CDK9_U3 | 12 | 45551.4 | X |

The kappa chain was also produced in the CHO-S cells transfected respectively by the vectors pREP4-KT125, pREP4-E2-bActin-U3 or pREP4-E2-bActin-U1U3.

Table 6 as well as FIG. 35 illustrate the results from assay of the kappa chains in the culture medium.

TABLE 6

|  | Sample size | Mean value | Homogeneous group |
|---|---|---|---|
| pREP4_KT125 | 6 | 14813.8 | XX |
| pREP4_E2_bActin_U3 | 6 | 20493.9 | XX |
| pREP4_E2_bActin_U1U3 | 6 | 24185.5 | XX |

These results confirm that a transcription unit containing the hCMVie promoter, the promoter of β-actin and a 5' UTR makes it possible to increase the titration of recombinant proteins.

Example 33

Transient Expression of the T125 Kappa Chains in the HEK Line

The kappa chain is produced in the HEK cells transfected respectively by the vectors containing a transcription unit of structure: E2-bActin-Control, E2-bActin-U1 or E2-bActin-U1U2U3.

Table 7 below, as well as FIG. 34, illustrate the results from assay of the kappa chains in the culture medium.

These results show that a transcription unit according to the present invention containing at least one 5' UTR can also increase the titration of T125 kappa chains in the HEK cell line relative to that of a control vector only containing the hCMVie enhancer and the promoter of β-actin.

TABLE 7

|  | Sample size | Mean value | Homogeneous group |
|---|---|---|---|
| E2_bActin_Control | 11 | 13978.9 | X |
| E2_bActin_U1 | 5 | 37275.9 | X |
| E2_bActin_U1U2U3 | 11 | 76477.2 | X |

The kappa chain was also produced in the HEK cells transfected respectively by the vectors pCEP4-KT125 and pCEPT4-E2-bActin-U1U3.

The results illustrated in FIG. 36 confirm that a transcription unit according to the present invention makes it possible to increase the titration of recombinant proteins.

The invention claimed is:

1. A transcription unit comprising a polynucleotide comprising a sequence selected from the group consisting of:

(a) the sequence SEQ ID NO: 21, comprising:
   (i) a hCMVie virus enhancer consisting of nucleotide sequence SEQ ID NO: 1 and possessing an activity of transcription activation,
   (ii) a promoter region of B-actin consisting of nucleotide sequence SEQ ID NO: 3 and possessing a promoter activity, and
   (iii) a regulatory region R of 5' Long Terminal Repeat (LTR) of the HTLV-1 virus consisting of nucleotide sequence SEQ ID NO: 4 and having properties of stabilization of mRNA and a translation facilitator;

(b) the sequence SEQ ID NO: 22, comprising:
   (i) a hCMVie virus enhancer consisting of nucleotide sequence SEQ ID NO: 1 and possessing an activity of transcription activation,
   (ii) a promoter region of R-actin consisting of nucleotide sequence SEQ ID NO: 3 and possessing a promoter activity, and
   (iii) a 5' Untranslated Region (UTR) of a NF-KB Repressing Factor (NRF) gene consisting of nucleotide sequence SEQ ID NO: 5 and having properties of stabilization of mRNA and a translation facilitator;

(c) the sequence SEQ ID NO: 23, comprising:
   (i) a hCMVie virus enhancer consisting of nucleotide sequence SEQ ID NO: 1 and possessing an activity of transcription activation,
   (ii) a promoter region of R-actin consisting of the nucleotide sequence SEQ ID NO: 3 and possessing a promoter activity, and
   (iii) a 5' UTR region of an eukaryotic Initiation Factor 4GI (eIF4GI) gene consisting of nucleotide sequence SEQ ID NO: 6 and having properties of stabilization of mRNA and a translation facilitator;

(d) the sequence SEQ ID NO: 24, comprising:
   (i) a hCMVie virus enhancer consisting of nucleotide sequence SEQ ID NO: 1 and possessing an activity of transcription activation,
   (ii) a promoter region of R-actin consisting of the nucleotide sequence SEQ ID NO: 3 and possessing a promoter activity, and
   (iii) a 5' UTR region consisting of sequence SEQ ID NO: 7 and having properties of stabilization of mRNA and a translation facilitator;

(e) the sequence SEQ ID NO: 25, comprising:
   (i) a hCMVie virus enhancer consisting of nucleotide sequence SEQ ID NO: 1 and possessing an activity of transcription activation,
   (ii) a promoter region of B-actin consisting of nucleotide sequence SEQ ID NO: 3 and possessing a promoter activity, and (iii) a 5' UTR region consisting of sequence SEQ ID NO: 8 and having properties of stabilization of mRNA and a translation facilitator;

(f) the sequence SEQ ID NO: 26, comprising:
   (i) a hCMVie virus enhancer consisting of nucleotide sequence SEQ ID NO: 1 and possessing an activity of transcription activation,
   (ii) a promoter region of B-actin consisting of nucleotide sequence SEQ ID NO: 3 and possessing a promoter activity, and
   (iii) a 5' UTR region consisting of sequence SEQ ID NO: 9 and having properties of stabilization of mRNA and a translation facilitator; and (g) the sequence SEQ ID NO: 27, comprising:
   (i) a hCMVie virus enhancer consisting of nucleotide sequence SEQ ID NO: 1 and possessing an activity of transcription activation,
   (ii) a promoter region of B-actin consisting of nucleotide sequence SEQ ID NO: 3 and possessing a promoter activity, and
   (iii) a 5' UTR region consisting of sequence SEQ ID NO: 10 and having properties of stabilization of mRNA and a translation facilitator.

2. The transcription unit according to claim 1, wherein said polynucleotide comprises the nucleotide sequence of SEQ ID NO: 25, wherein said transcription unit, when expressed in a cell or cell line, is capable of producing a volume-based production of a protein of interest that is greater than that obtained with a transcription unit consisting of a combination of said CMV enhancer together with said promoter region of β-actin.

3. An expression vector comprising at least one transcription unit as defined according to claim 1 and at least one cloning site allowing integration of a nucleic acid coding for a protein of interest.

4. An expression vector comprising at least one transcription unit as defined according to claim 1 and at least one site for site-specific recombination allowing integration of a nucleic acid coding for a protein of interest.

5. The expression vector according to claim 3, further comprising a eukaryotic resistance gene, a bacterial resistance gene, a bacterial replication origin and a unit dedicated to gene amplification.

6. The expression vector according to claim 3, wherein said protein of interest is selected from the group consisting of the proteins participating in coagulation, immunoglobulins, cytokines, hormones, growth factors or complement factors and any fusion protein.

7. A host cell comprising an expression vector as defined in claim 3.

8. The host cell according to claim 7, wherein said host cell is a CHO-S, a CHO, or an HEK cell line.

* * * * *